(12) United States Patent
Whitesides et al.

(10) Patent No.: US 7,375,875 B2
(45) Date of Patent: May 20, 2008

(54) ELECTROPHORETIC MEDIA AND PROCESSES FOR THE PRODUCTION THEREOF

(75) Inventors: Thomas H. Whitesides, Somerville, MA (US); Qingye Zhou, Acton, MA (US); Russell J. Wilcox, Natick, MA (US)

(73) Assignee: E Ink Corporation, Cambridge, MA (US)

( * ) Notice: Subject to any disclaimer, the term of this patent is extended or adjusted under 35 U.S.C. 154(b) by 3 days.

(21) Appl. No.: 11/743,204

(22) Filed: May 2, 2007

(65) Prior Publication Data

US 2007/0201124 A1    Aug. 30, 2007

Related U.S. Application Data

(63) Continuation of application No. 10/711,829, filed on Oct. 7, 2004, now Pat. No. 7,230,750, which is a continuation-in-part of application No. 10/708,130, filed on Feb. 9, 2004, now Pat. No. 7,002,728, which is a continuation-in-part of application No. 10/063,803, filed on May 15, 2002, now Pat. No. 6,822,782.

(60) Provisional application No. 60/481,574, filed on Oct. 29, 2003, provisional application No. 60/481,486, filed on Oct. 8, 2003, provisional application No. 60/481,572, filed on Oct. 28, 2003, provisional application No. 60/291,081, filed on May 15, 2001.

(51) Int. Cl.
*G02B 26/00* (2006.01)
*G09G 3/34* (2006.01)
*G09G 3/20* (2006.01)
*C02F 1/40* (2006.01)
*G03G 17/04* (2006.01)

(52) U.S. Cl. .................. 359/296; 345/55; 345/107; 204/600; 204/601; 204/606; 430/32

(58) Field of Classification Search ............... 359/296, 359/452; 345/55, 107; 204/450, 600, 601, 204/606, 616; 430/32, 34, 38; 427/212, 427/216; 349/86; 252/583
See application file for complete search history.

(56) References Cited

U.S. PATENT DOCUMENTS 2,800,457 A    7/1957   Green et al.

(Continued)

FOREIGN PATENT DOCUMENTS

DE      195 00 694      8/1996

(Continued)

OTHER PUBLICATIONS

Amundson, K., et al., "Flexible, Active-Matrix Display Constructed Using a Microencapsulated Electrophoretic Material and an Organic-Semiconductor-Based Backplane", SID 01 Digest, 160 (Jun. 2001).

(Continued)

*Primary Examiner*—Loha Ben
(74) *Attorney, Agent, or Firm*—David J. Cole

(57) ABSTRACT

A first electrophoretic medium comprises an electrically charged particle suspended in a suspending fluid, the particle having a polymeric shell having repeating units derived from at least one monomer the homopolymer of which is incompatible with the suspending fluid. A second, similar electrophoretic medium comprises a suspending fluid, and first and second types of electrically charged particle suspended in the suspending fluid, the two types of particle having differing optical characteristics but both having polymeric shells. The polymeric shells are arranged such that homoaggregation of the two types of particles is thermodynamically favored over heteroaggregation.

20 Claims, 9 Drawing Sheets

U.S. PATENT DOCUMENTS

| | | |
|---|---|---|
| 3,036,388 A | 5/1962 | Tate |
| 3,384,488 A | 5/1968 | Tulagin et al. |
| 3,406,363 A | 10/1968 | Tate |
| 3,460,248 A | 8/1969 | Tate |
| 3,612,758 A | 10/1971 | Evans et al. |
| 3,639,133 A | 2/1972 | Linton |
| 3,668,106 A | 6/1972 | Ota |
| 3,670,323 A | 6/1972 | Sobel et al. |
| 3,756,693 A | 9/1973 | Ota |
| 3,767,392 A | 10/1973 | Ota |
| 3,772,013 A | 11/1973 | Wells |
| 3,792,308 A | 2/1974 | Ota |
| 3,806,893 A | 4/1974 | Ohnishi et al. |
| 3,850,627 A | 11/1974 | Wells et al. |
| 3,870,517 A | 3/1975 | Ota et al. |
| 3,892,568 A | 7/1975 | Ota |
| 4,001,140 A | 1/1977 | Foris et al. |
| 4,023,968 A | 5/1977 | Amidon et al. |
| 4,041,481 A | 8/1977 | Sato |
| 4,045,327 A | 8/1977 | Noma et al. |
| 4,062,009 A | 12/1977 | Raverdy et al. |
| 4,068,927 A | 1/1978 | White |
| 4,071,430 A | 1/1978 | Liebert |
| 4,088,395 A | 5/1978 | Gigila |
| 4,093,534 A | 6/1978 | Carter et al. |
| 4,113,362 A | 9/1978 | Saxe et al. |
| 4,123,346 A | 10/1978 | Ploix |
| 4,126,528 A | 11/1978 | Chiang |
| 4,126,854 A | 11/1978 | Sheridon |
| 4,143,103 A | 3/1979 | Sheridon |
| 4,143,472 A | 3/1979 | Murata et al. |
| 4,149,149 A | 4/1979 | Miki et al. |
| 4,164,365 A | 8/1979 | Saxe |
| 4,166,800 A | 9/1979 | Fong |
| 4,203,106 A | 5/1980 | Dalisa et al. |
| 4,211,668 A | 7/1980 | Tate |
| 4,218,302 A | 8/1980 | Dalisa et al. |
| 4,231,641 A | 11/1980 | Randin |
| 4,261,653 A | 4/1981 | Goodrich |
| 4,272,596 A | 6/1981 | Harbour et al. |
| 4,273,672 A | 6/1981 | Vassiliades |
| 4,285,801 A | 8/1981 | Chiang |
| 4,298,448 A | 11/1981 | Muller et al. |
| 4,305,807 A | 12/1981 | Somlyody |
| 4,311,361 A | 1/1982 | Somlyody |
| 4,314,013 A | 2/1982 | Chang |
| 4,324,456 A | 4/1982 | Dalisa |
| 4,368,952 A | 1/1983 | Murata et al. |
| 4,390,403 A | 6/1983 | Batchelder |
| 4,418,346 A | 11/1983 | Batchelder |
| 4,419,383 A | 12/1983 | Lee |
| 4,419,663 A | 12/1983 | Kohashi |
| 4,438,160 A | 3/1984 | Ishikawa et al. |
| 4,450,440 A | 5/1984 | White |
| 4,476,210 A | 10/1984 | Croucher et al. |
| 4,502,934 A | 3/1985 | Gazard et al. |
| 4,522,472 A | 6/1985 | Liebert et al. |
| 4,530,961 A | 7/1985 | Nguyen et al. |
| 4,543,306 A | 9/1985 | Dubois et al. |
| 4,594,271 A | 6/1986 | Scholten et al. |
| 4,620,916 A | 11/1986 | Zwemer et al. |
| 4,639,403 A | 1/1987 | Podszun et al. |
| 4,643,528 A | 2/1987 | Bell, Jr. |
| 4,648,956 A | 3/1987 | Marshall et al. |
| 4,655,897 A | 4/1987 | DiSanto et al. |
| 4,661,408 A | 4/1987 | Lau et al. |
| 4,665,107 A | 5/1987 | Micale |
| 4,680,103 A | 7/1987 | Beilin et al. |
| 4,690,749 A | 9/1987 | Van Alstine et al. |
| 4,707,080 A | 11/1987 | Fergason |
| 4,726,662 A | 2/1988 | Cromack |
| 4,732,830 A | 3/1988 | DiSanto et al. |
| 4,742,345 A | 5/1988 | Di Santo et al. |
| 4,746,917 A | 5/1988 | Di Santo et al. |
| 4,748,366 A | 5/1988 | Taylor |
| 4,772,102 A | 9/1988 | Fergason et al. |
| 4,772,103 A | 9/1988 | Saxe |
| 4,776,675 A | 10/1988 | Takaochi et al. |
| 4,810,305 A | 3/1989 | Braun et al. |
| 4,824,208 A | 4/1989 | Fergason et al. |
| 4,832,458 A | 5/1989 | Fergason et al. |
| 4,833,464 A | 5/1989 | Di Santo et al. |
| 4,846,893 A | 7/1989 | Akasaki et al. |
| 4,877,698 A | 10/1989 | Watson et al. |
| 4,888,309 A | 12/1989 | Araya |
| 4,889,603 A | 12/1989 | DiSanto et al. |
| 4,891,245 A | 1/1990 | Micale |
| 4,892,607 A | 1/1990 | DiSanto et al. |
| 4,902,570 A | 2/1990 | Heinemann et al. |
| 4,909,959 A | 3/1990 | Lemaire et al. |
| 4,919,521 A | 4/1990 | Tada et al. |
| 4,931,019 A | 6/1990 | Park |
| 4,946,509 A | 8/1990 | Schwartz et al. |
| 4,947,219 A | 8/1990 | Boehm |
| 4,985,329 A | 1/1991 | El-Sayed et al. |
| 5,009,490 A | 4/1991 | Kouno et al. |
| 5,017,225 A | 5/1991 | Nakanishi et al. |
| 5,041,824 A | 8/1991 | DiSanto et al. |
| 5,053,763 A | 10/1991 | DiSanto et al. |
| 5,057,363 A | 10/1991 | Nakanishi |
| 5,059,694 A | 10/1991 | Delabouglise et al. |
| 5,066,105 A | 11/1991 | Yoshimoto et al. |
| 5,066,559 A | 11/1991 | Elmasry et al. |
| 5,066,946 A | 11/1991 | DiSanto et al. |
| 5,070,326 A | 12/1991 | Yoshimoto et al. |
| 5,077,157 A | 12/1991 | DiSanto et al. |
| 5,082,351 A | 1/1992 | Fergason |
| 5,105,185 A | 4/1992 | Nakanowatari et al. |
| 5,119,218 A | 6/1992 | Yoshimoto et al. |
| 5,128,785 A | 7/1992 | Yoshimoto et al. |
| 5,132,049 A | 7/1992 | Garreau et al. |
| 5,138,472 A | 8/1992 | Jones et al. |
| 5,149,826 A | 9/1992 | Delabouglise et al. |
| 5,151,032 A | 9/1992 | Igawa |
| 5,174,882 A | 12/1992 | DiSanto et al. |
| 5,177,476 A | 1/1993 | DiSanto et al. |
| 5,185,226 A | 2/1993 | Grosso et al. |
| 5,187,609 A | 2/1993 | DiSanto et al. |
| 5,204,424 A | 4/1993 | Roncali et al. |
| 5,213,983 A | 5/1993 | Gustafsson et al. |
| 5,216,416 A | 6/1993 | DiSanto et al. |
| 5,223,115 A | 6/1993 | DiSanto et al. |
| 5,223,823 A | 6/1993 | Disanto et al. |
| 5,247,290 A | 9/1993 | Di Santo et al. |
| 5,250,932 A | 10/1993 | Yoshimoto et al. |
| 5,250,938 A | 10/1993 | DiSanto et al. |
| 5,254,981 A | 10/1993 | Disanto et al. |
| 5,262,098 A | 11/1993 | Crowley et al. |
| 5,266,937 A | 11/1993 | DiSanto et al. |
| 5,268,448 A | 12/1993 | Buechner et al. |
| 5,270,843 A | 12/1993 | Wang |
| 5,276,438 A | 1/1994 | DiSanto et al. |
| 5,279,511 A | 1/1994 | DiSanto et al. |
| 5,279,694 A | 1/1994 | DiSanto et al. |
| 5,279,773 A | 1/1994 | Saxe |
| 5,281,261 A | 1/1994 | Lin |
| 5,293,528 A | 3/1994 | DiSanto et al. |
| 5,296,974 A | 3/1994 | Tada et al. |
| 5,298,833 A | 3/1994 | Hou |
| 5,302,235 A | 4/1994 | DiSanto et al. |
| 5,303,073 A | 4/1994 | Shirota et al. |
| 5,304,439 A | 4/1994 | Disanto et al. |
| 5,315,312 A | 5/1994 | DiSanto et al. |
| 5,344,594 A | 9/1994 | Sheridon |

| | | | | | | |
|---|---|---|---|---|---|---|
| 5,359,346 A | 10/1994 | DiSanto et al. | | 5,759,671 A | 6/1998 | Tanaka et al. |
| 5,360,689 A | 11/1994 | Hou et al. | | 5,760,761 A | 6/1998 | Sheridon |
| 5,380,362 A | 1/1995 | Schubert | | 5,763,548 A | 6/1998 | Matyjaszewski et al. |
| 5,383,008 A | 1/1995 | Sheridon | | 5,767,826 A | 6/1998 | Sheridon et al. |
| 5,389,945 A | 2/1995 | Sheridon | | 5,777,782 A | 7/1998 | Sheridon |
| 5,402,145 A | 3/1995 | DiSanto et al. | | 5,783,614 A | 7/1998 | Chen et al. |
| 5,403,518 A | 4/1995 | Schubert | | 5,789,487 A | 8/1998 | Matyjaszewski et al. |
| 5,411,398 A | 5/1995 | Nakanishi et al. | | 5,803,959 A | 9/1998 | Johnson et al. |
| 5,411,656 A | 5/1995 | Schubert | | 5,807,937 A | 9/1998 | Matyjaszewski et al. |
| 5,421,926 A | 6/1995 | Yukinobu et al. | | 5,808,783 A | 9/1998 | Crowley |
| 5,463,492 A | 10/1995 | Check, III | | 5,825,529 A | 10/1998 | Crowley |
| 5,467,107 A | 11/1995 | DiSanto et al. | | 5,828,432 A | 10/1998 | Shashidhar et al. |
| 5,467,217 A | 11/1995 | Check, III | | 5,837,045 A | 11/1998 | Johnson et al. |
| 5,498,674 A | 3/1996 | Hou et al. | | 5,843,259 A | 12/1998 | Narang et al. |
| 5,508,068 A | 4/1996 | Nakano | | 5,851,280 A | 12/1998 | Belmont et al. |
| 5,512,162 A | 4/1996 | Sachs et al. | | 5,872,552 A | 2/1999 | Gordon, II et al. |
| 5,543,219 A | 8/1996 | Elwakil | | 5,885,335 A | 3/1999 | Adams et al. |
| 5,545,504 A | 8/1996 | Keoshkerian et al. | | 5,895,522 A | 4/1999 | Belmont et al. |
| 5,552,679 A | 9/1996 | Murasko | | 5,900,858 A | 5/1999 | Richley |
| 5,554,739 A | 9/1996 | Belmont | | 5,914,806 A | 6/1999 | Gordon II et al. |
| 5,556,583 A | 9/1996 | Tashiro et al. | | 5,922,118 A | 7/1999 | Johnson et al. |
| 5,561,443 A | 10/1996 | DiSanto et al. | | 5,930,026 A | 7/1999 | Jacobson et al. |
| 5,565,885 A | 10/1996 | Tamanoi | | 5,932,633 A | 8/1999 | Chen et al. |
| 5,571,311 A | 11/1996 | Belmont et al. | | 5,945,491 A | 8/1999 | Matyjaszewski et al. |
| 5,573,711 A | 11/1996 | Hou et al. | | 5,958,999 A | 9/1999 | Bates et al. |
| 5,575,845 A | 11/1996 | Belmont et al. | | 5,961,804 A | 10/1999 | Jacobson et al. |
| 5,582,700 A | 12/1996 | Bryning et al. | | 5,964,935 A | 10/1999 | Chen et al. |
| 5,597,889 A | 1/1997 | Takimoto et al. | | 5,968,243 A | 10/1999 | Belmont et al. |
| 5,604,027 A | 2/1997 | Sheridon | | 5,986,015 A | 11/1999 | Midha et al. |
| 5,604,070 A | 2/1997 | Rao et al. | | H1828 H | 1/2000 | Wong et al. |
| 5,610,455 A | 3/1997 | Allen et al. | | 6,017,584 A | 1/2000 | Albert et al. |
| 5,614,340 A | 3/1997 | Bugner et al. | | 6,025,896 A | 2/2000 | Hattori et al. |
| 5,627,561 A | 5/1997 | Laspina et al. | | 6,054,071 A | 4/2000 | Mikkelsen, Jr. |
| 5,635,317 A | 6/1997 | Taniguchi et al. | | 6,055,091 A | 4/2000 | Sheridon et al. |
| 5,638,103 A | 6/1997 | Obata et al. | | 6,055,180 A | 4/2000 | Gudesen et al. |
| 5,639,914 A | 6/1997 | Tomiyama et al. | | 6,064,784 A | 5/2000 | Whitehead et al. |
| 5,643,673 A | 7/1997 | Hou | | 6,067,185 A | 5/2000 | Albert et al. |
| 5,650,872 A | 7/1997 | Saxe et al. | | 6,068,688 A | 5/2000 | Whitehouse et al. |
| 5,654,367 A | 8/1997 | Takimoto et al. | | 6,069,205 A | 5/2000 | Wang |
| 5,663,224 A | 9/1997 | Emmons et al. | | 6,071,980 A | 6/2000 | Guan et al. |
| 5,672,198 A | 9/1997 | Belmont | | 6,091,382 A | 7/2000 | Shioya et al. |
| 5,672,381 A | 9/1997 | Rajan | | 6,097,531 A | 8/2000 | Sheridon |
| 5,673,148 A | 9/1997 | Morris et al. | | 6,103,380 A | 8/2000 | Devonport |
| 5,676,884 A | 10/1997 | Tiers et al. | | 6,111,022 A | 8/2000 | Matyjaszewski et al. |
| 5,689,282 A | 11/1997 | Wolfs et al. | | 6,113,810 A | 9/2000 | Hou et al. |
| 5,691,098 A | 11/1997 | Busman et al. | | 6,117,368 A | 9/2000 | Hou |
| 5,693,442 A | 12/1997 | Weiss et al. | | 6,118,426 A | 9/2000 | Albert et al. |
| 5,694,224 A | 12/1997 | Tai | | 6,120,588 A | 9/2000 | Jacobson |
| 5,698,016 A | 12/1997 | Adams et al. | | 6,120,839 A | 9/2000 | Comiskey et al. |
| 5,707,432 A | 1/1998 | Adams et al. | | 6,121,371 A | 9/2000 | Matyjaszewski et al. |
| 5,707,738 A | 1/1998 | Hou | | 6,124,411 A | 9/2000 | Matyjaszewski et al. |
| 5,707,747 A | 1/1998 | Tomiyama et al. | | 6,124,851 A | 9/2000 | Jacobson |
| 5,708,525 A | 1/1998 | Sheridon | | 6,128,124 A | 10/2000 | Silverman |
| 5,709,976 A | 1/1998 | Malhotra | | 6,130,773 A | 10/2000 | Jacobson et al. |
| 5,713,988 A | 2/1998 | Belmont et al. | | 6,130,774 A | 10/2000 | Albert et al. |
| 5,714,270 A | 2/1998 | Malhotra et al. | | 6,137,012 A | 10/2000 | Fagan et al. |
| 5,714,993 A | 2/1998 | Keoshkerian et al. | | 6,137,467 A | 10/2000 | Sheridon et al. |
| 5,715,511 A | 2/1998 | Aslam et al. | | 6,144,361 A | 11/2000 | Gordon, II et al. |
| 5,716,550 A | 2/1998 | Gardner et al. | | 6,147,791 A | 11/2000 | Sheridon |
| 5,717,283 A | 2/1998 | Biegelsen et al. | | 6,153,705 A | 11/2000 | Corpart et al. |
| 5,717,514 A | 2/1998 | Sheridon | | 6,162,882 A | 12/2000 | Matyjaszewski et al. |
| 5,717,515 A | 2/1998 | Sheridon | | 6,172,798 B1 | 1/2001 | Albert et al. |
| 5,725,935 A | 3/1998 | Rajan | | 6,177,921 B1 | 1/2001 | Comiskey et al. |
| 5,729,632 A | 3/1998 | Tai | | 6,184,856 B1 | 2/2001 | Gordon, II et al. |
| 5,737,115 A | 4/1998 | Mackinlay et al. | | 6,191,225 B1 | 2/2001 | Barkac et al. |
| 5,739,801 A | 4/1998 | Sheridon | | 6,197,883 B1 | 3/2001 | Schimmel et al. |
| 5,740,495 A | 4/1998 | Maher et al. | | 6,215,920 B1 | 4/2001 | Whitehead et al. |
| 5,744,283 A | 4/1998 | Spierings et al. | | 6,221,143 B1 | 4/2001 | Palumbo |
| 5,745,094 A | 4/1998 | Gordon, II et al. | | 6,225,971 B1 | 5/2001 | Gordon, II et al. |
| 5,747,562 A | 5/1998 | Mahmud et al. | | 6,232,950 B1 | 5/2001 | Albert et al. |
| 5,751,268 A | 5/1998 | Sheridon | | 6,235,829 B1 | 5/2001 | Kwan |
| 5,753,763 A | 5/1998 | Rao et al. | | 6,241,921 B1 | 6/2001 | Jacobson et al. |
| 5,754,332 A | 5/1998 | Crowley | | 6,249,271 B1 | 6/2001 | Albert et al. |

| | | | | | | |
|---|---|---|---|---|---|---|
| 6,252,564 B1 | 6/2001 | Albert et al. | | 2002/0060321 A1 | 5/2002 | Kazlas et al. |
| 6,262,706 B1 | 7/2001 | Albert et al. | | 2002/0063661 A1 | 5/2002 | Coomiskey et al. |
| 6,262,833 B1 * | 7/2001 | Loxley et al. ............... 359/296 | | 2002/0090980 A1 | 7/2002 | Wilcox et al. |
| 6,271,823 B1 | 8/2001 | Gordon, II et al. | | 2002/0113770 A1 | 8/2002 | Jacobson et al. |
| 6,300,932 B1 | 10/2001 | Albert | | 2002/0130832 A1 | 9/2002 | Baucom et al. |
| 6,301,038 B1 | 10/2001 | Fitzmaurice et al. | | 2002/0180687 A1 | 12/2002 | Webber |
| 6,312,304 B1 | 11/2001 | Duthaler et al. | | 2003/0011560 A1 | 1/2003 | Albert et al. |
| 6,312,971 B1 | 11/2001 | Amundson et al. | | 2003/0102858 A1 | 6/2003 | Jacobson et al. |
| 6,323,989 B1 | 11/2001 | Jacobson et al. | | 2003/0132908 A1 | 7/2003 | Herb et al. |
| 6,327,072 B1 | 12/2001 | Comiskey et al. | | 2003/0137521 A1 | 7/2003 | Zehner et al. |
| 6,376,828 B1 | 4/2002 | Comiskey | | 2003/0151702 A1 | 8/2003 | Morrison et al. |
| 6,377,387 B1 | 4/2002 | Duthaler et al. | | 2003/0214695 A1 | 11/2003 | Abramson et al. |
| 6,392,785 B1 | 5/2002 | Albert et al. | | 2003/0222315 A1 | 12/2003 | Amundson et al. |
| 6,392,786 B1 | 5/2002 | Albert | | 2004/0014265 A1 | 1/2004 | Kazlas et al. |
| 6,398,858 B1 | 6/2002 | Yu et al. | | 2004/0027327 A1 | 2/2004 | LeCain et al. |
| 6,413,790 B1 | 7/2002 | Duthaler et al. | | 2004/0075634 A1 | 4/2004 | Gates |
| 6,422,687 B1 | 7/2002 | Jacobson | | 2004/0094422 A1 | 5/2004 | Pullen et al. |
| 6,445,374 B2 | 9/2002 | Albert et al. | | 2004/0105036 A1 | 6/2004 | Danner et al. |
| 6,445,489 B1 | 9/2002 | Jacobson et al. | | 2004/0112750 A1 | 6/2004 | Jacobson et al. |
| 6,459,418 B1 | 10/2002 | Comiskey et al. | | 2004/0119681 A1 | 6/2004 | Albert et al. |
| 6,473,072 B1 | 10/2002 | Comiskey et al. | | 2004/0155857 A1 | 8/2004 | Duthaler et al. |
| 6,480,182 B2 | 11/2002 | Turner et al. | | 2004/0180476 A1 | 9/2004 | Kazlas et al. |
| 6,498,114 B1 | 12/2002 | Amundson et al. | | 2004/0190114 A1 | 9/2004 | Jacobson et al. |
| 6,504,524 B1 | 1/2003 | Gates et al. | | 2004/0196215 A1 | 10/2004 | Duthaler et al. |
| 6,506,438 B2 | 1/2003 | Duthaler et al. | | 2004/0226820 A1 | 11/2004 | Webber et al. |
| 6,512,354 B2 | 1/2003 | Jacobson et al. | | 2004/0239614 A1 | 12/2004 | Amundson et al. |
| 6,515,649 B1 | 2/2003 | Albert et al. | | 2004/0252360 A1 | 12/2004 | Webber et al. |
| 6,518,949 B2 | 2/2003 | Drzaic | | 2004/0257635 A1 | 12/2004 | Paolini, Jr. et al. |
| 6,521,489 B2 | 2/2003 | Duthaler et al. | | 2004/0263947 A1 | 12/2004 | Drzaic et al. |
| 6,525,866 B1 * | 2/2003 | Lin et al. .................... 359/296 | | 2005/0000813 A1 | 1/2005 | Pullen et al. |
| 6,529,313 B1 * | 3/2003 | Lin et al. .................... 359/296 | | 2005/0001812 A1 | 1/2005 | Amundson et al. |
| 6,531,997 B1 | 3/2003 | Gates et al. | | 2005/0007336 A1 | 1/2005 | Albert et al. |
| 6,535,197 B1 | 3/2003 | Comiskey et al. | | 2005/0007653 A1 | 1/2005 | Honeyman et al. |
| 6,538,801 B2 | 3/2003 | Jacobson et al. | | 2005/0012980 A1 | 1/2005 | Wilcox et al. |
| 6,545,291 B1 | 4/2003 | Amundson et al. | | 2005/0017944 A1 | 1/2005 | Albert |
| 6,580,545 B2 | 6/2003 | Morrison et al. | | 2005/0018273 A1 | 1/2005 | Honeyman et al. |
| 6,639,578 B1 | 10/2003 | Comiskey et al. | | 2005/0024353 A1 | 2/2005 | Amundson et al. |
| 6,657,772 B2 | 12/2003 | Loxley | | 2005/0035941 A1 | 2/2005 | Albert et al. |
| 6,664,944 B1 | 12/2003 | Albert et al. | | 2005/0041004 A1 | 2/2005 | Gates et al. |
| 6,672,921 B1 | 1/2004 | Liang et al. | | 2005/0062714 A1 | 3/2005 | Zehner et al. |
| 6,680,725 B1 | 1/2004 | Jacobson | | 2005/0067656 A1 | 3/2005 | Denis et al. |
| 6,683,333 B2 | 1/2004 | Kazlas et al. | | 2005/0122563 A1 | 6/2005 | Honeyman et al. |
| 6,693,620 B1 | 2/2004 | Herb et al. | | 2005/0151709 A1 | 7/2005 | Jacobson et al. |
| 6,704,133 B2 | 3/2004 | Gates et al. | | | | |
| 6,710,540 B1 | 3/2004 | Albert et al. | | FOREIGN PATENT DOCUMENTS | | |
| 6,721,083 B2 | 4/2004 | Jacobson et al. | | | | |
| 6,724,519 B1 | 4/2004 | Morrison et al. | | EP | 0 281 204 A2 | 9/1988 |
| 6,727,881 B1 | 4/2004 | Albert et al. | | EP | 0 404 545 A2 | 12/1990 |
| 6,753,999 B2 | 6/2004 | Zehner et al. | | EP | 0 443 571 A2 | 8/1991 |
| 6,788,449 B2 | 9/2004 | Liang et al. | | EP | 1 145 072 B1 | 5/2003 |
| 6,816,147 B2 | 11/2004 | Albert | | GB | 1314906 | 4/1973 |
| 6,819,471 B2 | 11/2004 | Amundson et al. | | GB | 1465701 | 3/1977 |
| 6,822,782 B2 | 11/2004 | Honeyman et al. | | GB | 2 306 229 A | 4/1997 |
| 6,825,068 B2 | 11/2004 | Denis et al. | | JP | 51-130241 A | 11/1976 |
| 6,825,829 B1 | 11/2004 | Albert et al. | | JP | 53-073098 | 6/1978 |
| 6,825,970 B2 | 11/2004 | Goenaga et al. | | JP | 54-111368 A | 8/1979 |
| 6,831,769 B2 | 12/2004 | Holman et al. | | JP | 55-096922 A | 7/1980 |
| 6,839,158 B2 | 1/2005 | Albert et al. | | JP | 55-105227 A | 8/1980 |
| 6,842,167 B2 | 1/2005 | Albert et al. | | JP | 59-098227 A | 6/1984 |
| 6,842,279 B2 | 1/2005 | Amundson | | JP | 59-165028 A | 9/1984 |
| 6,842,657 B1 | 1/2005 | Drzaic et al. | | JP | 60-189731 A | 9/1985 |
| 6,859,302 B2 | 2/2005 | Liang et al. | | JP | 62-058222 A | 3/1987 |
| 6,864,875 B2 | 3/2005 | Drzaic et al. | | JP | 62-183439 A | 8/1987 |
| 6,865,010 B2 | 3/2005 | Duthaler et al. | | JP | 62-231930 A | 10/1987 |
| 6,866,760 B2 * | 3/2005 | Paolini Jr. et al. .......... 204/478 | | JP | 62-269124 A | 11/1987 |
| 6,870,657 B1 | 3/2005 | Fitzmaurice et al. | | JP | 62-299824 A | 12/1987 |
| 6,870,661 B2 * | 3/2005 | Pullen et al. ............... 359/296 | | JP | 63-008637 A | 1/1988 |
| 6,922,276 B2 | 7/2005 | Zhang et al. | | JP | 01-086117 A | 3/1989 |
| 6,950,220 B2 | 9/2005 | Abramson et al. | | JP | 64-86116 | 3/1989 |
| 6,958,848 B2 | 10/2005 | Cao et al. | | JP | 64-086118 | 3/1989 |
| 6,967,640 B2 | 11/2005 | Albert et al. | | JP | 01-114829 A | 5/1989 |
| 7,079,305 B2 * | 7/2006 | Paolini et al. ............... 359/296 | | JP | 01-142537 A | 6/1989 |
| 7,236,290 B1 * | 6/2007 | Zhang et al. ............... 359/296 | | JP | 01-177517 A | 7/1989 |

| | | |
|---|---|---|
| JP | 01-248182 A | 10/1989 |
| JP | 01-267525 A | 10/1989 |
| JP | 02-024633 A | 1/1990 |
| JP | 02-141730 A | 5/1990 |
| JP | 02-189525 A | 7/1990 |
| JP | 02-223934 A | 9/1990 |
| JP | 02-223935 A | 9/1990 |
| JP | 02-223936 A | 9/1990 |
| JP | 02-284124 A | 11/1990 |
| JP | 02-284125 A | 11/1990 |
| JP | 03-258866 A | 11/1991 |
| JP | 05-061421 A | 3/1993 |
| JP | 05-165064 A | 6/1993 |
| JP | 05-173193 A | 7/1993 |
| JP | 05-173194 A | 7/1993 |
| JP | 05-307197 A | 11/1993 |
| JP | 06-089081 A | 11/1993 |
| JP | 06-202168 A | 7/1994 |
| JP | 07-036020 A | 2/1995 |
| JP | 07-146660 A | 6/1995 |
| JP | 08-234176 A | 9/1996 |
| JP | 09-006277 A | 1/1997 |
| JP | 09-185087 A | 7/1997 |
| JP | 09-230391 A | 9/1997 |
| JP | 10-048673 A | 2/1998 |
| JP | 10-149118 A | 6/1998 |
| JP | 10-161161 A | 6/1998 |
| JP | 2000-066248 | 3/2000 |
| JP | 2000-227612 | 8/2000 |
| WO | WO 82/02961 | 9/1982 |
| WO | WO 95/33085 | 12/1995 |
| WO | WO 99/12170 | 3/1999 |
| WO | WO 99/26419 | 5/1999 |
| WO | WO 99/51690 | 10/1999 |
| WO | WO 00/05312 | 2/2000 |
| WO | WO 00/05704 | 2/2000 |
| WO | WO 00/22051 | 4/2000 |
| WO | WO 00/36560 | 6/2000 |
| WO | WO 00/38000 | 6/2000 |
| WO | WO 00/67110 | 11/2000 |
| WO | WO 00/67327 | 11/2000 |
| WO | WO 01/07961 | 2/2001 |
| WO | WO 01/92359 | 12/2001 |
| WO | WO 02/21201 | 3/2002 |
| WO | WO 03/107315 | 12/2003 |

OTHER PUBLICATIONS

Au, J. et al., "Ultra-Thin 3.1-in. Active-Matrix Electronic Ink Display for Mobile Devices", IDW'02, 223 (2002).
Bach, U., et al., "Nanomaterials-Based Electrochromics for Paper-Quality Displays", Adv. Mater, 14(11), 845 (2002).
Ballinger, D.O., "Magnetic recording paper is erasable", Electronics, Mar. 1, 1973, pp. 73-76.
Beers, K.L., et al., "Atom Transfer Radical Polymerization of 2-Hydroxyethyl Methacrylate", Macromolecules, 32, 5772-5776 (1999).
Beilin, S., et al, "2000-Character Electrophoretic Display", SID 86 Digest, 136 (1986).
Bohnke et al., "Polymer-Based Solid Electrochromic Cell for Matrix-Addressable Display Devices." J. Electrochem. Soc., 138, 3612 (1991).
Boston Herald, "E Ink debuts in J.C. Penney Stores", May 3, 1999, p. 27.
Bouchard, A. et al., "High-Resolution Microencapsulated Electrophoretic Display on Silicon", SID 04 Digest, 651 (2004).
Bryce, M.R., "Seeing through synthetic metals", Nature, 335. 12 (1998).
Caillot, E. et al. "Active Matrix Electrophoretic Information Display for High Performance Mobile Devices", IDMC Proceedings (2003).
Chen, Y., et al., "A Conformable Electronic Ink Display using a Foil-Based a Si TFT Array", SID 01 Digest, 157 (Jun. 2001).
Chiang, A., "Conduction Mechanism of Charge Control Agents Used in Electrophoretic Display Devices", Proceeding of the S.I.D., 18, 275 (1977).
Chiang, A., et al., "A High Speed Electrophoretic Matrix Display", SID 80 Digest (1980), 114.
Comiskey, B. et al., "An electrophoretic ink for all-printed reflective electronic displays", Nature, 394, 253 (1998).
Comiskey, B., et al., "Electrophoretic Ink: A Printable Display Material", SID 97 Digest (1997), p. 75.
Croucher, M.D., et al., "Electrophoretic Display: Materials as Related to Performance", Photog. Sci. Eng., 25, 80 (1981).
Dalisa, A.L., "Electrophoretic Display Technology", IEEE Trans. Electron Dev., ED-24, 827 (1977).
Danner, G.M. et al., "Reliability Performance for Microencapsulated Electrophoretic Displays with Simulated Active Matrix Drive", SID 03 Digest, 573 (2003).
Drzaic, P., et al., "A Printed and Rollable Bistable Electronic Display", SID 98 Digest (1998), p. 1131.
Duthaler, G., et al., "Active-Matrix Color Displays Using Electrophoretic Ink and Color Filters", SID 02 Digest, 1374 (2002).
Egashira,. N., et al., "Solid electrochromic cell consisting of Lu-diphthalocyanine and lead flouride", Proceedings of the SID, 28, 227 (1987).
Fitzhenry, B., "Identification of a Charging Mechanism using Infrared Spectroscopy", Appl. Spectroscopy, 33, 107 (1979).
Fitzhenry, B., "Optical effects of adsorption of dyes on pigment used in electrophoretic image displays", Appl. Optics., 18, 3332 (1979).
Goodman, L.A., Passive Liquid Displays: Liquid Crystals, Electrophoretics and Electrochromics, Proceedings of S.I.D., 17, 30 (1976).
Gutcho, M.H., Microcapsules and Microencapsulation Techniques, Noyes Data Corp., Park Ridge NJ, (1976).
Hatano, T., et al., "18:3: Bistable Paper-White Display Device Using Cholesteric Liquid Crystals", SID 96 Digest, 269 (1996).
Henzen, A. et al., "An Electronic Ink Low Latency Drawing Tablet", SID 04 Digest, 1070 (2004).
Henzen, A. et al., "Development of Active Matrix Electronic Ink Displays for Handheld Devices", SID 03 Digest, 176, (2003).
Henzen, A. et al., "Development of Active Matrix Electronic Ink Displays for Smart Handheld Applications", IDW'02, 227 (2002).
Hou, J., et al., "Active Matrix Electrophoretic Displays Containing Black and White Particles with Opposite Polarities", SID 01 Digest, 164 (Jun. 2001).
Jacobson, J., et al., "The last book", IBM Systems J., 36, 457 (1997).
Ji, Y., et al., "P-50: Polymer Walls in Higher-Polymer-Content Bistable Reflective Cholesteric Displays", SID 96 Digest, 611 (1996).
Jin et al., "Optically Transparent,Electrically Conductive Composite Medium", Science, 255, 446 (1992).
Jo, G-R, et al., "Toner Display Based on Particle Movements", Chem. Mater, 14, 664 (2002).
Kazlas, P. et al., "Card-size Active-matrix Electronic Ink Display", Eurodisplay 2002, 259 (2002).
Kazlas, P., et al., "12.1" SVGA Microencapsulated Electrophoretic Active Matrix Display for Information Applicances, SID 01 Digest, 152 (Jun. 2001).
Kitamura, T., et al., "Electrical toner movement for electronic paper-like display", Asia Display/IDW'01, p. 1517, Paper HCS1-1 (2001).
Lee, L.L., "Fabrication of Magnetic Particles Displays", Proceedings of the SID, 18, 283 (1977).
Lewis et al., "Gravitational, Inter-Particle-Electrode Forces in the Electrophoretic Display", Proceedings of the SID, 18, 235 (1977).
Macosko, C.W., Rheology Principles, Methods, and Applications, VCH Publishers,1994, p. 481.
Milner, "Polymer Brushes", Science, 251, 905(1991).
Murau, P., et al., "An Electrophoretic Radiographic Device", SID 79 Digest, (1979) pp. 46-47.
Murau, P., et al., "The understanding and elimination of some suspension instabilities in an electrophoretic display", J. Appl. Phys., 49, 4820 (1978).

Negroponte, N., et al., "Surfaces and Displays," Wired, Jan. 1997, p. 212.

O'Regan, B. et al., "A Low Cost, High-efficiency Solar Cell Based on Dye-sensitized colloidal TiO2 Films", Nature, vol. 353, Oct. 24, 1991, 773-740.

Ota, I., et al., "Developments in Electrophoretic Displays", Proceedings of the SID, 18, 243 (1977).

Ota, I., et al., "Electrophoretic display devices", Laser 75 Optoelectronics Conference Proceedings, 145 (1975).

Ota, I., et al., "Electrophoretic Image Display (EPID) Panel", Proceedings of IEEE, 61, 832 (1973).

Pankove, "Color Reflection Type Display Panel", RCA Technical Notes, Mar. 1962, No. 535.

Pansu, B., et al., "Structures of Thin Layers of Hard Spheres: High Pressure Limit, " J. Physique, 45, 331 (1984).

Pansu, B., et al., "Thin colloidal crystals: a series of structural transitions,"J. Physique, 44, 531 (1983).

Pearlstein, "Electroless Plating", in Lowenheim (ed.), Modern Electroplating, Wiley, New York (1976), pp. 710-747.

Peiranski, P., et al., "Thin Colloidal Crystals," Phys. Rev. Lett., 50, 900 (1983).

Peterson, I., "Rethinking Ink Printing the Pages of an Electronic Book, " Science News, 153, 396 (Jun. 20, 1998).

Pitt, M.G., et al., "Power Consumption of Microencapsulated Electrophoretic Displays for Smart Handheld Applications", SID 02 Digest, 1378 (2002).

Platt, C., "Digital Ink," Wired, May 1997, p. 162.

Saitoh, M., et al., "A newly developed electrical twisting ball display", Proceedings of the SID, 23, 249 (1982).

Sankus, "Electrophoretic Display Cell", Xerox Disclosure Journal, 6(3), 309 (1979).

Sheridon, N.K., et al., "A Photoconductor-Addressed Electrophoretic Cell for Office Data Display", SID 82 Digest, 94 (1982).

Shiffman, R.R. et al., "An Electrophoretic Image Display with Internal NMOS Address Logic and Display Drivers," Proceedings of the SID, 1984, vol. 25, 105 (1984).

Shiwa, S., et al., "Electrophoretic Display Method Using Ionographic Techonology," SID 88 Digest (1988), p. 61.

Singer, B., et al., "An X-Y Addressable Electrophoretic Display," Proceedings of the SID, 18, 255 (1977).

Tanford, C., Physical Chemistry of Macromolecules, John Wiley and Sons, New York, 1961, pp. 293-296.

Tsubokawa, N., et al., "Polymerization of vinyl monomers in the presence of silica having surface functional groups", Colloid. Polym. Sci., 271, 940 (1993).

Van Winkle, D.H., et al., "Layering Transitions in Colloidal Crystals as Observed by Diffraction and Direct-Lattice Imaging", Phys. Rev. A, 34, 562 (1986).

Vance, D.W., "Optical Characteristics of Electrophoretic Displays", Proceedings of the SID, 18, 267 (1977).

Vandegaer, J. E. (ed.), "Microencapsulation Processes and Applications", pp. v-x, 1-180 (Plenum Press, New York 1974).

Vaz, N.A., et al., "Dual-frequency addressing of polymer-dispersed liquid-crystal films", J. Appl. Phys., 65, 5043 (1989).

Wang, J.S. et al., "Controlled/'Living' Radical Polymerization. Atom Transfer Radical Polymerization in the Presence of Transition-Metal Complexes", J. Am. Chem. Soc., 117, 5614.

Wang, J-S, et al., "Controlled/'Living' Radical Polymerization. Halogen Atom Transfer Radical Polymerization Promoted by a Cu(I)/Cu(II) Redox Process", Macromolecules 1995, 28, 7901-7910.

Webber, R., "Image Stability in Active-Matrix Microencapsulated Electrophoretic Displays", SID 02 Digest, 126 (2002).

White, R., "An Electrophoretic Bar Graph Display," Proceedings of the SID, 22, 173 (1981).

Whitesides, T. et al., "Towards Video-rate Microencapsulated Dual-Particle Electrophoretic Displays", SID 04 Digest, 133 (2004).

Wood, D., "An Electrochromic Renaissance?" Information Display, 18(3), 24 (Mar. 2002).

Yamaguchi, Y., et al., "Toner display using insulative particles charged triboelectrically", Asia Display/IDW '01, p. 1729, Paper AMD4-4 (2001).

Yang, Y., et al., "A new architecture for polymer transistors", Nature, 372, 344 (1994).

Zehner, R. et al., "Drive Waveforms for Active Matrix Electrophoretic Displays", SID 03 Digest, 842 (2003).

Zollinger, "Structures of Simple Di-Triarylmethine Dyes", in Color Chemistry: Syntheses, Properties and Applications of Organic Dyes and Pigments, 2nd Rev. Edition, VCH, Weinheim, p. 73 (1991).

Zurer, P., "Digital Ink Brings Electronic Books Closer," Chemical and Engineering News, Jul. 20, 1998, p. 12.

* cited by examiner

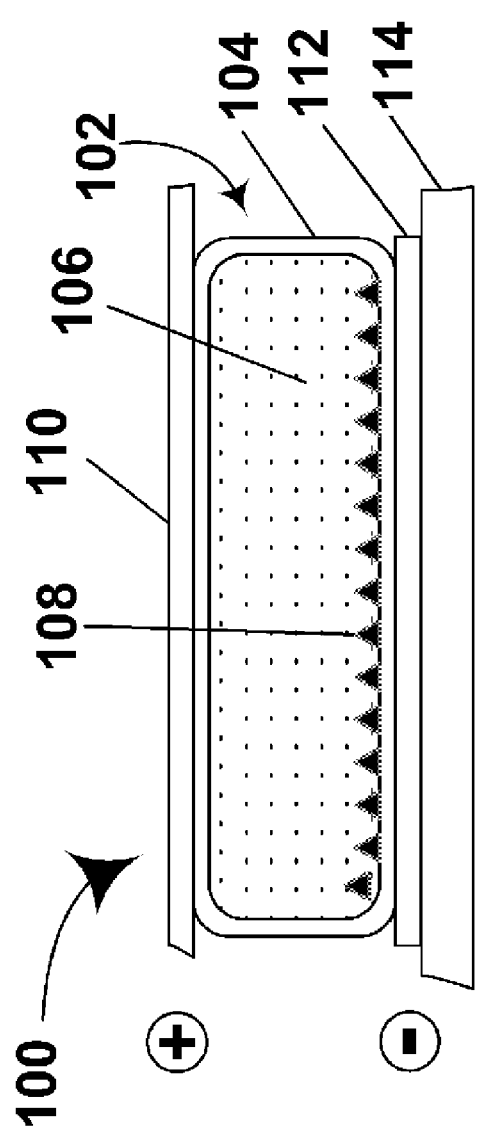
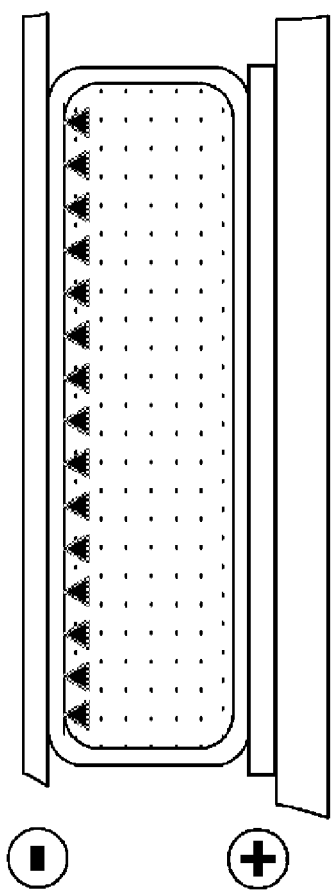

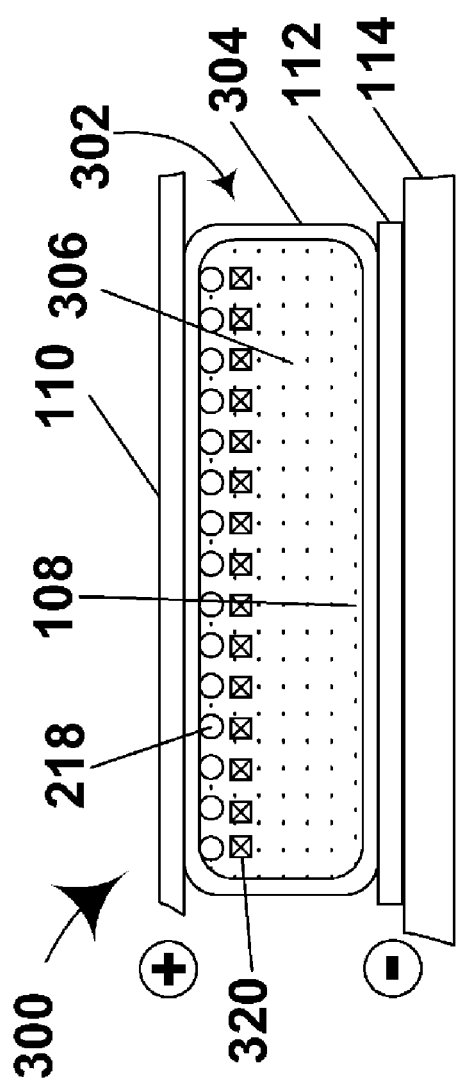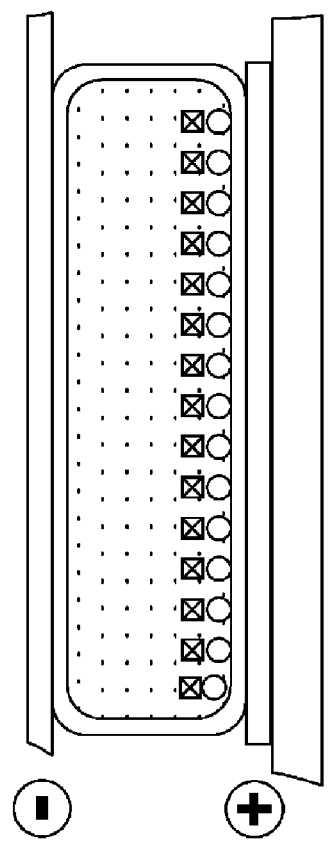

ELECTROPHORETIC MEDIA AND PROCESSES FOR THE PRODUCTION THEREOF

REFERENCE TO RELATED APPLICATIONS

This application is a continuation of application Ser. No. 10/711,829, filed Oct. 7, 2004 (Publication No. 2005/0168799), now U.S. Pat. No. 7,230,750 which is itself a continuation-in-part of application Ser. No. 10/708,130, filed Feb. 9, 2004 (now U.S. Pat. No. 7,002,728), which itself is a continuation-in-part of application Ser. No. 10/063,803 filed May 15, 2002 (now U.S. Pat. No. 6,822,782), which claims benefit of Application Ser. No. 60/291,081, filed May 15, 2001.

The aforementioned copending application Ser. No. 10/711,829 also claims benefit of the following provisional applications: (a) Application Ser. No. 60/481,486, filed Oct. 8, 2003; (b) Application Ser. No. 60/481,572, filed Oct. 28, 2003; and (c) Application Ser. No. 60/481,574, filed Oct. 29, 2003.

This application is also related to: (d) application Ser. No. 10/063,236, filed Apr. 2, 2002 (now U.S. Pat. No. 7,170,670), which claims benefit of Application Ser. No. 60/280,951, filed Apr. 2, 2001; (e) application Ser. No. 09/904,109 filed Jul. 12, 2001 (now U.S. Pat. No. 6,683,333), which claims benefit of Application Ser. No. 60/218,490, filed Jul. 14, 2000 (f) application Ser. No. 10/249,624, filed Apr. 24, 2003 (Publication No. 2004/0014265), which now U.S. Pat. No. 7,223,672 claims benefit of Application Ser. No. 60/375,248, filed Apr. 24, 2002 and Application Ser. No. 60/376,603, filed Apr. 30, 2002; and (g) application Ser. No. 10/249,618, filed Apr. 24, 2003 (now U.S. Pat. No. 7,116,318), which claims benefit of Application Ser. Nos. 60/375,508 and 60/375,571, both filed Apr. 24, 2002.

The entire contents of the aforementioned applications are herein incorporated by reference. The entire contents of all United States patents and published and copending Applications mentioned below are also herein incorporated by reference.

BACKGROUND OF INVENTION

The present invention relates to electrophoretic media. The present media are especially, although not exclusively, intended for use in encapsulated and microcell electrophoretic displays. The invention also relates to electrophoretic particles for use in such media, and to displays incorporating such media. Certain aspects of the present invention extend to electro-optic displays other than electrophoretic displays. The electrophoretic particles of the present invention are modified with polymers. The electro-optic displays of the present invention use an electro-optic medium having a voltage threshold.

In the displays of the present invention, the electro-optic medium (when a non-electrophoretic electro-optic medium) will typically be a solid (such displays may hereinafter for convenience be referred to as "solid electro-optic displays"), in the sense that the electro-optic medium has solid external surfaces, although the medium may, and often does, have internal liquid- or gas-filled spaces, and to methods for assembling displays using such an electro-optic medium. Thus, the term "solid electro-optic displays" includes encapsulated electrophoretic displays, encapsulated liquid crystal displays, and other types of displays discussed below.

The term "electro-optic", as applied to a material or a display, is used herein in its conventional meaning in the imaging art to refer to a material having first and second display states differing in at least one optical property, the material being changed from its first to its second display state by application of an electric field to the material. Although the optical property is typically color perceptible to the human eye, it may be another optical property, such as optical transmission, reflectance, luminescence or, in the case of displays intended for machine reading, pseudo-color in the sense of a change in reflectance of electromagnetic wavelengths outside the visible range.

The term "gray state" is used herein in its conventional meaning in the imaging art to refer to a state intermediate two extreme optical states of a pixel, and does not necessarily imply a black-white transition between these two extreme states. For example, several of the patents and published applications referred to below describe electrophoretic displays in which the extreme states are white and deep blue, so that an intermediate "gray state" would actually be pale blue. Indeed, as already mentioned the transition between the two extreme states may not be a color change at all.

The terms "bistable" and "bistability" are used herein in their conventional meaning in the art to refer to displays comprising display elements having first and second display states differing in at least one optical property, and such that after any given element has been driven, by means of an addressing pulse of finite duration, to assume either its first or second display state, after the addressing pulse has terminated, that state will persist for at least several times, for example at least four times, the minimum duration of the addressing pulse required to change the state of the display element. It is shown in published U.S. Patent Application No. 2002/0180687 that some particle-based electrophoretic displays capable of gray scale are stable not only in their extreme black and white states but also in their intermediate gray states, and the same is true of some other types of electro-optic displays. This type of display is properly called "multi-stable" rather than bistable, although for convenience the term "bistable" may be used herein to cover both bistable and multi-stable displays.

Several types of electro-optic displays are known. One type of electro-optic display is a rotating bichromal member type as described, for example, in U.S. Pat. Nos. 5,808,783; 5,777,782; 5,760,761; 6,054,071 6,055,091; 6,097,531; 6,128,124; 6,137,467; and 6,147,791 (although this type of display is often referred to as a "rotating bichromal ball" display, the term "rotating bichromal member" is preferred as more accurate since in some of the patents mentioned above the rotating members are not spherical). Such a display uses a large number of small bodies (typically spherical or cylindrical) which have two or more sections with differing optical characteristics, and an internal dipole. These bodies are suspended within liquid-filled vacuoles within a matrix, the vacuoles being filled with liquid so that the bodies are free to rotate. The appearance of the display is changed to applying an electric field thereto, thus rotating the bodies to various positions and varying which of the sections of the bodies is seen through a viewing surface. This type of electro-optic medium is typically bistable.

Another type of electro-optic display uses an electrochromic medium, for example an electrochromic medium in the form of a nanochromic film comprising an electrode formed at least in part from a semi-conducting metal oxide and a plurality of dye molecules capable of reversible color change attached to the electrode; see, for example O'Regan, B., et al., Nature 1991, 353, 737; and Wood, D., Information Display, 18(3), 24 (March 2002). See also Bach, U., et al., Adv. Mater., 2002, 14(11), 845. Nanochromic films of this type are also described, for example, in U.S. Pat. No. 6,301,038, International Application Publication No. WO 01/27690, and in U.S. Patent Application 2003/0214695. This type of medium is also typically bistable.

Another type of electro-optic display, which has been the subject of intense research and development for a number of years, is the particle-based electrophoretic display, in which a plurality of charged particles move through a suspending fluid under the influence of an electric field. Electrophoretic displays can have attributes of good brightness and contrast, wide viewing angles, state bistability, and low power consumption when compared with liquid crystal displays. Nevertheless, problems with the long-term image quality of these displays have prevented their widespread usage. For example, particles that make up electrophoretic displays tend to settle, resulting in inadequate service-life for these displays.

Numerous patents and applications assigned to or in the names of the Massachusetts Institute of Technology (MIT) and E Ink Corporation have recently been published describing encapsulated electrophoretic media. Such encapsulated media comprise numerous small capsules, each of which itself comprises an internal phase containing electrophoretically-mobile particles suspended in a liquid suspending medium, and a capsule wall surrounding the internal phase. Typically, the capsules are themselves held within a polymeric binder to form a coherent layer positioned between two electrodes. Encapsulated media of this type are described, for example, in U.S. Pat. Nos. 5,930,026; 5,961,804; 6,017,584; 6,067,185; 6,118,426; 6,120,588; 6,120,839; 6,124,851; 6,130,773; 6,130,774; 6,172,798; 6,177,921; 6,232,950; 6,249,271; 6,252,564; 6,262,706; 6,262,833; 6,300,932; 6,312,304; 6,312,971; 6,323,989; 6,327,072; 6,376,828; 6,377,387; 6,392,785; 6,392,786; 6,413,790; 6,422,687; 6,445,374; 6,445,489; 6,459,418; 6,473,072; 6,480,182; 6,498,114; 6,504,524; 6,506,438; 6,512,354; 6,515,649; 6,518,949; 6,521,489; 6,531,997; 6,535,197; 6,538,801; 6,545,291; 6,580,545; 6,639,578; 6,652,075; 6,657,772; 6,664,944; 6,680,725; 6,683,333; 6,704,133; 6,710,540; 6,721,083; 6,727,881; 6,738,050; 6,750,473; and 6,753,999; and U.S. Patent Applications Publication Nos. 2002/0019081; 2002/0021270; 2002/0060321; 2002/0063661; 2002/0090980; 2002/0113770; 2002/0130832; 2002/0131147; 2002/0171910; 2002/0180687; 2002/0180688; 2002/0185378; 2003/0011560; 2003/0020844; 2003/0025855; 2003/0038755; 2003/0053189; 2003/0102858; 2003/0132908; 2003/0137521; 2003/0137717; 2003/0151702; 2003/0214695; 2003/0214697; 2003/0222315; 2004/0008398; 2004/0012839; 2004/0014265; 2004/0027327; 2004/0075634; 2004/0094422; 2004/0105036; 2004/0112750; and 2004/0119681; and International Applications Publication Nos. WO 99/67678; WO 00/05704; WO 00/38000; WO 00/38001; WO00/36560; WO 00/67110; WO 00/67327; WO 01/07961; WO 01/08241; WO 03/107,315; WO 2004/023195; and WO 2004/049045.

Known electrophoretic media, both encapsulated and unencapsulated, can be divided into two main types, referred to hereinafter for convenience as "single particle" and "dual particle" respectively. A single particle medium has only a single type of electrophoretic particle suspended in a suspending medium, at least one optical characteristic of which differs from that of the particles. (In referring to a single type of particle, we do not imply that all particles of the type are absolutely identical. For example, provided that all particles of the type possess a charge of the same polarity, considerable variation in parameters such as particle color, size and electrophoretic mobility can be tolerated without affecting the utility of the medium. For example, two particles of different color, but the same charge, may be mixed in a single capsule, together with a single pigment (or multiple pigments) of opposite charge, to provide, by appropriate choice of the colors of these pigments, colors of any desired intermediate shade in either or both of the optical states.) When such a medium is placed between a pair of electrodes, at least one of which is transparent, depending upon the relative potentials of the two electrodes, the medium can display the optical characteristic of the particles (when the particles are adjacent the electrode closer to the observer, hereinafter called the "front" electrode) or the optical characteristic of the suspending medium (when the particles are adjacent the electrode remote from the observer, hereinafter called the "rear" electrode (so that the particles are hidden by the suspending medium).

A dual particle medium has two different types of particles differing in at least one optical characteristic and a suspending fluid which may be uncolored or colored, but which is typically uncolored. The two types of particles differ in electrophoretic mobility; this difference in mobility may be in polarity (this type may hereinafter be referred to as an "opposite charge dual particle" medium) and/or magnitude. When such a dual particle medium is placed between the aforementioned pair of electrodes, depending upon the relative potentials of the two electrodes, the medium can display the optical characteristic of either set of particles, although the exact manner in which this is achieved differs depending upon whether the difference in mobility is in polarity or only in magnitude. For ease of illustration, consider an electrophoretic medium in which one type of particles is black and the other type white. If the two types of particles differ in polarity (if, for example, the black particles are positively charged and the white particles negatively charged), the particles will be attracted to the two different electrodes, so that if, for example, the front electrode is negative relative to the rear electrode, the black particles will be attracted to the front electrode and the white particles to the rear electrode, so that the medium will appear black to the observer. Conversely, if the front electrode is positive relative to the rear electrode, the white particles will be attracted to the front electrode and the black particles to the rear electrode, so that the medium will appear white to the observer.

If the two types of particles have charges of the same polarity, but differ in electrophoretic mobility (this type of medium may hereinafter to referred to as a "same polarity dual particle" medium), both types of particles will be attracted to the same electrode, but one type will reach the electrode before the other, so that the type facing the observer differs depending upon the electrode to which the particles are attracted. For example suppose the previous illustration is modified so that both the black and white particles are positively charged, but the black particles have the higher electrophoretic mobility. If now the front electrode is negative relative to the rear electrode, both the black and white particles will be attracted to the front electrode, but the black particles, because of their higher mobility will reach it first, so that a layer of black particles will coat the front electrode and the medium will appear black to the observer. Conversely, if the front electrode is positive relative to the rear electrode, both the black and white particles will be attracted to the rear electrode, but the black particles, because of their higher mobility will reach it first, so that a layer of black particles will coat the rear electrode, leaving a layer of white particles remote from the rear electrode and facing the observer, so that the medium will appear white to the observer: note that this type of dual particle medium requires that the suspending fluid be sufficiently transparent to allow the layer of white particles remote from the rear electrode to be readily visible to the observer. Typically, the suspending fluid in such a display is not colored at all, but some color may be incorporated for the purpose of correcting any undesirable tint in the white particles seen therethrough, or to produce a desirable shade of color in the gray state.

Both single and dual particle electrophoretic displays may be capable of intermediate gray states having optical characteristics intermediate the two extreme optical states already described.

Some of the aforementioned patents and published applications disclose encapsulated electrophoretic media having three or more different types of particles within each capsule. For purposes of the present application, such multiparticle media are regarded as sub-species of dual particle media.

Also, many of the aforementioned patents and applications recognize that the walls surrounding the discrete microcapsules in an encapsulated electrophoretic medium could be replaced by a continuous phase, thus producing a so-called polymer-dispersed electrophoretic display, in which the electrophoretic medium comprises a plurality of discrete droplets of an electrophoretic fluid and a continuous phase of a polymeric material, and that the discrete droplets of electrophoretic fluid within such a polymer-dispersed electrophoretic display may be regarded as capsules or microcapsules even though no discrete capsule membrane is associated with each individual droplet; see for example, the aforementioned 2002/0131147. Accordingly, for purposes of the present application, such polymer-dispersed electrophoretic media are regarded as sub-species of encapsulated electrophoretic media.

A related type of electrophoretic display is a so-called "microcell electrophoretic display". In a microcell electrophoretic display, the charged particles and the suspending fluid are not encapsulated within microcapsules but instead are retained within a plurality of cavities formed within a carrier medium, typically a polymeric film. See, for example, International Application Publication No. WO 02/01281, and published US Application No. 2002/0075556, both assigned to Sipix Imaging, Inc.

Although electrophoretic media are often opaque (since, for example, in many electrophoretic media, the particles substantially block transmission of visible light through the display) and operate in a reflective mode, many electrophoretic displays can be made to operate in a so-called "shutter mode" in which one display state is substantially opaque and one is light-transmissive. See, for example, the aforementioned U.S. Pat. Nos. 6,130,774 and 6,172,798, and U.S. Pat. Nos. 5,872,552; 6,144,361; 6,271,823; 6,225,971; and 6,184,856. Dielectrophoretic displays, which are similar to electrophoretic displays but rely upon variations in electric field strength, can operate in a similar mode; see U.S. Pat. No. 4,418,346.

An encapsulated or microcell electrophoretic display typically does not suffer from the clustering and settling failure mode of traditional electrophoretic devices and provides further advantages, such as the ability to print or coat the display on a wide variety of flexible and rigid substrates. (Use of the word "printing" is intended to include all forms of printing and coating, including, but without limitation: pre-metered coatings such as patch die coating, slot or extrusion coating, slide or cascade coating, curtain coating; roll coating such as knife over roll coating, forward and reverse roll coating; gravure coating; dip coating; spray coating; meniscus coating; spin coating; brush coating; air knife coating; silk screen printing processes; electrostatic printing processes; thermal printing processes; ink jet printing processes; and other similar techniques.) Thus, the resulting display can be flexible. Further, because the display medium can be printed (using a variety of methods), the display itself can be made inexpensively.

However, the service life of encapsulated electrophoretic displays, of both the single and dual particle types, is still lower than is altogether desirable. It appears (although this invention is in no way limited by any theory as to such matters) that this service life is limited by factors such as sticking of the electrophoretic particles to the capsule wall, and the tendency of particles to aggregate into clusters which prevent the particles completing the movements necessary for switching of the display between its optical states. In this regard, opposite charge dual particle electrophoretic displays pose a particularly difficult problem, since inherently oppositely charged particles in close proximity to one another will be electrostatically attracted to each other and will display a strong tendency to form stable aggregates. Experimentally, it has been found that if one attempts to produce a black/white encapsulated display of this type using untreated commercially available titania and carbon black pigments, the display either does not switch at all or has a service life so short as to be undesirable for commercial purposes.

It has long been known that the physical properties and surface characteristics of electrophoretic particles can be modified by adsorbing various materials on to the surfaces of the particles, or chemically bonding various materials to these surfaces. For example, U.S. Pat. No. 4,285,801 (Chiang) describes an electrophoretic display composition in which the particles are coated with a highly fluorinated polymer, which acts as a dispersant, and which is stated to prevent the particles from flocculating and to increase their electrophoretic sensitivity. U.S. Pat. No. 4,298,448 (Müller et al.) describes an electrophoretic medium in which the particles are coated with an organic material, such as a wax, which is solid at the operating temperature of the medium but which melts at a higher temperature. The coating serves to lower the density of the electrophoretic particles and is also stated to increase the uniformity of the charges thereon. U.S. Pat. No. 4,891,245 describes a process for producing particles for use in electrophoretic displays, wherein a heavy, solid pigment, preferred for its high contrast or refractive index properties, is coated with a polymeric material. This process significantly reduces the specific density of the resultant particle, and is stated to create particles with smooth polymer surfaces that can be chosen for stability in a given electrophoretic carrier fluid, and possess acceptable electrophoretic characteristics. U.S. Pat. No. 4,680,103 (Beilin Solomon I et al.) describes a single particle electrophoretic display using inorganic pigment particles coated with an organosilane derivative containing quaternary ammonium groups; this coating is stated to provide quick release of the particles from the electrode adjacent the observer and resistance to agglomeration.

Later, it was found that simple coating of the electrophoretic particles with the modifying material was not entirely satisfactory since a change in operating conditions might cause part or all of the modifying material to leave the surface of the particles, thereby causing undesirable changes in the electrophoretic properties of the particles; the modifying material might possibly deposit on other surfaces within the electrophoretic display, which could give rise to further problems. Accordingly, techniques have been developed for securing the modifying material to the surface of the particles.

For example, U.S. Pat. No. 5,783,614 (Chen et al.) describes an electrophoretic display using diarylide yellow pigment particles modified with a polymer of pentafluorostyrene. The modified particles are produced by forming a mixture of the unmodified particles, the pentafluorostyrene monomer and a free radical initiator, and heating and agitating this mixture so that the monomer polymerizes in situ on the surface of the particles.

U.S. Pat. No. 5,914,806 (Gordon II et al.) describes electrophoretic particles formed by reacting pigment particles with a pre-formed polymer so that the polymer becomes covalently bonded to the surface of the particles. This process is of course restricted to pigments and polymers having chemical properties which allow the necessary reaction to form the covalent bond. Furthermore, a polymer with only a few sites capable of reacting with the particle material has difficulty in reacting with the solid interface at the particle surface; this can be due to polymer chain conformation in solution, steric congestion at the particle surface, or slow reactions between the polymer and the surface. Often, these problems restrict such reactions to short polymer chains, and such short chains typically only have a small effect on particle stability in electrophoretic media.

It is also known to use, in electrophoretic displays, particles consisting essentially of polymer; if dark colored particles are required, the polymer particles can be stained with a heavy metal oxide. See, for example, U.S. Pat. Nos. 5,360,689; 5,498,674; and 6,117,368. Although forming the electrophoretic particles from a polymer allows close control over the chemical composition of the particles, such polymer particles usually have much lower opacity than particles formed from inorganic pigments.

The aforementioned 2002/0185378 describes the advantages of using, in electrophoretic media, pigment particles which have polymer chemically bonded to, or cross-linked about, the pigment particles. This application also describes various improvements in such polymer-coated particles, including controlling the amount of polymer deposited on the particle, the structure of the polymer, techniques for forming the polymeric coating on the electrophoretic particles, and techniques for pretreatment of the electrophoretic particles before the formation of polymer coatings thereon. The application also describes a process for producing such a polymer-coated pigment particle, this process comprising: (a) reacting the pigment particle with a reagent having a functional group capable of reacting with, and bonding to, the particle, and also having a polymerizable or polymerization-initiating group, thereby causing the functional group to react with the particle surface and attach the polymerizable group thereto; and (b) reacting the product of step (a) with at least one monomer or oligomer under conditions effective to cause reaction between the polymerizable or polymerization-initiating group on the particle and the at least one monomer or oligomer, thereby causing the formation of polymer bonded to the pigment particle.

The aforementioned 2002/0180687 describes an electrophoretic medium comprising a plurality of particles suspended in a hydrocarbon suspending fluid, the particles being capable of moving through the fluid upon application of an electric field to the medium, the fluid having dissolved or dispersed therein a polyisobutylene having a viscosity average molecular weight in the range of about 400,000 to 1,200,000 g/mole, the polyisobutylene comprising from about 0.25 to about 2.5 percent by weight of the suspending fluid. The same application also describes an electrophoretic medium comprising a plurality of particles suspended in a suspending fluid, the particles being capable of moving through the fluid upon application of an electric field to the medium, the fluid having dissolved or dispersed therein a polymer having an intrinsic viscosity of $\eta$ in the suspending fluid and being substantially free from ionic or ionizable groups in the suspending fluid, the polymer being present in the suspending fluid in a concentration of from about 0.5 $[\eta]^{-1}$ to about 2.0 $[\eta]^{-1}$. The presence of the polyisobutylene (PIB) or other polymer in the suspending fluid substantially increases the bistability of the display.

As already indicated, electrophoretic displays require only low electrical power to switch from one state to another. For a bistable display, this low power requirement for switching translates directly into a low overall power requirement for operation of the display. However, electrophoretic displays do not have unlimited image stability. Brownian diffusion and gravitational settling of the pigment particles, together with motion driven by small residual voltages induced by the applied switching pulse and other factors, all can degrade the optical state achieved by switching of the display. In cases where there is no mechanism to prevent this kind of optical state decay, the optical state must be periodically refreshed. Refreshing the display consumes power, and thus diminishes the utility of the display. In addition, in certain applications (active matrix driven displays in particular) it is difficult or impossible to accomplish the refreshing of a single pixel without a blanking pulse (i.e., a pulse which drives the pixel to one of its extreme optical states before it is driven to the final desired optical state cf. the aforementioned 2003/0137521. For these reasons, improvements in the image stability of electrophoretic media are still highly desirable.

Also as already discussed, the aforementioned 2002/0180687 describes electrophoretic media which achieve good image stability by incorporation of a high molecular weight polymer, for example PIB, that has good solubility in the suspending medium (typically an aliphatic hydrocarbon such as Isopar G) but which is not absorbed on the electrophoretic particles. The presence of this polymer in solution is believed (although the present invention is in no way limited by this belief) to induce a weak flocculation of the pigments by a mechanism known in the colloid science art as "depletion flocculation". Polymers other than PIB can be used for the same purpose. An example of a second polymer that has been shown to be useful for this purpose is Kraton G, a block copolymer comprising a polystyrene block and a hydrogenated polyisobutylene block, that forms aggregate structures in the suspending medium. In this case, the aggregates are the species that induce the depletion flocculation, rather than the monomeric block copolymer itself.

No matter what polymer is used to induce depletion, the incorporation of soluble, high molecular weight materials into the suspending medium will increase the viscosity of that medium. Since the response time of the display (the time needed at a given operating voltage to change the display, or any given pixel thereof, between its two extreme optical states) is proportional to the viscosity of the medium, the switching speed of the display will be reduced by this approach to image stability. Furthermore, since the depletion flocculation mechanism is only active at concentrations of polymer above the overlap concentration (which can be operationally defined as the concentration of polymer that causes the viscosity of the medium to increase by a factor of two), all polymers that act by this mechanism can be expected to produce a similar diminution of the switching speed. In practice, the switching speed is reduced by approximately a factor of two to three when enough polymer is used to give adequate image stability. It is desirable to have other means of achieving image stability that do not suffer from this tradeoff with response time.

As discussed above, PIB and other polymers improve image stability by manipulating the colloidal stability of the pigment particles. The preferred polymer coated particles described in the aforementioned 2002/0185378 are colloidally stable in the suspending medium because of a polymer shell of (typically) poly(lauryl methacrylate) that is grown on the surface of the particles during their preparation. By appropriate manipulation of the composition of the polymer shell, it is possible in principle to make particles with the same degree of colloidal stability (and hence displays with the same image stability) as that afforded by PIB, Kraton, and other polymers dispersed in the suspending medium but without requiring addenda like PIB in the suspending medium. Such displays should be substantially faster than displays that contain PIB, or equivalently, should operate at equivalent speed at lower applied voltage.

In one aspect, this invention seeks to provide approaches to providing electrophoretic particles with modified polymer shells that allow the production of fast, image-stable displays.

In other aspect, this invention seeks to provide an improved form of the two-step process for preparing such polymer-coated electrophoretic particles described in Paragraph 31 above. In preferred forms of this process, titania (or a similar metal oxide pigment) is first coated with silica, and the silica-coated titania is treated with a silane containing an ethylenic group. The resultant silane-treated titania may then be reacted with a variety of unsaturated monomers, for example, 2-ethylhexyl acrylate or lauryl methacrylate, in the presence of a free-radical polymerization initiator, to form the desired polymer-coated titania. Carbon black is treated with a diazotizing agent containing an ethylenic group, for example, the reaction product of 4-vinylaniline and nitrous acid, to attach ethylenic groups to the carbon black surface, and thereafter may be reacted with a variety of unsaturated monomers in substantially the same way as described for titania.

In the specific processes shown in the Examples of the aforementioned 2002/0185378, the final polymerization steps (the so-called "graft polymerization steps") are conducted in toluene, primarily because this is a solvent known in the polymer industry to have good properties for use in such free radical polymerizations. However, its use as a solvent in processes for preparing polymer-coated electrophoretic pigment particles is markedly inconvenient. For various reasons discussed at length in the aforementioned E Ink and MIT patents and applications, in practice the suspending fluid used in electrophoretic displays is an aliphatic hydrocarbon (alone or in combination with a halocarbon). Thus, since the polymer-coated pigment particles will eventually be dispersed in an aliphatic hydrocarbon, and it is necessary to avoid contaminating this aliphatic hydrocarbon with toluene (since the behavior of electrophoretic media tends in certain cases to be highly sensitive to small changes in the composition of the suspending fluid), after the polymerization in toluene is finished and the polymer-coated pigment separated from the toluene, it is necessary to remove all traces of the toluene before the polymer-coated pigment particles are suspended in the final suspending fluid. In practice, it is necessary to wash the toluene-containing pigment particles from the graft polymerization step one or more times with tetrahydrofuran (THF), centrifuge after washing to separate the pigment from the THF and finally to dry the pigment in an oven to remove the last traces of THF. All these processes have to be carried out separately on the two pigments used in a dual particle electrophoretic medium.

These washing, centrifuging and drying steps are labor intensive and costly. Further expense is incurred by the need to re-disperse the dried pigment in the final suspending fluid. Furthermore, because of the presence of the toluene and THF, the washing, centrifuging and drying steps tend to be hazardous and commercial scale production of the polymer-coated pigment requires the use of explosion-proof ovens, mixers and centrifuges, and explosion-proof electrical control panels, which substantially increases the costs of the production equipment. Also, operator exposure to vapors during processing can be significant despite the use of protective devices or exposure prevention methods. Finally, the drying step may be detrimental to the performance of the pigment in the final electrophoretic medium. It is therefore desirable to find an alternative solvent in which the polymerization reaction can be carried out, and if possible to eliminate the need for drying and re-dispersion of the dried pigment.

Finally, this invention seeks to provide electro-optic displays which are capable of being driven in a simplified manner. Whether a display is reflective or transmissive, and whether or not the electro-optic medium used is bistable, to obtain a high-resolution display, individual pixels of a display must be addressable without interference from adjacent pixels. One way to achieve this objective is to provide an array of non-linear elements, such as transistors or diodes, with at least one non-linear element is associated with each pixel, to produce an "active matrix" display. An addressing or pixel electrode, which addresses one pixel, is connected to an appropriate voltage source through the associated non-linear element. Typically, when the non-linear element is a transistor, the pixel electrode is connected to the drain of the transistor, and this arrangement will be assumed in the following description, although it is essentially arbitrary and the pixel electrode could be connected to the source of the transistor. Conventionally, in high resolution arrays, the pixels are arranged in a two-dimensional array of rows and columns, such that any specific pixel is uniquely defined by the intersection of one specified row and one specified column. The sources of all the transistors in each column are connected to a single column electrode, while the gates of all the transistors in each row are connected to a single row electrode; again the assignment of sources to rows and gates to columns is conventional but essentially arbitrary, and could be reversed if desired. The row electrodes are connected to a row driver, which essentially ensures that at any given moment only one row is selected, i.e., that there is applied to the selected row electrode a voltage such as to ensure that all the transistors in the selected row are conductive, while there is applied to all other rows a voltage such as to ensure that all the transistors in these non-selected rows remain non-conductive. The column electrodes are connected to column drivers, which place upon the various column electrodes voltages selected to drive the pixels in the selected row to their desired optical states. (The aforementioned voltages are relative to a common front electrode which is conventionally provided on the opposed side of the electro-optic medium from the non-linear array and extends across the whole display.) After a pre-selected interval known as the "line address time" the selected row is deselected, the next row is selected, and the voltages on the column drivers are changed to that the next line of the display is written. This process is repeated so that the entire display is written in a row-by-row manner. Thus, in a display with N rows, any given pixel can only be addressed for a fraction 1/N of the time.

Processes for manufacturing active matrix displays are well established. Thin-film transistors, for example, can be fabricated using various deposition and photolithography techniques. A transistor includes a gate electrode, an insulating dielectric layer, a semiconductor layer and source and drain electrodes. Application of a voltage to the gate electrode provides an electric field across the dielectric layer, which dramatically increases the source-to-drain conductivity of the semiconductor layer. This change permits electrical conduction between the source and the drain electrodes. Typically, the gate electrode, the source electrode, and the drain electrode are patterned. In general, the semiconductor layer is also patterned in order to minimize stray conduction (i.e., cross-talk) between neighboring circuit elements.

Liquid crystal displays commonly employ amorphous silicon ("a-Si") thin-film transistors ("TFT's") as switching devices for display pixels. Such TFT's typically have a bottom-gate configuration. Within one pixel, a thin-film capacitor typically holds a charge transferred by the switching TFT. Electrophoretic displays can use similar TFT's with capacitors, although the function of the capacitors differs somewhat from those in liquid crystal displays; see copending application Ser. No. 09/565,413, filed May 5, 2000 (now U.S. Pat. No. 7,030,412), and U.S. Patent Publications Nos. 2002/0106847 and 2002/0060321. Thin-film transistors can be fabricated to provide high performance. Fabrication processes, however, can result in significant cost.

In TFT addressing arrays, pixel electrodes are charged via the TFT's during a line address time. During the line address time, a TFT is switched to a conducting state by changing an applied gate voltage. For example, for an n-type TFT, a gate voltage is switched to a "high" state to switch the TFT into a conducting state.

Undesirably, the pixel electrode typically exhibits a voltage shift when the select line voltage is changed to bring the TFT channel into depletion. The pixel electrode voltage shift occurs because of the capacitance between the pixel electrode and the TFT gate electrode. The voltage shift can be modeled as:

$$\Delta V_p = G_{gp}\Delta/(C_{gp}+C_p+C_s)$$

where $C_{gp}$ is the gate-pixel capacitance, $C_p$ the pixel capacitance, $C_s$ the storage capacitance and $\Delta$ is the fraction of the gate voltage shift when the TFT is effectively in depletion. This voltage shift is often referred to as "gate feedthrough".

Gate feedthrough can compensated by shifting the top plane voltage (the voltage applied to the common front electrode) by an amount $\Delta V_p$. Complications arise, however, because $\Delta V_p$ varies from pixel to pixel due to variations of $C_{gp}$ from pixel to pixel. Thus, voltage biases can persist even when the top plane is shifted to compensate for the average pixel voltage shift. The voltage biases can cause errors in the optical states of pixels, as well as degrade the electro-optic medium.

Variations in $C_{gp}$ are caused, for example, by misalignment between the two conductive layers used to form the gate and the source-drain levels of the TFT; variations in the gate dielectric thickness; and variations in the line etch, i.e., line width errors.

Some tolerance for mis-registered conductive layers can be obtained by utilizing a gate electrode that completely overlaps the drain electrode. This technique, however, can cause a large gate-pixel capacitance. A large gate-pixel capacitance is undesirable because it can create a need for a large compensation in one of the select line voltage levels. Moreover, existing addressing structures can produce unintended bias voltages, for example, due to pixel-to-pixel variations in gate-pixel capacitance. Such voltages can produce a detrimental effect on certain electro-optic media, particularly when present for extended periods of time.

The foregoing problems render designing a bistable electro-optic display using a electro-optic medium without a voltage threshold a difficult task. Since some pixels on the display may be updated infrequently, if at all, one must ensure that the optical state of the pixel remains unperturbed as much as possible. Practically, this means minimizing the quantity and amplitude of parasitic voltage spikes that are applied to the pixel.

As an example, consider the voltages applied to the source (data) lines of an active matrix display being scanned in the conventional manner described above. In an encapsulated electrophoretic display, these lines are switching between +15V and −15V relative to the common electrode, as frequently as every line address time (the time for which a given row of the active matrix display is selected) of the display. These voltages are capacitively coupled directly to the pixel electrodes of the display, and this coupling may be quite strong in a field-shielded pixel design. Even if these coupled voltage spikes are, over the long term, constrained to be DC balanced, continuous application of these voltage spikes may result in changes in the optical state of the pixels.

It is known that these voltage spikes, and the problems resulting therefrom, can be reduced by providing a pixel storage capacitor coupled to each pixel electrode; see, for example, the aforementioned 2002/0106847. In the prior art, essentially the only practicable way to minimize or eliminate the effects of these voltage spikes is to increase the size of the pixel storage capacitor, which increases the power consumption of the display considerably. In addition, the large size of the storage capacitor limits the maximum achievable resolution, and may result in a decrease in panel yield by increasing the area of metal-metal overlap.

It has now been realized that the problems discussed above can be reduced or eliminated by using, in an active matrix electro-optic display, an electro-optic medium that exhibits a voltage threshold, i.e., a medium which essentially does not switch when subjected to a low but non-zero voltage.

SUMMARY OF THE INVENTION

In one aspect, this invention provides an electrophoretic medium comprising an electrically charged particle suspended in a suspending fluid, the particle having a polymeric shell having repeating units derived from at least one monomer the homopolymer of which is incompatible with the suspending fluid.

This aspect of the present invention may hereinafter for convenience be called the "incompatible monomer medium". In such a medium, the polymeric shell desirably further comprises repeating units derived from at least one monomer the homopolymer of which is compatible with the suspending fluid. The monomer or monomers forming the compatible homopolymer (these monomers may hereinafter for convenience by called the "compatible monomers") may comprise from about 15 to about 99 percent, and preferably about 50 to about 99 percent, by weight of the polymer shell. The suspending fluid is typically a hydrocarbon, although a mixture of a hydrocarbon and another compatible solvent, such as a halocarbon, may be used. Alternatively, a silicone fluid or a fluorocarbon can be used as the suspending fluid.

The monomer forming the incompatible homopolymer (this monomer may hereinafter for convenience be called the "incompatible monomer"). It will be appreciated that whether a particular monomer can be considered an incompatible monomer depends upon the specific suspending fluid being used, and that a specific monomer may be an incompatible monomer in one suspending fluid and a compatible monomer in a different suspending fluid. For example, lauryl methacrylate is a compatible monomer in aliphatic hydrocarbon suspending fluids, but would normally be an incompatible monomer in a silicone suspending fluid.

For a medium comprised solely or largely of hydrocarbons, the incompatible monomer may be any one or more of acrylates and methacrylates formed from alcohols containing not more than about eight carbon atoms, said alcohols optionally containing hydroxyl or halogen or other polar substitutents, such as carboxyl groups, cyano groups, ketone or aldehyde groupings; acrylamides and methacrylamides; N,N-dialkylacrylamides; N-vinylpyrrolidone; styrene and derivatives thereof, vinyl esters; and vinyl halides. Specific examples of incompatible monomers include methyl methacrylate, ethyl methacrylate, butyl methacrylate, isobutyl methacrylate, t-butyl methacrylate, octyl methacrylate, 2-ethylhexyl methacrylate, 2-hydroxyethyl methacrylate, acrylamide, acrylic acid, acrylonitrile, methyl vinyl ketone, methacrylamide, N-vinylpyrrolidone, styrene, vinyl acetate, vinyl chloride, and vinylidene chloride. Further examples of incompatible monomers include fluorine-containing esters of acrylic acid and methacrylic acid, such as trifluoroethyl methacrylate, hexafluorobutyl acrylate, or other kinds of fluorinated monomers, such as pentafluorostyrene or other polyfluoroaromatic molecules containing a polymerizable functional group. Other classes of incompatible monomers in hydrocarbon media include silicone-containing molecules that include polymerizable vinyl groups in their structure. In a specific hydrocarbon medium of the invention described in the Examples below, the compatible monomer comprises lauryl methacrylate and the incompatible monomer comprises any one or more of trifluoroethyl methacrylate, hexafluorobutyl acrylate, styrene, t-butyl methacrylate and N-vinylpyrrolidone.

With other types of suspending fluid, for example, fluorocarbon media, many of the above types of incompatible monomers can be used, together with a major proportion of a fluorocarbon monomer as the compatible monomer. Similarly, for silicone suspending fluids, the compatible monomer may comprise a majority of silicone groups, and the incompatible monomer may comprise any of the monomers listed above except those comprising a majority of silicone functionality.

The incompatible monomer medium may further comprise a second type of electrically charged particle having at least one optical characteristic differing from that of the other (first) electrically charged particle or particles, the second type of electrically charged particle having a polymeric shell. In one form of such a two-particle system, the first electrically charged particle comprises titania and the second type of electrically charged particle comprises carbon black or copper chromite.

This invention also provides an electrophoretic particle for use in the incompatible monomer medium of the present invention. In an electrophoretic medium using a hydrocarbon or halocarbon as a suspending fluid, this electrophoretic particle (hereinafter for convenience called "the incompatible monomer particle") comprises a pigment particle having a polymeric shell having repeating units derived from at least one monomer the homopolymer of which is incompatible with n-hexane. (As will be apparent to those skilled in the technology of electrophoretic media, the hydrocarbon suspending fluids typically used in such media comprise various mixtures of low molecular weight aliphatic hydrocarbons, and for the avoidance of ambiguity, n-hexane may be used as a single test compound for testing compatibility with such hydrocarbon mixtures.)

In the incompatible monomer particle of the present invention, the polymeric shell may further comprise repeating units derived from at least one monomer the homopolymer of which is compatible with n-hexane. The compatible monomer may comprise from about 15 to about 99 percent, and preferably about 50 to about 99 percent, by weight of the polymer shell. The incompatible monomer may comprise any one or more of those listed in Paragraph 56 above. In specific particles of the invention described in the Examples below, the compatible monomer comprises lauryl methacrylate and the incompatible monomer comprises any one or more of styrene, t-butyl methacrylate and N-vinylpyrrolidone. The pigment used to form the particle of the present invention may be, for example, any one or more of titania, carbon black and copper chromite.

In another aspect, this invention provides similar electrophoretic particles for use in fluorinated and silicone-based suspending fluids. Thus, this invention provides an electrophoretic particle comprising a pigment particle having a polymeric shell having repeating units derived from at least one monomer the homopolymer of which is incompatible with perfluorodecalin. This invention also provides an electrophoretic particle comprising a pigment particle having a polymeric shell having repeating units derived from at least one monomer the homopolymer of which is incompatible with polydimethylsiloxane 200, viscosity 0.65 centistokes.

In another aspect, this invention provides an electrophoretic medium comprising:
  a suspending fluid;
  a first type of electrically charged particle suspended in the suspending fluid, the first type of particle having a first optical characteristic and a polymeric shell; and
  a second type of electrically charged particle suspended in the suspending fluid, the second type of particle having a second optical characteristic differing from the first optical characteristic, and a polymeric shell;
  wherein the polymeric shells are arranged such that homoaggregation of the first and second types of particles is thermodynamically favored over heteroaggregation.

This medium may hereinafter for convenience be called the "homoaggregation medium" of the present invention. It will be understood that there is a considerable overlap between the dual particle incompatible monomer media of the present invention and the homoaggregation media, in the sense that many media can satisfy the definitions of both simultaneously.

In the homoaggregation media of the present invention, the polymeric shells of the first and second types of particles may each comprise repeating units derived from at least one monomer the homopolymer of which is incompatible with the suspending fluid. Each polymeric shell may further comprise repeating units derived from at least one monomer the homopolymer of which is compatible with the suspending fluid. The compatible monomer may comprise from about 15 to about 99 percent, and preferably about 50 to about 99 percent, by weight of the polymer shell. The suspending fluid may have a dielectric constant less than about 5, and may comprise a hydrocarbon, preferably an aliphatic hydrocarbon. Alternatively, the suspending fluid may comprise an aryl-alkane or dodecylbenzene.

Also, the incompatible monomer may comprise any one of more of those listed in Paragraph 56 above. In a preferred from of homoaggregation medium, the compatible monomer comprises lauryl methacrylate and the incompatible monomer comprises any one or more of styrene, t-butyl methacrylate and N-vinylpyrrolidone.

For reasons explained in detail below, the homoaggregation medium of the invention may have an operating voltage threshold. The medium may be encapsulated, i.e., the suspending fluid and the particles may be retained within a plurality of capsules or cells.

The present invention also provides an electrophoretic display comprising either type of electrophoretic medium of the invention and at least one electrode disposed adjacent the electrophoretic medium and arranged to apply an electric field thereto.

This invention also provides an active matrix electro-optic display comprising a layer of electro-optic medium; and a plurality of pixel electrodes disposed adjacent the layer of electro-optic medium and arranged to apply an electric field thereto, wherein the electro-optic medium exhibits a voltage threshold.

This electro-optic display may hereinafter for convenience be called the "voltage threshold display" of the present invention. In such a display, a capacitor may be associated with each pixel electrode. The electro-optic medium may comprise a plurality of charged particles suspended in a suspending fluid and capable of moving therethrough on application of an electric field to the electro-optic medium. These charged particles may have polymeric shells having repeating units derived from at least one monomer the homopolymer of which is incompatible with the suspending fluid. The electro-optic medium may also be a homoaggregation medium of the present invention.

Finally, this invention provides a process for producing a polymer-coated pigment particle, this process comprising:

(a) reacting the pigment particle with a reagent having a functional group capable of reacting with, and bonding to, the particle, and also having a polymerizable or polymerization-initiating group, thereby causing the functional group to react with the particle surface and attach the polymerizable group thereto; and (b) reacting the product of step (a) with at least one monomer or oligomer under conditions effective to cause reaction between the polymerizable or polymerization-initiating group on the particle and the at least one monomer or oligomer, thereby causing the formation of polymer bonded to the pigment particle, wherein step (b) is carried out in an aliphatic hydrocarbon.

This process may hereinafter for convenience be called the "aliphatic polymerization process" of the present invention.

BRIEF DESCRIPTION OF DRAWINGS

FIGS. 1A and 1B are schematic cross-sections through a first electrophoretic display of the present invention in which the electrophoretic medium comprises a single type of particle in a colored suspending fluid.

FIGS. 3A and 3B are schematic cross-sections, generally similar to those of FIGS. 2A and 2B respectively through a third electrophoretic display of the present invention in which the electrophoretic medium comprises two different types of particle, bearing charges of the same polarity but differing in electrophoretic mobility, in an uncolored suspending fluid.

DETAILED DESCRIPTION

Figure 2A:
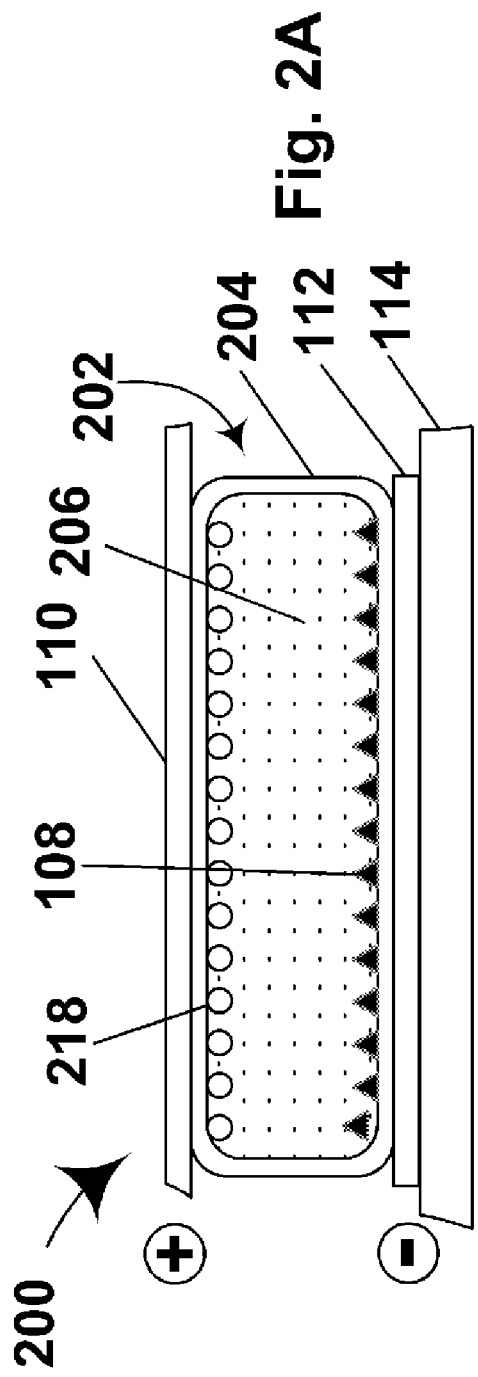
FIGS. 2A and 2B are schematic cross-sections, generally similar to those of FIGS. 1A and 1B respectively through a second electrophoretic display of the present invention in which the electrophoretic medium comprises two different types of particle, bearing charges of opposite polarity, in an uncolored suspending fluid.

As already indicated, the present invention relates to electrophoretic media using particles having polymeric shells, electrophoretic particles for use in such media, electrophoretic displays containing such media or similar electro-optic media, and processes for the preparation of the aforementioned polymeric shells. Accordingly, before describing the various aspects of the present invention in detail, it is believed desirable to provide a general introduction regarding electrophoretic particles, processes for forming polymer shells thereon, the electrophoretic media and display incorporating such particles.

General Introduction

The electrophoretic medium of the present invention may be of any of the types described in the aforementioned E Ink and MIT patents and applications, and preferred embodiments of such media will now be described with reference to FIGS. 1 to 4 of the accompanying drawings.

The first electrophoretic display (generally designed 100) of the invention shown in FIGS. 1A and 1B comprises an encapsulated electrophoretic medium (generally designated 102) comprising a plurality of capsules 104 (only one of which is shown in FIGS. 1A and 1B), each of which contains a suspending liquid 106 and dispersed therein a plurality of a single type of particle 108, which for purposes of illustration will be assumed to be black. The particles 108 are electrophoretically mobile and may be formed of carbon black. In the following description, it will be assumed that the particles 108 are positively charged, although of course negatively charged particles could also be used if desired. (The triangular shape of the particles 108, and the square and circular shapes of other particles discussed below, are used purely to way of illustration to enable the various types of particles to be distinguished easily in the accompanying drawings, and in no way correspond to the physical forms of the actual particles, which are typically substantially spherical. However, we do not exclude the use of non-spherical particles in the present displays.) The display 100 further comprises a common, transparent front electrode 110, which forms a viewing surface through which an observer views the display 100, and a plurality of discrete rear electrodes 112, each of which defines one pixel of the display 100 (only one rear electrode 112 is shown in FIGS. 1A and 1B). For ease of illustration and comprehension, FIGS. 1A and 1B show only a single microcapsule forming the pixel defined by rear electrode 112, although in practice a large number (20 or more) microcapsules are normally used for each pixel. The rear electrodes 112 are mounted upon a substrate 114.

The suspending liquid 106 is colored such that the particles 108 lying in the positions shown in FIG. 1A adjacent the rear electrodes 112 are not visible to an observer viewing the display 100 via the front electrode 110. The necessary color in the suspending liquid 106 may be provided by dissolving a dye in the liquid. Since the colored suspending liquid 106 and the particles 108 render the electrophoretic medium 102 opaque, the rear electrodes 112 and the substrate 114 can be transparent or opaque since they are not visible through the opaque electrophoretic medium 102.

The capsules 104 and the particles 108 can be made in a wide range of sizes. However, in general it is preferred that the thickness of the capsules, measured perpendicular to the electrodes, be in the range of about 15 to 500 µm, while the particles 108 will typically have diameters in the range of about 0.25 to about 2 µm.

FIG. 1A shows the display 100 with the rear electrode 112 negatively charged and the front electrode 110 positively charged. Under this condition, the positively-charged particles 108 are attracted to the negative rear electrode 112 and thus lie adjacent the rear electrode 112, where they are hidden from an observer viewing the display 100 through the front electrode 110 by the colored liquid 106. Accordingly, the pixel shown in FIG. 1A displays to the observer the color of the liquid 106, which for purposes of illustration will be assumed to be white. (Although the display 100 is illustrated in FIGS. 1A and 1B with the rear electrodes 112 at the bottom, in practice both the front and rear electrodes are typically disposed vertically for maximum visibility of the display 100. In general, the media and displays of the invention described herein do not rely in any way upon gravity to control the movement of the particles; such movement under gravity is in practice far too slow to be useful for controlling particle movement.)

FIG. 1B shows the display 100 with the front electrode 110 made negative relative to the rear electrode 112. Since the particles 108 are positively charged, they will be attracted to the negatively-charged front electrode 110, and thus the particles 108 move adjacent the front electrode 110, and the pixel displays the black color of the particles 108.

In FIGS. 1A and 1B, the capsules 104 are illustrated as being of substantially prismatic form, having a width (parallel to the planes of the electrodes) significantly greater than their height (perpendicular to these planes). This prismatic shape of the capsules 104 is deliberate. If the capsules 104 were essentially spherical, in the black state shown in FIG. 1B, the particles 108 would tend to gather in the highest part of the capsule, in a limited area centered directly above the center of the capsule. The color seen by the observer would then be essentially the average of this central black area and a white annulus surrounding this central area, where the white liquid 106 would be visible. Thus, even in this supposedly black state, the observer would see a grayish color rather than a pure black, and the contrast between the two extreme optical states of the pixel would be correspondingly limited. In contrast, with the prismatic form of microcapsule shown in FIGS. 1A and 1B, the particles 108 cover essentially the entire cross-section of the capsule so that no, or at least very little white liquid is visible, and the contrast between the extreme optical states of the capsule is enhanced. For further discussion on this point, and on the desirability of achieving close-packing of the capsules within the electrophoretic layer, the reader is referred to the aforementioned U.S. Pat. No. 6,067,185, and the corresponding published International Application WO 99/10767. Also, as described in the aforementioned E Ink and MIT patents and applications, to provide mechanical integrity to the electrophoretic medium, the microcapsules are normally embedded within a solid binder, but this binder is omitted from FIGS. 1 to 3 for ease of illustration.

Figure 2B:
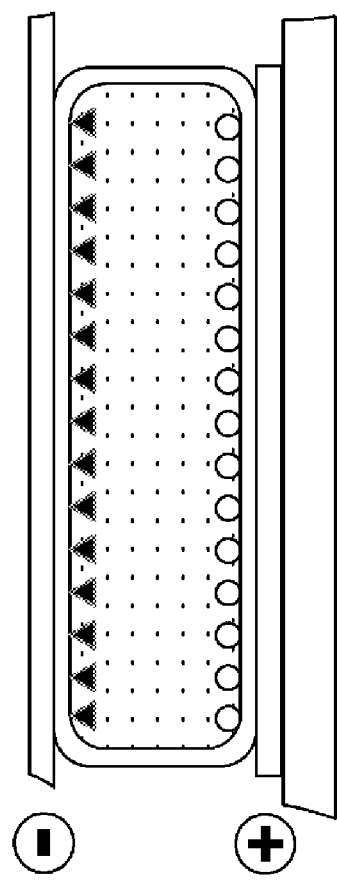

The second electrophoretic display (generally designed 200) of the invention shown in FIGS. 2A and 2B comprises an encapsulated electrophoretic medium (generally designated 202) comprising a plurality of capsules 204, each of which contains a suspending liquid 206 and dispersed therein a plurality of positively charged black particles 108 identical discussed to those in the first display 100 discussed above. The display 200 further comprises a front electrode 110, rear electrodes 112, and a substrate 114, all of which are identical to the corresponding integers in the first display 100. However, in addition to the black particles 108, there are suspended in the liquid 206 a plurality of negatively charged, particles 218, which for present purposes will be assumed to be white.

Typically the liquid 206 is uncolored (i.e., essentially transparent), although some color may be present therein to adjust the optical properties of the various states of the display. FIG. 2A shows the display 200 with the front electrode 110 positively charged relative to the rear electrode 112 of the illustrated pixel. The positively charged particles 108 are held electrostatically adjacent the rear electrode 112, while the negatively charged particles 218 are held electrostatically against the front electrode 110. Accordingly, an observer viewing the display 200 through the front electrode 110 sees a white pixel, since the white particles 218 are visible and hide the black particles 108.

FIG. 2B shows the display 200 with the front electrode 110 negatively charged relative to the rear electrode 112 of the illustrated pixel. As in the corresponding optical state shown in FIG. 1B, the positively charged particles 108 are now electrostatically attracted to the negative front electrode 110, while the negatively charged particles 218 are electrostatically attracted to the positive rear electrode 112. Accordingly, the particles 108 move adjacent the front electrode 110, and the pixel displays the black color of the particles 108, which hide the white particles 218.

The third electrophoretic display (generally designated 300) of the invention shown in FIGS. 3A and 3B comprises an encapsulated electrophoretic medium (generally designated 302) comprising a plurality of capsules 304. The display 300 further comprises a front electrode 110, rear electrodes 112, and a substrate 114, all of which are identical to the corresponding integers in the displays 100 and 200 previously described. The display 300 resembles the display 200 described above in that the liquid 306 is uncolored and that white negatively charged particles 218 are suspended therein. However, that the display 300 differs from the display 200 by the presence of red negatively charged particles 320, which have a substantially lower electrophoretic mobility than the white particles 218.

FIG. 3A shows the display 300 with the front electrode 110 positively charged relative to the rear electrode 112 of the illustrated pixel. Both the negatively charged white particles 218 and the negatively charged red particles 320 are attracted to the front electrode 110, but since the white particles 218 have substantially higher electrophoretic mobility, that they reach the front electrode 110 first (note that the optical state shown in FIG. 3A is normally generated by abruptly reversing the polarity off the electrodes in the optical state shown in FIG. 3B, thus forcing both the white particles 218 and the red particles 320 to traverse the thickness of the capsule 304, and thus allowing the greater mobility of the white particles 218 to cause them to reach their positions adjacent the front electrode 110 before the red particles 320). Thus, the white particles 218 form a continuous layer immediately adjacent the front electrode 110, thereby hiding the red particles 320. Accordingly, an observer viewing the display 300 through the front electrode 110 sees a white pixel, since the white particles 218 are visible and hide the red particles 320.

FIG. 3B shows the display 300 with the front electrode 110 negatively charged relative to the rear electrode 112 of the illustrated pixel. Both the negatively charged white particles 218 and the negatively charged red particles 320 are attracted to the rear electrode 112, but since the white particles have higher electrophoretic mobility, when the optical state shown in FIG. 3B is produced by reversing the polarity on the electrodes in the optical state shown in FIG. 3A, the white particles 218 reach the rear electrode 112 more quickly than do the red particles 320, so that the white particles 218 form a continuous layer adjacent the electrode 112, leaving a continuous layer of the red particles 320 facing the front electrode 110. Accordingly, an observer viewing the display 300 through the front electrode 110 sees a red pixel, since the red particles 320 are visible and hide the white particles 218.

Figure 4A:
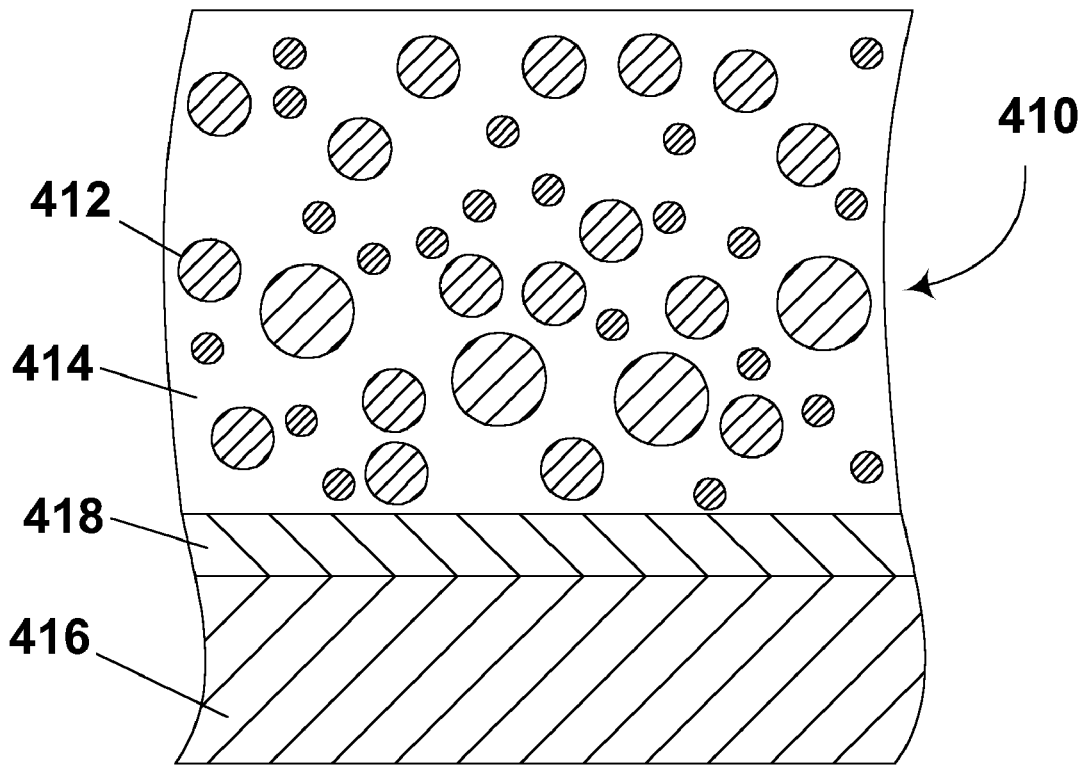
FIGS. 4A and 4B illustrate a polymer-dispersed electrophoretic medium of the present invention and the process used to produce this medium.
Figure 4B:
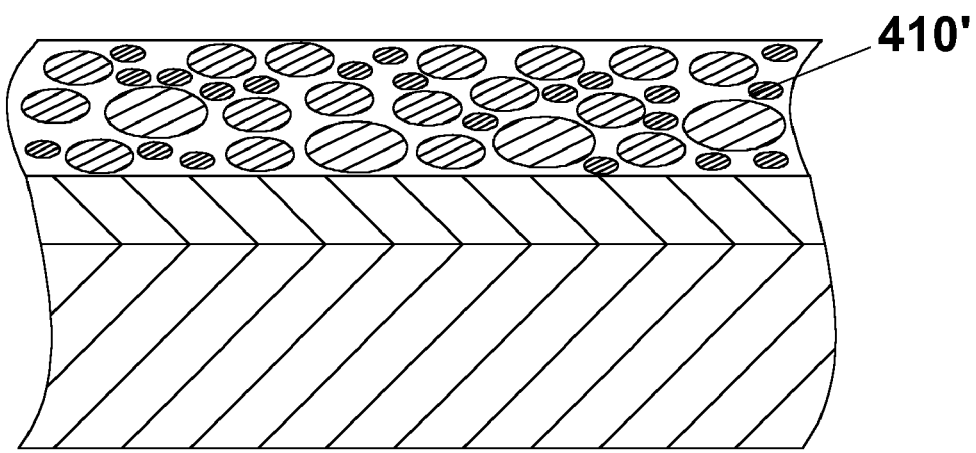

FIGS. 4A and 4B illustrate a polymer-dispersed electrophoretic medium of the present invention and the process used to produce this medium. This polymer-dispersed medium contains non-spherical droplets and is prepared by using a film-forming material which produces a film capable of being shrunk substantially after its formation. The preferred discontinuous phase for this purpose is gelatin, although other proteinaceous materials, and possibly cross-linkable polymers may alternatively be employed. A mixture of the liquid material (which will eventually form the continuous phase) and the droplets is formed and coated on to a substrate to form a structure as illustrated in FIG. 4A. FIG. 4A shows a layer 410 comprising droplets 412 dispersed in a liquid medium 414 which is in the process of forming a film, this layer 410 having been coated on a substrate 416 (preferably a flexible polymeric film, such as a polyester film) previously provided with a layer 418 of a transparent electrically conductive material, such as indium-tin oxide. The liquid material forms a relatively thick layer 410 containing essentially spherical droplets 412; as shown in FIG. 4A. After the layer 410 has formed a solid continuous phase, the layer is then allowed to dry, preferably at about room temperature (although the layer may be heated if desired) for a period sufficient to dehydrate the gelatin, thus causing substantial reduction in the thickness of the layer and producing the type of structure illustrated in FIG. 4B, the dried and shrunken layer being designated 410' in FIG. 4B. The vertical shrinkage of the layer (i.e., the shrinkage perpendicular to the surface of the substrate 416) in effect compresses the original spherical droplets into oblate ellipsoids whose thickness perpendicular to the surface is substantially smaller than their lateral dimensions parallel to the surface. In practice, the droplets are normally sufficiently closely packed that the lateral edges of adjacent droplets contact each other, so that the final forms of the droplets more closely resemble irregular prisms than oblate ellipsoids. Also as shown in FIG. 4B, more than one layer of droplets may be present in the final medium. When the medium is of the type shown in FIG. 4B in which the droplets are polydisperse (i.e., a wide range of droplet sizes are present), the presence of such multiple layers is advantageous in that it reduces the chance that small areas of the substrate will not be covered by any droplet; hence the multiple layers help to ensure that the electrophoretic medium is completely opaque and that no part of the substrate is visible in a display formed from the medium. However, in a medium using essentially monodisperse droplets (i.e., droplets all of substantially the same size), it will generally be advisable to coat the medium in a layer which, after shrinkage, will produce a close-packed monolayer of droplets, cf. the aforementioned 2003/0137717. Because they lack the relatively rigid microcapsule walls found in microencapsulated electrophoretic media, the droplets in polymer-dispersed media of the present invention may tend to pack more tightly into a close-packed monolayer than do microcapsules.

Contrary to what might be expected, experimentally it has been found that the droplets do not coalesce during the drying of the medium. However, we do not exclude the possibility that, in certain embodiments of the invention some rupturing of the walls between adjacent capsules might occur, thus providing a partial connection between droplets.

The degree of deformation of the droplets which occurs during the drying step, and hence the final forms of the droplets, may be varied by controlling the proportion of water in the gelatin solution and the ratio of this solution to the droplets. For example, experiments were conducted using gelatin solutions of from 2 to 15 percent by weight, and using 200 grams of each gelatin solution and 50 grams of the internal non-aqueous phase which forms the droplets. To produce a final layer of electrophoretic medium 30 μm in thickness, it was necessary to coat a layer of the 2 percent gelatin solution/internal phase mixture 139 μm in thickness; upon drying, this layer produced an electrophoretic medium 30 μm in thickness containing 92.6 percent by volume of droplets. On the other hand, to produce the same final thickness of electrophoretic medium, the 15 percent gelatin solution/internal phase mixture was coated at a thickness of 93 μm, and upon drying produced an electrophoretic medium containing 62.5 percent by volume of droplets. The medium produced from the 2 percent gelatin solution was weaker than is desirable to withstand robust handling; media produced from gelatin solutions containing from 5 to 15 percent by weight of gelatin had satisfactory mechanical properties.

The degree of deformation of the droplets in the final electrophoretic medium is also affected by the initial size of the droplets, and the relationship between this initial size and the thickness of the final layer of electrophoretic medium. Experiments indicate that the larger the average initial size of the droplets and/or the larger the ratio of this average initial size to the thickness of the final layer, the greater is the deformation of the droplets from a spherical shape in the final layer. In general, it is preferred that the average initial size of the droplets be from about 25 percent to about 400 percent of the thickness of the final layer. For example, in the experiments previously described, in which the thickness of the final layer was 30 µm, good results were obtained with an initial average droplet size of 10 to 100 µm.

Gelatin forms a film by a sol/gel transformation, but the present invention is not restricted to film-forming materials which form their films by such sol/gel transformation. For example, the formation of the film may be accomplished by the polymerization of a monomer or oligomer, by the cross-linking of a polymer or oligomer, by radiation-curing of a polymer or by any other known film-forming process. Similarly, in the preferred variant of the invention in which the film is first formed and then caused to shrink in thickness, this shrinkage need not accomplished by the same type of dehydration mechanism by which a gelatin film shrinks, but may be accomplished by removal of a solvent, aqueous or non-aqueous, from the film, cross-linking of a polymeric film or any other conventional procedure.

In a polymer-dispersed electrophoretic medium of the present invention, the droplets desirably comprise at least about 40 percent, and preferably about 50 to about 80 percent, by volume of the electrophoretic medium; see the aforementioned 2002/0131147. It should be stressed that the droplets used in the polymer-dispersed media of the present invention may have any of the combinations of particles and suspending fluids illustrated in FIGS. 1 to 3.

The present invention may be applied to any of the forms of encapsulated electrophoretic media shown in FIGS. 1 to 4. However, the present invention is not restricted to encapsulated and polymer-dispersed electrophoretic media, and may also be applied to unencapsulated media.

Various considerations in the production of electrophoretic particles of the present invention will now be considered:

Types of Particles and Pre-treatment Thereof

The "base particle" (i.e., the particle which is provided with a polymer shell in accordance with various aspects of the present invention) may be of any of the types previously used in electrophoretic displays, and there is much flexibility in the choice of such particles. For purposes of this invention, a particle is any component that is charged or capable of acquiring a charge (i.e., has or is capable of acquiring electrophoretic mobility), and, in some cases, this mobility may be zero or close to zero (i.e., the particles will not move). The particles may be, for example, neat pigments or dyed (laked) pigments, or any other component that is charged or capable of acquiring a charge. Typical considerations for the electrophoretic particle are its optical properties, electrical properties, and surface chemistry. The particles may be organic or inorganic compounds, and they may either absorb light or scatter light. The particles for use in the invention may further include scattering pigments, absorbing pigments and luminescent particles. The particles may be retroreflective, such as corner cubes, or they may be electroluminescent, such as zinc sulfide particles, which emit light when excited by an AC field, or they may be photoluminescent. Zinc sulfide electroluminescent particles may be encapsulated with an insulative coating to reduce electrical conduction.

The electrophoretic particle is usually a pigment, a laked pigment, or some combination of the above. A neat pigment can be any pigment, and, usually for a light colored particle, pigments such as rutile (titania), anatase (titania), barium sulfate, kaolin, or zinc oxide are useful. Some typical particles have high refractive indices, high scattering coefficients, and low absorption coefficients. Other particles are absorptive, such as carbon black or colored pigments used in paints and inks. The pigment should also be insoluble in the suspending fluid. Yellow pigments such as diarylide yellow, Hansa yellow, and benzidin yellow have also found use in similar displays. Any other reflective material can be employed for a light colored particle, including non-pigment materials, such as metallic particles.

Useful neat pigments include, but are not limited to, $PbCrO_4$, Cyan blue GT 55-3295 (American Cyanamid Company, Wayne, N.J.), Cibacron Black BG (Ciba Company, Inc., Newport, Del.), Cibacron Turquoise Blue G (Ciba), Cibalon Black BGL (Ciba), Orasol Black BRG (Ciba), Orasol Black RBL (Ciba), Acetamine Black, CBS (E. I. du Pont de Nemours and Company, Inc., Wilmington, Del., hereinafter abbreviated "du Pont"), Crocein Scarlet N Ex (du Pont) (27290), Fiber Black VF (du Pont) (30235), Luxol Fast Black L (du Pont) (Solv. Black 17), Nirosine Base No. 424 (du Pont) (50415 B), Oil Black BG (du Pont) (Solv. Black 16), Rotalin Black RM (du Pont), Sevron Brilliant Red 3 B (du Pont); Basic Black DSC (Dye Specialties, Inc.), Hectolene Black (Dye Specialties, Inc.), Azosol Brilliant Blue B (GAF, Dyestuff and Chemical Division, Wayne, N.J.) (Solv. Blue 9), Azosol Brilliant Green BA (GAF) (Solv. Green 2), Azosol Fast Brilliant Red B (GAF), Azosol Fast Orange RA Conc. (GAF) (Solv. Orange 20), Azosol Fast Yellow GRA Conc. (GAF) (13900 A), Basic Black KMPA (GAF), Benzofix Black CW-CF (GAF) (35435), Cellitazol BNFV Ex Soluble CF (GAF) (Disp. Black 9), Celliton Fast Blue AF Ex Conc (GAF) (Disp. Blue 9), Cyper Black IA (GAF) (Basic Black 3), Diamine Black CAP Ex Conc (GAF) (30235), Diamond Black EAN Hi Con. CF (GAF) (15710), Diamond Black PBBA Ex (GAF) (16505); Direct Deep Black EA Ex CF (GAF) (30235), Hansa Yellow G (GAF) (11680); Indanthrene Black BBK Powd. (GAF) (59850), Indocarbon CLGS Conc. CF (GAF) (53295), Katigen Deep Black NND Hi Conc. CF (GAF) (15711), Rapidogen Black 3 G (GAF)(Azoic Black 4); Sulphone Cyanine Black BA-CF (GAF) (26370), Zambezi Black VD Ex Conc. (GAF) (30015); Rubanox Red CP-1495 (The Sherwin-Williams Company, Cleveland, Ohio) (15630); Raven 11 (Columbian Carbon Company, Atlanta, Ga.), (carbon black aggregates with a particle size of about 25 µm), Statex B-12 (Columbian Carbon Co.) (a furnace black of 33 µm average particle size), Greens 223 and 425 (The Shepherd Color Company, Cincinnati, Ohio 45246); Blacks 1, 1G and 430 (Shepherd); Yellow 14 (Shepherd); Krolor Yellow KO-788-D (Dominion Colour Corporation, North York, Ontario; "KROLOR" is a Registered Trade Mark); Red Synthetic 930 and 944 (Alabama Pigments Co., Green Pond, Ala. 35074), Krolor Oranges KO-786-D and KO-906-D (Dominion Colour Corporation); Green GX (Bayer); Green 56 (Bayer); Light Blue ZR (Bayer); Fast Black 100 (Bayer); Bayferrox 130M (Bayer "BAYFER-ROX" is a Registered Trade Mark); Black 444 (Shepherd); Light Blue 100 (Bayer); Light Blue 46 (Bayer); Yellow 6000 (First Color Co., Ltd., 1236-1, Jwungwang-dong, Shihung, Kyounggi-do, Korea), Blues 214 and 385 (Shepherd); Violet 92 (Shepherd); and chrome green.

Particles may also include laked, or dyed, pigments. Laked pigments are particles that have a dye precipitated on them or which are stained. Lakes are metal salts of readily soluble anionic dyes. These are dyes of azo, triphenylmethane or anthraquinone structure containing one or more sulphonic or carboxylic acid groupings. They are usually precipitated by a calcium, barium or aluminum salt onto a substrate. Typical examples are peacock blue lake (CI Pigment Blue 24) and Persian orange (lake of CI Acid Orange 7), Black M Toner (GAF) (a mixture of carbon black and black dye precipitated on a lake).

A dark particle of the dyed type may be constructed from any light absorbing material, such as carbon black, or inorganic black materials. The dark material may also be selectively absorbing. For example, a dark green pigment may be used.

The optical purpose of the particle may be to scatter light, absorb light, or both. Useful sizes may range from 1 nm up to about 100 μm. The density of the electrophoretic particle may be substantially matched to that of the suspending (i.e., electrophoretic) fluid. As defined herein, a suspending fluid has a density that is "substantially matched" to the density of the particle if the difference in their respective densities is between about zero and about two grams/milliliter ("g/ml"). This difference is preferably between about zero and about 0.5 g/ml.

New and useful electrophoretic particles may still be discovered, but a number of particles already known to those skilled in the art of electrophoretic displays and liquid toners can also prove useful.

The presently preferred materials for forming light-colored electrophoretic particles are metal oxides (and/or hydroxides), especially titania. The titania particles may be coated with an oxide, such as alumina or silica, for example; the presence of such coatings appears to improve the stability of the titania in electrophoretic media, presumably by suppressing reactions, such as photochemical reactions, which may occur at the interface between a bare titania surface and the suspending fluid. The titania particles may have one, two, or more layers of metal-oxide coating. For example, a titania particle for use in electrophoretic displays of the invention may have a coating of alumina and/or a coating of silica. The coatings may be added to the particle in any order. One particle that has been shown to be useful comprises titania having a silica/alumina coating, which appears to contain discrete areas of silica and alumina. Such a coated titania is commercially available from E. I. du Pont de Nemours and Company, Wilmington, Del., under the trade name R960. It will be appreciated that since, in such coated particles, the coating completely covers the titania, any reagent used to attach an initiator or polymerizable group to the surface of the particle must react with the coating, and need not be capable of reacting with titania. Indeed, it is one important advantage of the present invention that, since techniques for forming silica and/or alumina coatings on pigments are described in the literature (see, for example, U.S. Pat. No. 3,639,133 regarding silica coatings), and, as illustrated below, such techniques may readily be adapted to produce coatings on a wide variety of materials, the present processes can readily be adapted to utilize any of these materials by first providing a silica and/or alumina coating thereon. Once the coating has been applied, the remaining steps in forming the polymer-coated particles are essentially similar, since the reagents used "see" only the coating, so that the chemical process steps are essentially independent of the chemical nature of the pigment underlying the silica coating.

The aforementioned 2002/0185378 describes a preferred technique for forming silica coatings on particles which do not already possess such coatings. Typically, in previous processes such as those described in the aforementioned U.S. Pat. No. 3,639,133, the silica coated pigment is separated from the reaction mixture in which it is produced (this reaction mixture having a pH of about 9.5 to 10), then washed and dried, for example at 80° C. This tends to result is pigment particles which are fused together by their silica coatings. This fusion or aggregation makes it extremely difficult to redisperse the pigment into its primary particulate form without using a harsh treatment such as attrition, ball milling or homogenization, and such harsh treatment may fracture the silica coating, thus lowering the number of reactive sites on the pigment particle at which polymer chains can be formed.

The aforementioned 2002/0185378 describes a process in which, after the deposition of the silica coating is completed, the pH of the reaction mixture is reduced below about 4, and preferably to about 3, before the silica-coated particles are separated from the reaction mixture; this process essentially eliminates the tendency for the particles to fuse together. The necessary reduction in pH is conveniently effected using sulfuric acid, although other acids, for example, nitric, hydrochloric and perchloric acids, may be used. The particles are conveniently separated from the reaction mixture by centrifugation. Following this separation, it is not necessary to dry the particles. Instead, the silica-coated particles can be readily re-dispersed in the medium, typically an aqueous alcoholic medium, to be used for the next step of the process for the formation of polymer on the particles. This enables the silica-coated pigment particles to be maintained in a non-agglomerated and non-fused form as they are subjected to the processes for attachment of polymerizable or polymerization-initiating groups, thus allowing for thorough coverage of the pigment particle with such groups, and preventing the formation of large aggregates of pigment particles in the microcapsules which will typically eventually be formed from the silica-coated pigment. Preventing the formation of such aggregates is especially important when the silica-coated pigment is to be used in small microcapsules (less than about 100 μm in diameter), and such small microcapsules are desirable since they reduce the operating voltage and/or switching time of the electrophoretic medium. Also, eliminating the drying procedures previously used in forming silica-coated pigments substantially reduces the processing time required.

The presently preferred materials for forming dark-colored electrophoretic particles are carbon black, for example the material sold commercially by Degussa AG, Düsseldorf, Germany under the trade name Printex A, and copper chromite, sold as the aforementioned Shepherd Black 1G.

The processes used to provide polymer shells on electrophoretic particles can vary widely, and a summary of the numerous possible variations in such processes will now be given.

Figure 5A:
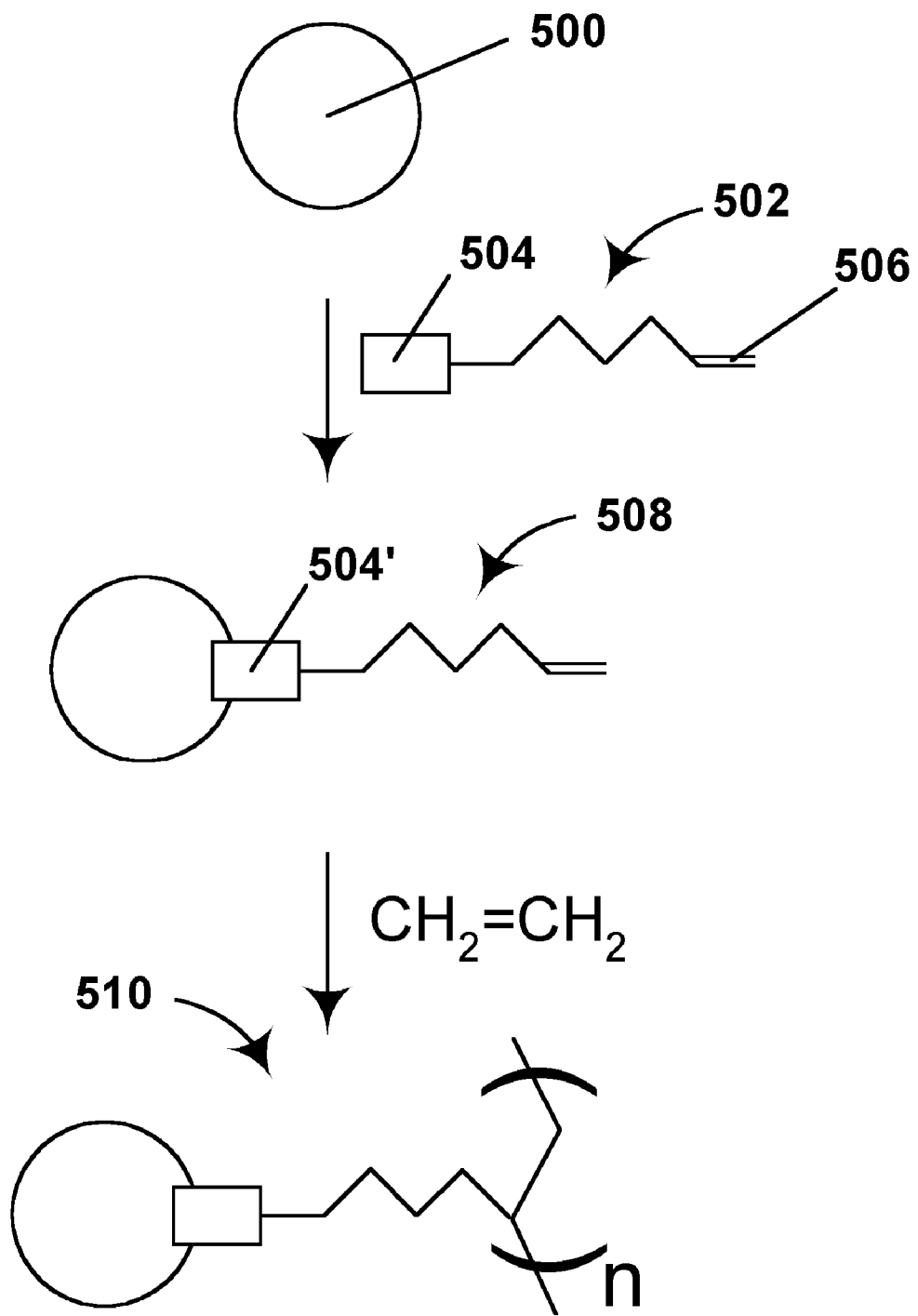
FIGS. 5A, 5B and 5C are reaction schemes summarizing some of the processes used in the present invention to apply polymer coating to pigment particles.

In a first process described in the aforementioned 2002/0185378 (hereinafter called the "random graft polymerization" or "RGP" process), as illustrated in FIG. 5A, a particle 500 is reacted with a reagent 502 having a functional group 504 capable of reacting with, and bonding to, the particle and with a polymerizable group, for example a pendant vinyl or other ethylenically unsaturated group 506. (The shapes used to indicate the functional group 504 and other functional groups discussed below are used only to make it easier to illustrate the reactions involved and, of course, bear no relationship to the actual physical shapes of the functional groups.) The functional group reacts 504 with the particle surface, leaving a residue indicated at 504' attached to the particle and also leaving the polymerizable group 506 covalently bonded to the particle surface and free to participate in a subsequent polymerization reaction; in effect, the entire treated particle 508 becomes a polymerizable "monomer" (although in practice this monomer is usually multifunctional, in the sense of containing a plurality of polymerizable groups). The particle 508 carrying the polymerizable group is then treated with one or more polymerizable monomers or oligomers under conditions effective to cause reaction between the polymerizable group 506 on the particles and the monomer(s) or oligomer(s). If the polymerizable group on the particle is a radical-reactive olefinic group capable of radical polymerization, such conditions will, of course, typically include the presence of a radical polymerization initiator, although in some cases the polymerization may be initiated thermally, with no initiator present. As indicated at 510 in FIG. 5A, the resultant polymerization reaction produces polymer chains which include at least one residue from a polymerizable group previously attached to the particle; if, as is usually the case, multiple polymerizable groups are attached to the particle in the first stage of the process, the residues of two or more of these polymerizable groups may be incorporated into the same polymer chain, which will thus be attached to the particle surface at two or more points.

Figure 6:
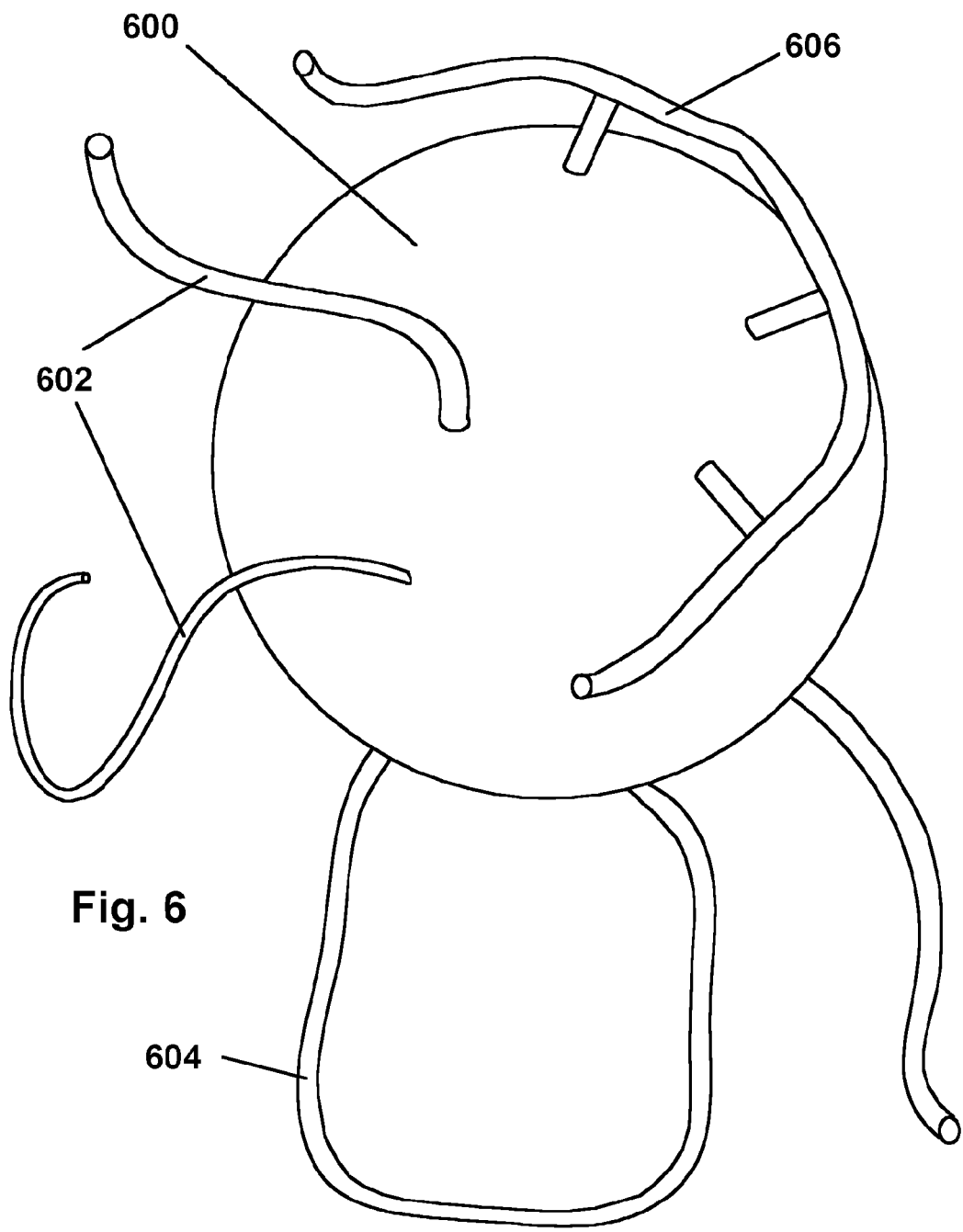
FIG. 6 is a schematic illustration of the type of polymer coating which is believed to be produced by one of the processes of the present invention.

This process is illustrated in FIG. 6, which shows in a highly schematic manner (in practice, the titania particle will be much larger relative to the polymer chains, and far more polymer chains than shown would normally be attached to a single particle), a structure which is believed to be typical of polymer-coated particles used in the present invention. FIG. 6 shows a pigment particle 600 bearing multiple polymer chains, including chains 602 which are attached via only one of their ends to the particle 600, a chain 604 which is attached via both its ends to the particle 600 and a chain 606 which has both ends free but which is attached to the particle 600 at multiple points intermediate its ends. It will be apparent to those skilled in polymer synthesis that other types of polymer chains could be present; for example, a chain could be attached to the particle 600 at both ends and at one or more intermediate points, or a chain could be attached to the particle 600 at one end and one or more intermediate points, but have its opposed end free from the particle 600. Note also that, as illustrated in FIG. 6, the polymer may not completely cover the surface of the particle 600 in the sense that no additional polymer could be formed on the polymer surface; indeed, as discussed below, it is often found that a second polymerization step will often form additional polymer on a particle's surface. Accordingly, the use of the term "polymer shell" herein does not imply a polymer coating precluding the possibility of forming additional polymer on a particle by a further polymerization step.

Figure 5B:
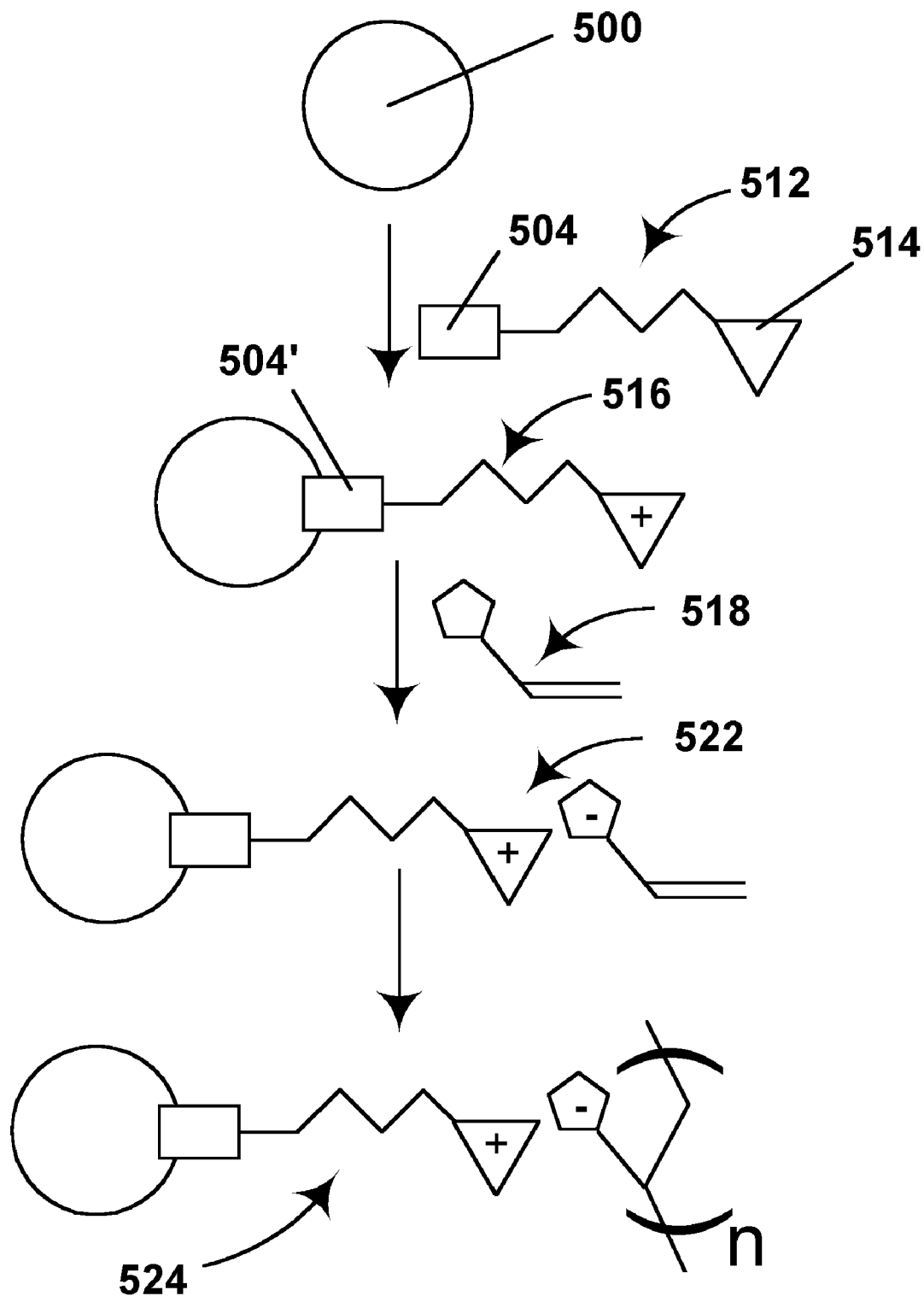

Although, in the first stage of the RGP process, the polymerizable group may be attached to the particle by a covalent bond, in a further variant of the RGP process (which may hereinafter be called "ionic random graft polymerization" or "ionic-RGP"), the polymerizable group is attached to the particle via an ionic bond. Depending upon the chemical nature of the particle, in some cases it may be possible to simply react a monomer with the particle to form the required ionic bond. However, in most cases, it will be necessary to pre-treat the particle with a bifunctional reagent (512 in FIG. 5B) having one functional group 504 capable of reacting with, and bonding to, the particle 500 and a second functional group 514 which can form the necessary ionic bond. Thereafter, the resultant particle 516 is reacted with a monomer 518 having a polymerizable group 506 and a third functional group 520 capable of reacting with the second functional group 514 to form the desired ionic bond, as indicated at 522 in FIG. 5B. The final polymerization step of the RGP process (the ethylene needed for the specific reaction shown is omitted from FIG. 5B for ease of illustration) is then carried out as previously described to produce the product indicated at 524 in FIG. 5B. The ionic bond forming reaction is typically an acid-base reaction; for example, the second functional group 514 may be an ammonium group, such as an alkyl-substituted ammonium group, and the third functional group 520 be a sulfonic acid, or vice versa.

The ionic-RGP process has the advantage that some of the ionically-bonded polymer chains in the final particle 524 can detach and become dispersed in the suspending fluid of the electrophoretic medium, thus providing stabilized counterions to the charged electrophoretic particles. In effect, the ionically-bonded polymer functions as both stabilizing polymer and charge control agent for the electrophoretic particles. If, in an opposite charge dual particle display, both types of particles are provided with polymer coatings formed by ionic-RGP processes, the oppositely charged polymer chains which would detach from the surfaces of the two types of particles should associate with, and electrically neutralize, each other in the suspending fluid, thus providing a desirable reduction in the number of ionic species present in, and the background conductivity of, the electrophoretic medium.

Figure 5C:
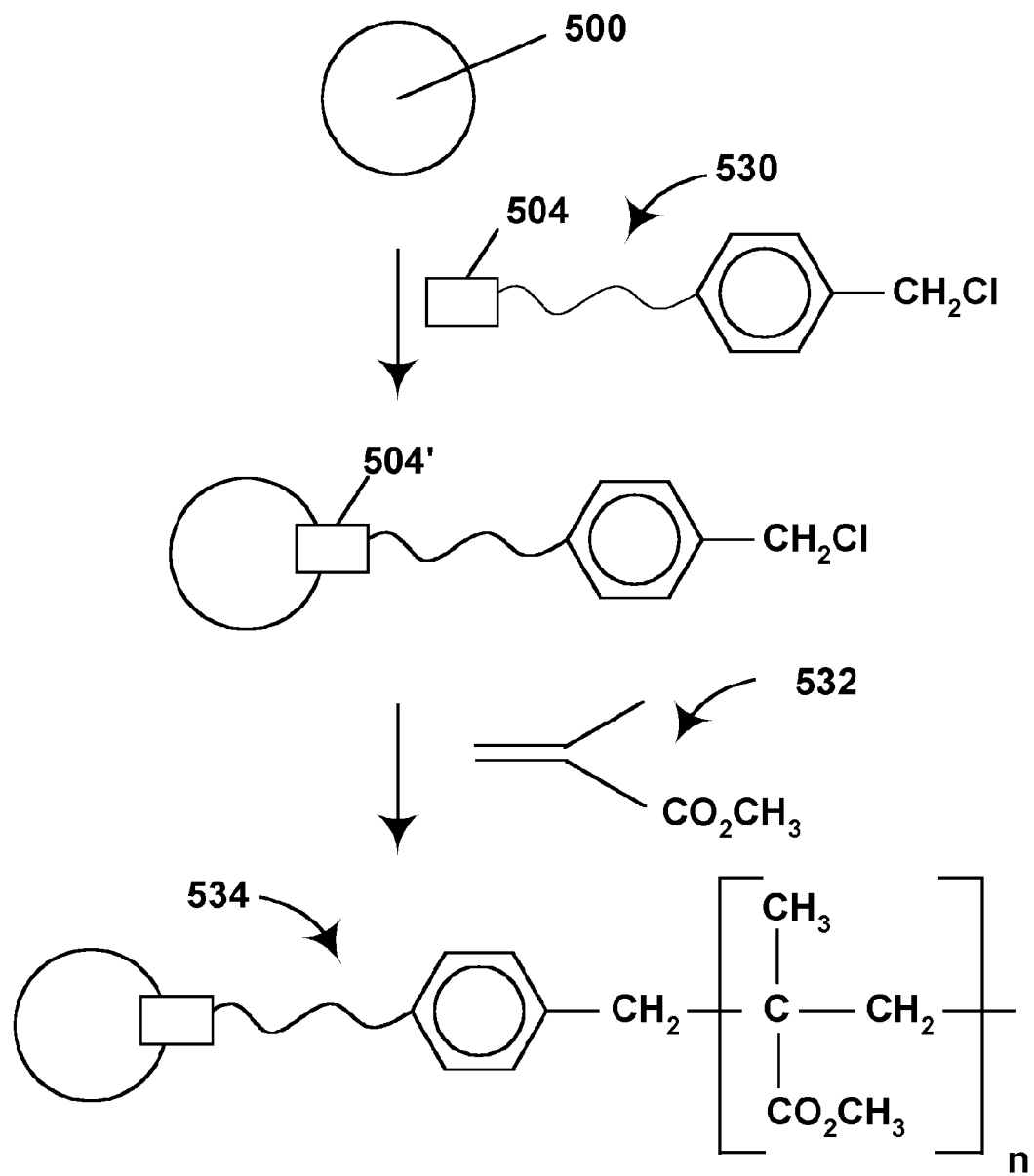

Alternatively, a group capable of initiating polymerization may first be attached to the pigment particle, and a polymer formed from this initiating group. The initiating group may be attached to the polymer surface by a covalent or an ionic bond in any of the ways previously described. For example, a further process described in the aforementioned 2002/0185378 (which may hereinafter be called the "atom transfer radical polymerization" or "ATRP" process) makes use of atom transfer radical polymerization. In the first stage of this process, as illustrated in FIG. 5C, the surface of a particle 500 is treated with a bifunctional reagent 530 having one group 504 capable of reacting with the particle surface and a second group which provides an initiating site for atom transfer radical polymerization (ATRP). The ATRP initiator site may be, for example, a benzylic chlorine (as indicated in FIG. 5C) or other halogen atom. The resultant particle is then treated with an atom transfer radical polymerizable monomer 532 (methyl methacrylate is shown in FIG. 5C) to form a polymer on the particle surface, as indicated at 534. ATRP has the advantage that the polymerization reaction with a first monomer can be stopped by cooling the reaction mixture, the first monomer replaced by a second monomer, and the reaction thereafter restarted by increasing the temperature of the reaction mixture to cause polymerization of the second monomer on to the ends of the previously-formed polymer of the first monomer. These steps may of course be repeated with a introduction of a third monomer. This process forms on the particle a block copolymer of the two (or more) monomers.

The processes used to prepare polymer-coated particles used in the present invention are not restricted to the use of ATRP initiating sites on the particle, but include the use of other types of initiating sites, for example ionic or free radical initiating sites. Also, the bifunctional reagents mentioned above need not be single monomeric reagents but can themselves be polymeric. For example, a silica/alumina coated titania particle was coated with a terpolymer of styrene, chloromethylstyrene and 3-(trimethoxysilyl)propyl methacrylate by suspending the titania particles in a solution of the terpolymer in tetrahydrofuran (THF) and adding hexane to reduce the solubility of the polymer. After precipitation of the terpolymer, the particles are subjected to conditions effective to cause condensation between the trihydroxysilyl groups on the polymer (the trimethoxysilyl groups having previously been hydrolyzed to this form) and the silanol groups which are always present on silica-coated titania particles, thus covalently binding the polymer to the particle surface. This condensation can be effected under conditions as mild as drying at room temperature for about 24 hours, or heating to 60° C. for 1 to 2 hours. The chloromethylstyrene residues in the bound polymer can then serve as ATRP initiating sites for formation of additional polymer on to the particles.

The processes used to prepare electrophoretic particles will typically include more than one stage and/or more than one type of polymerization. For example, in one variant of such a process (which may hereinafter be called the "RGP-ATRP" process), the particle is first subjected to the RGP process described above, except that a mixture of monomers is used including at least one monomer (for example, a chloromethylstyrene) which contains a group that provides an initiating site for ATRP. Thus, there is formed on the particle a polymer chain which contains ATRP initiating sites. After the RGP polymerization is concluded, the particle is then subjected to ATRP, so that polymer side chains form from the ATRP initiating sites, thus producing a "hyper-branched" polymer having main chains formed by the RGP process and side chains formed by ATRP. It has been found that this type of polymer structure is highly advantageous in stabilizing a suspension of electrophoretic particles in the non-ionic media typically used as suspending fluids in electrophoretic displays. A similar type of hyper-branched polymer could be produced by including in the mixture of monomers used in the RGP step a monomer which contains an initiating group for stable free radical polymerization (SFRP), this SFRP initiating group being chosen so that it essentially does not initiate polymerization under the conditions used in the RGP step. After the RGP step is concluded, the particles is then subjected to SFRP to produce the hyper-branched polymer.

Attachment of Polymerizable Groups and Initiators

In preparing the electrophoretic particles of the present invention, polymerizable groups and initiators may be attached to the surface of the base particles using any bifunctional reagents having one group capable of bonding, covalently or ionically, to the surface, and a second group providing the required polymerizable or initiating functionality. The independent functioning of the two groups has the advantage of providing great flexibility in adapting the present invention to use any desired type of particle, since it will normally readily be apparent to skilled chemists how to vary (say) the group which bonds to the particle surface in order to adapt the processes to a different type of particle, while keeping the same polymerizable or initiating functionality, so that the later stages of the processes will need few if any changes as a result of changing the type of base particle being used.

In describing the reagents used to provide the desired polymerizable or initiating functionality as "bifunctional", we do not exclude the possibility that the reagents may contain more than one group of each type, and indeed in some cases it may be desirable to provide more than one group of one or both types. For example, polymerization initiators are known (such as 4,4'-azobis(4-cyanovaleric acid)) having more than one ionic site, and such initiators may be used. Also, as previously noted, the bifunctional reagent may have the form of a polymer containing repeating units having the capacity to bond to the particle surface and other repeated units having the desired polymerizable or initiating functionality, and such polymeric bifunctional reagents will normally contain multiple repeating units of both these types.

The preferred class of functional groups for bonding to many ceramic oxide pigments, but especially silica- and/or alumina-coated titania and similar silica-coated pigments, are silane coupling groups, especially trialkoxy silane coupling groups. One preferred reagent for attaching a polymerizable group to titania and similar pigments is the aforementioned 3-(trimethoxysilyl)propyl methacrylate:

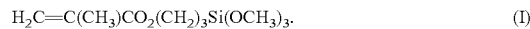
$$H_2C=C(CH_3)CO_2(CH_2)_3Si(OCH_3)_3. \quad (I)$$

This material is available commercially from Dow Chemical Company, Wilmington, Del. under the trade name Z6030. The corresponding acrylate may also be used. Another useful reagent is the aminosilyl derivative of the formula:

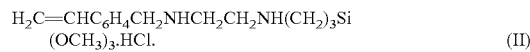
$$H_2C=CHC_6H_4CH_2NHCH_2CH_2NH(CH_2)_3Si(OCH_3)_3 \cdot HCl. \quad (II)$$

In addition to providing an "anchor" for the polymer shell to be formed later around the electrophoretic particle, these silyl meth(acrylates) contain charge-control groups which impart to the final electrophoretic particle the ability to acquire a desired charge in the presence of a suitable charging agent or agents. The reagent of Formula (II) is used when a positively charging particle is desired, while the reagent of Formula (I) gives negatively charging particles. Both reagents, of course, comprise a polymerizable vinyl grouping that allows grafting of polymeric radicals generated in solution.

When a silica- and/or alumina-coated titania (or similar silica-coated) particle is to be used in an ionic RGP process, it is preferred that the particle first be treated with a silane coupling agent containing a basic group, preferably a substituted ammonium group, thereby providing amino groups on the particle surface. The resultant amino-functionalized particle is then preferably treated with an acid containing the desired polymerizable group, which thus becomes ionically bound to the particle surface. For example, the aforementioned silica/alumina coated titania R960 may be reacted with the silane coupling agent, N-trimethoxysilylpropyl-N,N,N-trimethylammonium chloride, to obtain a pigment with quaternary ammonium groups covalently attached to its surface. This amino-functionalized pigment may then be dispersed in water with 4-styrene sulfonic acid and precipitated to obtain a pigment with styrene functionality ionically associated with the quaternary ammonium groups.

Similarly, when it is desired to attach an initiating group to a coated titania surface, the surface may first be provided with amino functionality in the manner already described, and then a reagent, for example, 4,4'-azobis(4-cyanovaleric acid), containing both an acidic group and an initiating group may be used to ionically bond the initiating group to the particle surface.

The preferred group for bonding to carbon black is a diazonium group; as is well-known to organic chemists, such a group is normally formed in situ by reaction of an aromatic amine with a nitrite. A series of patents and published applications of Cabot Corporation, Boston, Mass. describes the use of diazonium chemistry to attach a wide variety of functional groups to carbon black; see, for example, U.S. Pat. Nos. 5,554,739; 5,672,198; 5,698,016; 5,707,432; 5,713,988; 5,851,280; 5,885,335; 5,895,522; 5,968,243; 6,068,688; and 6,103,380, and International Applications Nos. WO 96/18695; WO 99/51690; WO 00/05312; and WO 00/22051. The chemistry has also been extended to other pigments; see, for example, U.S. Pat. Nos. 5,837,045; 5,922,118; and 5,958,999, and International Applications Nos. WO 00/52102 and WO 00/53681. Preferred amines for use with carbon black in the present processes are aniline derivatives, especially para-derivatives of aniline. For example, a preferred reagent for attaching vinyl groups to carbon black is 4-vinylaniline.

Although the reasons for the phenomenon are not entirely understood, it has been observed that the conditions under which the bifunctional reagent is attached to the particle surface may affect the characteristics of the final electrophoretic particles. For example, coated titania particles can be reacted with silane coupling agents under both acidic and basic conditions. However, acidic conditions are preferred, since it has been found that with such conditions for the initial silane coupling reaction, the final polymer-coated titania particles consistently charge negatively with many charge control agents. If, however, basic conditions are used for the initial silane coupling reaction, the final polymer-coated titania particles may charge with both polarities, which is highly undesirable when the particles are to be used in an electrophoretic display.

The polymerizable and initiating groups used to prepare the present electrophoretic particles and media may be any of those known in the art, provided of course that the relevant groups are compatible with the reactions used to attach them to the particle surface. The polymerizable or initiating group may be subjected to chemical modification, for example by removal of a protecting group, after it has been attached to the particle surface. If, for example, a particular polymerization required the presence of a carboxylic acid group on the particle surface, the bifunctional reagent used might contain this group in esterified form, with the group being de-esterified after it has been attached to the particle surface. (A similar procedure may be employed when preparing a surface for ionic bonding to a polymerizable group in the ionic RGP process. For example, a silica/alumina coated titania particle may be treated with a copolymer of 3-(trimethoxysilyl)propyl methacrylate and t-butyl acrylate, thus causing the silyl groups to bond to the particle surface, and leaving the esterified acrylate groups exposed. The particle is then treated with acetic acid to convert the esterified acrylate groups to free acrylic acid groups. Subsequent reaction of the particle with dimethylaminoethyl methacrylate causes an acid/base reaction and ionically bonds the methacrylate groups to the particle, where they serve as polymerizable groups for use in an RGP process.) Similarly, when it is desired to attached a chloroalkyl group to the particle surface to serve as an initiator for ATRP, the bifunctional reagent used might contain the corresponding hydroxyalkyl group, which could be converted to the desired chloroalkyl group by reaction with a chlorinating agent, for example thionyl chloride.

The generally preferred polymerizable groups are ethylenically unsaturated groups, especially vinyl, acrylate and methacrylate groups. The generally preferred initiating groups for ATRP are haloalkyl groups, desirably chloroalkyl groups and most desirably chloromethyl groups. Free radical polymerization initiating groups which may be used include those derived from [10-(t-butyldioxy)decyl]bromide, 2-(carbamoylazo)isobutyronitrile, and 4,4'-azobis(4-cyanovaleric acid).

When choosing the bifunctional reagent to provide polymerizable or initiating functionality on the particle, attention should be paid to the relative positions of the two groups within the reagent. As should be apparent to those skilled in polymer manufacture, the rate of reaction of a polymerizable or initiating group bonded to a particle may vary greatly depending upon whether the group is held rigidly close to the particle surface, or whether the group is spaced (on an atomic scale) from that surface and can thus extend into a reaction medium surrounding the particle, this being a much more favorable environment for chemical reaction of the group. In general, it is preferred that there be at least three atoms in the direct chain between the two functional groups; for example, the aforementioned 3-(trimethoxysilyl)propyl methacrylate provides a chain of four carbon and one oxygen atoms between the silyl and ethylenically unsaturated groups, while the aforementioned 4-vinylaniline separates the amino group (or the diazonium group, in the actual reactive form) from the vinyl group by the full width of a benzene ring, equivalent to about the length of a three-carbon chain.

Polymer Structure and Polymer-forming Processes

Before discussing in detail the preferred processes for forming polymers on the electrophoretic particles, it is first appropriate to rehearse the basic reasons why such polymers are advantageous. The fundamental reasons for providing polymer on electrophoretic particles are to control the stability of the suspension of particles in the suspending fluid, and to stabilize the electrophoretic properties of the particles. For these purposes, it is desirable that the polymer assist in stabilizing the charge on the particles as environmental conditions vary.

In practice, the suspending fluid in an electrophoretic medium is typically a liquid with a low dielectric constant, such as a hydrocarbon, halocarbon (especially fluorocarbon), or silicone. The incompatible monomer media of the present invention may use any of these types of suspending fluid. The invention will be primarily described below with reference to media containing hydrocarbon suspending fluids, but modification of the media to use other types of suspending fluid will readily be apparent to those skilled in colloid chemistry in such suspending fluids. The polymer shell itself typically comprises a major proportion of hydrocarbon chains (i.e., chains forming a homopolymer that is highly compatible with the suspending medium); except for groups provided for charging purposes and for purposes of adjusting compatibility with the suspending fluid, as discussed below, large numbers of strongly polar or ionic groups are undesirable. Also, as already discussed, at least when the medium in which the particles are to be used comprises an aliphatic hydrocarbon suspending fluid (as is commonly the case), it is advantageous for the polymer to have a branched or "comb" structure, with a main chain and a plurality of side chains extending away from the main chain. Each of these side chains should have at least about four, and preferably at least about six, carbon atoms. Substantially longer side chains may be advantageous; for example, lauryl (C12) side chains. The side chains may themselves be branched; for example, each side chain could be a branched alkyl group, such as a 2-ethylhexyl group. It is believed (although the invention is in no way limited by this belief) that, because of the high affinity of hydrocarbon chains for the hydrocarbon-based suspending fluid, the branches of the polymer spread out from one another in a brush or tree-like structure through a large volume of liquid, thus preventing close association with other similar particles and causing the particles to be colloidally stable in the suspending fluid.

There are two basic approaches to forming such a stabilizing polymer. The first approach uses monomers which inherently provide the necessary side chains. Typically, such a monomer has a single polymerizable group at one end of a long chain (at least four, and preferably at least six, carbon atoms). Monomers of this type include hexyl acrylate, 2-ethylhexyl acrylate and lauryl methacrylate. Isobutyl methacrylate and 2,2,3,4,4,4-hexafluorobutyl acrylate have also been used successfully. In some cases, it may be desirable to limit the number of side chains formed in such processes, and this can be achieved by using a mixture of monomers (for example, a mixture of lauryl methacrylate and methyl methacrylate) to form a random copolymer in which only some of the repeating units bear long side chains. In the second approach, typified by the RGP-ATRP process already described, a first polymerization reaction is carried out using a mixture of monomers, at least one of these monomers bearing an initiating group, thus producing a first polymer containing such initiating groups. The product of this first polymerization reaction is then subjected to a second polymerization, typically under different conditions from the first polymerization, so as to cause the initiating groups within the polymer to cause polymerization of additional monomer on to the original polymer, thereby forming the desired side chains. As with the bifunctional reagents discussed above, we do not exclude the possibility that some chemical modification of the initiating groups may be effected between the two polymerizations. In such a process, the side chains themselves do not need to be heavily branched and can be formed from a small monomer, for example methyl methacrylate.

Despite the unusual nature of the polymerizations being discussed, (one reactant therein is a "macroscopic" particle, typically of the order of 1 µm or more in diameter, usually bearing multiple polymerizable or initiating groups rather than a single molecule), the polymerization processes can be carried out using conventional techniques. For example, free radical polymerization of ethylenic or similar radical polymerizable groups attached to particles may be effected using conventional free radical initiators, such as 2,2'-azobis (isobutyrylnitrile) (AIBN), while ATRP polymerization can be effected using the conventional metal complexes, as described in Wang, J. S., et al., *Macromolecules*, 1995, 23, 7901, and *J. Am. Chem. Soc.*, 1995, 117, 5614, and in Beers, K. et al., *Macromolecules*, 1999, 32, 5772-5776. See also U.S. Pat. Nos. 5,763,548; 5,789,487; 5,807,937; 5,945,491; 5,986,015; 6,069,205; 6,071,980; 6,111,022; 6,121,371; 6,124,411; 6,137,012; 6,153,705; 6,162,882; 6,191,225; and 6,197,883. The entire disclosures of these papers and patents are herein incorporated by reference. The presently preferred catalyst for carrying out ATRP is cuprous chloride in the presence of bipyridyl (Bpy).

RGP processes in which particles bearing polymerizable groups are reacted with a monomer in the presence of an initiator will inevitably cause some formation of "free" polymer not attached to a particle, as the monomer in the reaction mixture is polymerized. The unattached polymer may be removed by repeated washings of the particles with a solvent (typically a hydrocarbon) in which the unattached polymer is soluble, for example, (at least in the case of metal oxide or other dense particles) by centrifuging off the treated particles from the reaction mixture (with or without the previous addition of a solvent or diluent), re-dispersing the particles in fresh solvent, and repeating these steps until the proportion of unattached polymer has been reduced to an acceptable level. (The decline in the proportion of unattached polymer can be followed by thermogravimetric analysis of samples of the polymer.) Empirically, it does not appear that the presence of a small proportion of unattached polymer, of the order of 1 percent by weight, has any serious deleterious effect on the electrophoretic properties of the treated particles; indeed, in some cases, depending upon the chemical natures of the unattached polymer and the suspending fluid, it may not be necessary to separate the polymer-coated particles from the unattached polymer before using the particles in an electrophoretic display.

As described in the aforementioned 2002/0185378, it has been found that there is a optimum range for the amount of polymer which should be formed on electrophoretic particles, and that forming either an excessive or an insufficient amount of polymer on the particles can degrade their electrophoretic characteristics. The optimum range will vary with a number of factors, including the density and size of the particles being coated, the nature of the suspending medium in which the particles are intended to be used, and the nature of polymer formed on the particles, and for any specific particle, polymer and suspending medium, the optimum range is best determined empirically. However, by way of general guidance, it should be noted that the denser the particle, the lower the optimum proportion of polymer by weight of the particle, and the more finely divided the particle (the smaller the particle size), the higher the optimum proportion of polymer. The aforementioned 2002/0185378 states that the particles should be coated with at least about 2 and desirably at least about 4, percent by weight of polymer, and that, in most cases, the optimum proportion of polymer will range from about 4 to about 15 percent by weight of the particle, and typically from about 6 to about 15 percent by weight, and most desirably from about 8 to about 12 percent by weight. More specifically, in the case of titania particles, the aforementioned 2002/0185378 states that the preferred range of polymer is from about 8 to about 12 percent by weight of the titania.

However, to facilitate application of the present invention to particles having a wide range of particle sizes and densities, it may be advantageous to describe the amount of polymer is in terms of the surface density of polymer (i.e., the weight of polymer per unit area of particle surface, for example milligrams of polymer per square meter of particles surface. The surface density of the polymer can be calculated from the formula:

$$\Gamma = W\rho D/6$$

where $\Gamma$ is the surface density of polymer, W is the weight of polymer per gram of sample (obtained from thermogravimetric analysis), $\rho$ is the density of the base particle, and D is the diameter of the base particle. For copper chromate, a useful range of surface density has been found to be about 2 to about 40 mg/g, with a preferred range being about 14 to about 24 mg/g and a particularly preferred range being about 18 to about 22 mg/g.

As regards the optimum proportion of polymer, carbon black tends to be a special case. Carbon black is of low density and (at least in its commercial forms) extremely finely divided, so much so that it is customary to characterize the state of division of the material not by an average particle size but by its capacity to adsorb various gases or liquids under standardized conditions. Thus, the optimum amount of polymer on carbon black may be substantially higher than on most other pigments. Although we generally prefer to provide about 6 to about 14, and desirably about 8 to about 12 weight percent of polymer on carbon black, under certain circumstances carbon black may be provided with up to about 20, or even about 25 weight percent of polymer.

It is generally preferred that the polymers formed on the present electrophoretic particles include charged or chargeable groups, since such groups are useful in controlling the charge on the electrophoretic particles. Hitherto, the charge on electrophoretic particles has normally been controlled by adding to the electrophoretic medium a charge control agent, which is typically a surfactant-like molecule or structure which absorbs on to the particles and varies the charge thereon. Charge control agents often charge the particles by poorly understood and uncontrolled processes, and can lead to undesirably high conductivity of the electrophoretic medium. Also, since the charge control agent is only physically adsorbed on to the particles and is not bound thereto, changes in conditions may cause partial or complete desorption of the charge control agent from the particles, with consequent undesirable changes in the electrophoretic characteristics of the particles. The desorbed charge control agent might resorb on to other surfaces within the electrophoretic medium, and such resorption has the potential for causing additional problems. The use of charge control agents is especially difficult in dual particle electrophoretic media, where a charge control agent may adsorb on to the surface of one or both types of electrophoretic particles. Indeed, cases have been observed where the addition of a charge control agent to a dual particle electrophoretic medium, which was intended to be of the type in which the two types of particles bear charges of opposite polarity, resulted in some particles of one type becoming positively charged, and other particles of the same type becoming negatively charged, thus rendering the medium essentially useless for its intended purpose. In the case of an encapsulated dual particle electrophoretic medium, it is also possible for the charge control agent to adsorb on to the capsule wall. Providing charged groups within the bound polymer ensures that these charged groups remain fixed on to the particle, with essentially no tendency to desorb (unless the polymer chains themselves are rendered capable of desorption, as already discussed).

Instead of incorporating charged or chargeable groups within the polymer attached to the pigment particle, or in addition thereto, charged or chargeable groups may be directly attached to the pigment particle without being incorporated into a polymer, polymer can be provided on the particle's surface in addition to the charged or chargeable groups.

Charged or chargeable groups may be incorporated into the polymer via either the bifunctional agent used to provide polymerizable or initiating functionality to the pigment (as already mentioned, for example using the reagent of Formula (I) above), or via one or more monomers used to form the polymer chain. If the charged or chargeable groups are to provided via monomers, a variety of acrylates and methacrylates are available containing acidic or basic groups, as are a variety of other monomers (for example, 4-vinylpyridine) containing a polymerizable group and a basic or acidic group. As previously mentioned in other contexts, it may be desirable to provide the acidic or basic group in a "blocked" form in the monomer used, and to de-block the group after formation of the polymer. For example, since ATRP cannot be initiated in the presence of acid, if it is desired to provide acidic groups within the polymer, esters such as t-butyl acrylate or isobornyl methacrylate may be used, and the residues of these monomers within the final polymer hydrolyzed to provide acrylic or methacrylic acid residues.

When it is desired to produce charged or chargeable groups on the pigment particles and also polymer separately attached to the particles, it may be very convenient to treat the particles (after any preliminary treatment such as silica coating) with a mixture of two reagents, one of which carries the charged or chargeable group (or a group which will eventually be treated to produce the desired charged or chargeable group), and the other of which carries the polymerizable or polymerization-initiating group. Desirably, the two reagents have the same, or essentially the same, functional group which reacts with the particle surface so that, if minor variations in reaction conditions occur, the relative rates at which the reagents react with the particles will change in a similar manner, and the ratio between the number of charged or chargeable groups and the number of polymerizable or polymerization-initiating groups will remain substantially constant. It will be appreciated that this ratio can be varied and controlled by varying the relative molar amounts of the two (or more) reagents used in the mixture. Examples of reagents which provide chargeable sites but not polymerizable or polymerization-initiating groups include 3-(trimethoxysilyl)propylamine, N-[3-(trimethoxysilyl)propyl]diethylene-triamine, N-[3-(trimethoxysilyl)propyl]ethylene and 1-[3-(trimethoxysilyl)propyl]urea; all these silane reagents may be purchased from United Chemical Technologies, Inc., Bristol, Pa., 19007.

In one form of the ATRP process, a first ATRP step is conducted using a monomer which ultimately provides acidic, basic or other ionic groups within the final polymer; this monomer may be used alone or in admixture with a monomer which provides neutral residues within the polymer. For example, this first ATRP step might be carried out with 4-vinylpyridine, 2-(dimethylamino)methacrylate or t-butyl methacrylate. Thereafter, a second ATRP step is conducted using a neutral monomer to produce hydrophobic, neutral polymer block which has a high affinity for hydrocarbon suspending fluids and which thus sterically stabilizes the inner charged particle/polymer block. Obviously, similarly double-coated particles can be produced using polymerization techniques other than ATRP.

Polymer-coated particles may be used with advantage in all of the types of electrophoretic display (namely single particle, opposite charge dual particle, same polarity dual particle and polymer dispersed) previously described. However, the particles may be especially useful in opposite charge dual particle electrophoretic displays, which are especially difficult to stabilize, since as already mentioned the two types of particles of opposite polarity are inherently attracted towards one another and hence have a strong tendency to form aggregates which may interfere with the electrophoretic operation of the display.

The polymer-coated pigment particles of the present invention may also be useful in applications other than electrophoretic displays. For example, the controlled affinity for hydrocarbon materials provided by the polymer coating on the present pigments should render the pigments advantageous for use in polymeric and rubber matrices, in which the pigments should be more readily dispersible than similar but uncoated pigments. The flexibility in the chemical nature of the polymer coating allows the coating to be "tuned" for controlled dispersibility in any specific matrix. Thus, the present pigments may be used as dispersible pigments or reactive extrusion compounds. Furthermore, the polymer coating on the particles may be useful in improving the mechanical properties of such pigment/polymer or rubber blends by reducing the tendency for such blends to shear or fracture at the interface between the particles and the matrix material. If the polymer-coated particles are produced by a process which produces the polymer-coated particles in admixture with "free" polymer not attached to the particles (as discussed above), it will, in many cases, not be necessary to separate the coated particles from the free polymer before dispersing the particles in the polymeric or rubber matrix, since the free polymer will disperse harmlessly in the matrix.

Apart from the provision of the polymer on the pigment particles, the electrophoretic media of the present invention may employ the same components and manufacturing techniques as in the aforementioned Massachusetts Institute of Technology and E Ink Corporation patents and applications. The following Sections A-D describe useful materials for use in the various components of the encapsulated electrophoretic displays of the present invention.

A. Suspending Fluid

As already indicated, the suspending fluid containing the particles should be chosen based on properties such as dielectric constant, density, refractive index, and solubility. A preferred suspending fluid has a low dielectric constant (about 2), high volume resistivity (about $10^{15}$ ohm-cm), low viscosity (less than 5 centistokes ("cst")), low toxicity and environmental impact, low water solubility (less than 10 parts per million ("ppm")), a high boiling point (greater than 90° C.). For some applications, a high specific gravity (greater than 1.5) and a low refractive index (less than 1.2) may be desirable as well.

The choice of suspending fluid may be based on concerns of chemical inertness, density matching to the electrophoretic particle, or chemical compatibility with both the electrophoretic particle and capsule or microcell wall (in the case of encapsulated electrophoretic displays). The viscosity of the fluid should be low when movement of the particles is desired. The refractive index of the suspending fluid may also be substantially matched to that of the particles. As used herein, the refractive index of a suspending fluid "is substantially matched" to that of a particle if the difference between their respective refractive indices is between about zero and about 0.3, and is preferably between about 0.05 and about 0.2. However, for electrophoretic displays in which the optical states are determined in part by scattering efficiency, a large difference in refractive index between the scattering entity and the medium is desired. Titania particles are typically used as scattering particles to produce a white state in dual particle electrophoretic displays, and this material has a high refractive index (ca. 2.7), so that a low refractive index in the suspending medium is desirable.

Organic solvents, such as halogenated organic solvents, saturated linear or branched hydrocarbons, silicone oils, and low molecular weight halogen-containing polymers are some useful suspending fluids. The suspending fluid may comprise a single fluid. The fluid will, however, often be a blend of more than one fluid in order to tune its chemical and physical properties. Furthermore, the fluid may contain surface modifiers to modify the surface energy or charge of the electrophoretic particle or bounding capsule. Reactants or solvents for the microencapsulation process (oil soluble monomers, for example) can also be contained in the suspending fluid. Charge control agents can also be added to the suspending fluid.

Useful organic solvents include, but are not limited to, epoxides, such as decane epoxide and dodecane epoxide; vinyl ethers, such as cyclohexyl vinyl ether and Decave (Registered Trade Mark of International Flavors & Fragrances, Inc., New York, N.Y.); and aromatic hydrocarbons, such as toluene and other alkyl benzene derivatives such as dodecylbenzene and naphthalene and alkyl naphthalene derivatives. Useful halogenated organic solvents include, but are not limited to, tetrafluorodibromoethylene, tetrachloroethylene, trifluorochloroethylene, 1,2,4-trichlorobenzene and carbon tetrachloride. These materials have high densities. Useful hydrocarbons include, but are not limited to, dodecane, tetradecane, the aliphatic hydrocarbons in the Isopar (Registered Trade Mark) series (Exxon, Houston, Tex.), Norpar (Registered Trade Mark) (a series of normal paraffinic liquids), Shell-Sol (Registered Trade Mark) (Shell, Houston, Tex.), and Sol-Trol (Registered Trade Mark) (Shell), naphtha, and other petroleum solvents. These materials usually have low densities. Useful examples of silicone oils include, but are not limited to, octamethyl cyclosiloxane and higher molecular weight cyclic siloxanes, poly(methyl phenyl siloxane), hexamethyldisiloxane, and polydimethylsiloxane. These materials usually have low densities. Useful low molecular weight halogen-containing polymers include, but are not limited to, poly(chlorotrifluoroethylene) polymer (Halogenated Hydrocarbon Inc., River Edge, N.J.), Galden (Registered Trade Mark) (a perfluorinated ether from Ausimont, Morristown, N.J.), or Krytox (Registered Trade Mark) from du Pont (Wilmington, Del.). In a preferred embodiment, the suspending fluid is a poly (chlorotrifluoroethylene) polymer. In a particularly preferred embodiment, this polymer has a degree of polymerization from about 2 to about 10. Many of the above materials are available in a range of viscosities, densities, and boiling points.

If the medium being formed is one which requires the formation of capsules, the fluid must be capable of being formed into small droplets prior to a capsule being formed. Processes for forming small droplets include flow-through jets, membranes, nozzles, or orifices, as well as shear-based emulsifying schemes. The formation of small drops may be assisted by electrical or sonic fields. Surfactants and polymers can be used to aid in the stabilization and emulsification of the droplets in the case of an emulsion type encapsulation. One surfactant for use in displays of the invention is sodium dodecylsulfate.

It can be advantageous in some displays for the suspending fluid to contain an optically absorbing dye. This dye must be soluble in the fluid, but will generally be insoluble in the other components of the capsule. There is much flexibility in the choice of dye material. The dye can be a pure compound, or blends of dyes to achieve a particular color, including black. The dyes can be fluorescent, which would produce a display in which the fluorescence properties depend on the position of the particles. The dyes can be photoactive, changing to another color or becoming colorless upon irradiation with either visible or ultraviolet light, providing another means for obtaining an optical response. Dyes could also be polymerizable by, for example, thermal, photochemical or chemical diffusion processes, forming a solid absorbing polymer inside the bounding shell.

There are many dyes that can be used in electrophoretic displays. Properties important here include light fastness, solubility in the suspending liquid, color, and cost. These dyes are generally chosen from the classes of azo, anthraquinone, and triphenylmethane type dyes and may be chemically modified so as to increase their solubility in the oil phase and reduce their adsorption by the particle surface.

A number of dyes already known to those skilled in the art of electrophoretic displays will prove useful. Useful azo dyes include, but are not limited to: the Oil Red dyes, and the Sudan Red and Sudan Black series of dyes. Useful anthraquinone dyes include, but are not limited to: the Oil Blue dyes, and the Macrolex Blue series of dyes. Useful triphenylmethane dyes include, but are not limited to, Michler's hydrol, Malachite Green, Crystal Violet, and Auramine O.

B. Charge Control Agents and Particle Stabilizers

Charge control agents may be used, with or without charged groups in polymer coatings, to provide good electrophoretic mobility to the electrophoretic particles. Stabilizers may be used to prevent agglomeration of the electrophoretic particles, as well as prevent the electrophoretic particles from irreversibly depositing onto the capsule wall. Either component can be constructed from materials across a wide range of molecular weights (low molecular weight, oligomeric, or polymeric), and may be a single pure compound or a mixture. The charge control agent used to modify and/or stabilize the particle surface charge is applied as generally known in the arts of liquid toners, electrophoretic displays, non-aqueous paint dispersions, and engine-oil additives. In all of these arts, charging species may be added to non-aqueous media in order to increase electrophoretic mobility or increase electrostatic stabilization. The materials can improve steric stabilization as well. Different theories of charging are postulated, including selective ion adsorption, proton transfer, and contact electrification.

An optional charge control agent or charge director may be used. These constituents typically consist of low molecular weight surfactants, polymeric agents, or blends of one or more components and serve to stabilize or otherwise modify the sign and/or magnitude of the charge on the electrophoretic particles. Additional pigment properties which may be relevant are the particle size distribution, the chemical composition, and the lightfastness.

Charge adjuvants may also be added. These materials increase the effectiveness of the charge control agents or charge directors. The charge adjuvant may be a polyhydroxy compound or an aminoalcohol compound, and is preferably soluble in the suspending fluid in an amount of at least 2% by weight. Examples of polyhydroxy compounds which contain at least two hydroxyl groups include, but are not limited to, ethylene glycol, 2,4,7,9-tetramethyldecyne-4,7-diol, poly(propylene glycol), pentaethylene glycol, tripropylene glycol, triethylene glycol, glycerol, pentaerythritol, glycerol tris(12-hydroxystearate), propylene glycerol monohydroxystearate, and ethylene glycol monohydroxystearate. Examples of aminoalcohol compounds which contain at least one alcohol function and one amine function in the same molecule include, but are not limited to, triisopropanolamine, triethanolamine, ethanolamine, 3-amino-1-propanol, o-aminophenol, 5-amino-1-pentanol, and tetrakis(2-hydroxyethyl)ethylene-diamine. The charge adjuvant is preferably present in the suspending fluid in an amount of about 1 to about 100 milligrams per gram ("mg/g") of the particle mass, and more preferably about 50 to about 200 mg/g.

In general, it is believed that charging results as an acid-base reaction between some moiety present in the continuous phase and the particle surface. Thus useful materials are those which are capable of participating in such a reaction, or any other charging reaction as known in the art. However, other charging agents that function by different mechanisms may also be used in this invention.

Different non-limiting classes of charge control agents which are useful include organic sulfates or sulfonates, metal soaps, block or comb copolymers, organic amides, organic zwitterions, and organic phosphates and phosphonates. Useful organic sulfates and sulfonates include, but are not limited to, sodium bis(2-ethylhexyl) sulfosuccinate, calcium dodecylbenzenesulfonate, calcium petroleum sulfonate, neutral or basic barium dinonylnaphthalene sulfonate, neutral or basic calcium dinonylnaphthalene sulfonate, dodecylbenzenesulfonic acid sodium salt, and ammonium lauryl sulfate. Useful metal soaps include, but are not limited to, basic or neutral barium petronate, calcium petronate, Co—, Ca—, Cu—, Mn—, Ni—, Zn—, and Fe— salts of naphthenic acid, Ba—, Al—, Zn—, Cu—, Pb—, and Fe— salts of stearic acid, divalent and trivalent metal carboxylates, such as aluminum tristearate, aluminum octanoate, lithium heptanoate, iron stearate, iron distearate, barium stearate, chromium stearate, magnesium octanoate, calcium stearate, iron naphthenate, zinc naphthenate, Mn— and Zn— heptanoate, and Ba—, Al—, Co—, Mn—, and Zn— octanoate. Useful block or comb copolymers include, but are not limited to, AB diblock copolymers of (A) polymers of 2-(N,N-dimethylamino)ethyl methacrylate quaternized with methyl p-toluenesulfonate and (B) poly(2-ethylhexyl methacrylate), and comb graft copolymers with oil soluble tails of poly(12-hydroxystearic acid) and having a molecular weight of about 1800, pendant on an oil-soluble anchor group of poly(methyl methacrylate-methacrylic acid). Useful organic amides include, but are not limited to, polyisobutylene succinimides such as OLOA 371 or 1200 (available from Chevron Oronite Company LLC, Houston, Tex.), or Solsperse 17000 (available from Avecia Ltd., Blackley, Manchester, United Kingdom; "Solsperse" is a Registered Trade Mark), and N-vinylpyrrolidone polymers. Useful organic zwitterions include, but are not limited to, lecithin. Useful organic phosphates and phosphonates include, but are not limited to, the sodium salts of phosphated mono- and di-glycerides with saturated and unsaturated acid substitutents.

Particle dispersion stabilizers may be added to prevent particle flocculation or attachment to the capsule walls. For the typical high resistivity liquids used as suspending fluids in electrophoretic displays, non-aqueous surfactants may be used. These include, but are not limited to, glycol ethers, acetylenic glycols, alkanolamides, sorbitol derivatives, alkyl amines, quaternary amines, imidazolines, dialkyl oxides, and sulfosuccinates.

C. Encapsulation

Encapsulation may be accomplished in a number of different ways. Numerous suitable procedures for encapsulation are detailed in both Microencapsulation, Processes and Applications, (I. E. Vandegaer, ed.), Plenum Press, New York, N.Y. (1974) and Gutcho, Microcapsules and Microencapsulation Techniques, Noyes Data Corp., Park Ridge, N.J. (1976). The processes fall into several general categories, all of which can be applied to the present invention: interfacial polymerization, in situ polymerization, physical processes, such as coextrusion and other phase separation processes, in-liquid curing, and simple/complex coacervation.

Numerous materials and processes should prove useful in producing encapsulated electrophoretic displays of the present invention. Useful materials for simple coacervation processes to form the capsule include, but are not limited to, gelatin, poly(vinyl alcohol), poly(vinyl acetate), and cellulosic derivatives, such as, for example, carboxymethylcellulose. Useful materials for complex coacervation processes include, but are not limited to, gelatin, acacia, carageenan, carboxymethylcellulose, hydrolyzed styrene anhydride copolymers, agar, alginate, casein, albumin, methyl vinyl ether co-maleic anhydride, and cellulose phthalate. Useful materials for phase separation processes include, but are not limited to, polystyrene, poly(methyl methacrylate) (PMMA), poly(ethyl methacrylate), poly(butyl methacrylate), ethyl cellulose, poly(vinylpyridine), and polyacrylonitrile. Useful materials for in situ polymerization processes include, but are not limited to, polyhydroxyamides, with aldehydes, melamine, or urea and formaldehyde; water-soluble oligomers of the condensate of melamine, or urea and formaldehyde; and vinyl monomers, such as, for example, styrene, methyl methacrylate (MMA) and acrylonitrile. Finally, useful materials for interfacial polymerization processes include, but are not limited to, diacyl chlorides, such as, for example, sebacoyl, adipoyl, and di- or polyamines or alcohols, and isocyanates. Useful emulsion polymerization materials may include, but are not limited to, styrene, vinyl acetate, acrylic acid, butyl acrylate, t-butyl acrylate, methyl methacrylate, and butyl methacrylate.

Capsules produced may be dispersed into a curable carrier, resulting in an "ink" which may be printed or coated on large and arbitrarily shaped or curved surfaces using conventional printing and coating techniques.

In the context of the present invention, one skilled in the art will select an encapsulation procedure and wall material based on the desired capsule properties. These properties include the distribution of capsule radii; electrical, mechanical, diffusion, and optical properties of the capsule wall; and chemical compatibility with the internal phase of the capsule.

The capsule wall generally has a high electrical resistivity. Although it is possible to use walls with relatively low resistivities, this may limit performance in requiring relatively higher addressing voltages. The capsule wall should also be mechanically strong (although if the finished capsule powder is to be dispersed in a curable polymeric binder for coating, mechanical strength is not as critical). The capsule wall should generally not be porous. If, however, it is desired to use an encapsulation procedure that produces porous capsules, these can be overcoated in a post-processing step (i.e., a second encapsulation). Moreover, if the capsules are to be dispersed in a curable binder, the binder will serve to close the pores. The capsule walls should be optically clear. The wall material may, however, be chosen to match the refractive index of the internal phase of the capsule (i.e., the suspending fluid) or a binder in which the capsules are to be dispersed. For some applications (e.g., interposition between two fixed electrodes), monodispersed capsule radii are desirable.

One encapsulation technique involves a polymerization between urea and formaldehyde in an aqueous phase of an oil/water emulsion in the presence of a negatively charged, carboxyl-substituted, linear hydrocarbon polyelectrolyte material. The resulting capsule wall is a urea/formaldehyde copolymer, which discretely encloses the internal phase. The capsule is clear, mechanically strong, and has good resistivity properties.

The related technique of in situ polymerization utilizes an oil/water emulsion, which is formed by dispersing the electrophoretic fluid (i.e., the dielectric liquid containing a suspension of the pigment particles) in an aqueous environment. The monomers polymerize to form a polymer with higher affinity for the internal phase than for the aqueous phase, thus condensing around the emulsified oily droplets. In one in situ polymerization process, urea and formaldehyde condense in the presence of poly(acrylic acid) (see, e.g., U.S. Pat. No. 4,001,140). In other processes, described in U.S. Pat. No. 4,273,672, any of a variety of cross-linking agents borne in aqueous solution is deposited around microscopic oil droplets. Such cross-linking agents include aldehydes, especially formaldehyde, glyoxal, or glutaraldehyde; alum; zirconium salts; and polyisocyanates.

The coacervation approach also utilizes an oil/water emulsion. One or more colloids are coacervated (i.e., agglomerated) out of the aqueous phase and deposited as shells around the oily droplets through control of temperature, pH and/or relative concentrations, thereby creating the microcapsule. Materials suitable for coacervation include gelatins and gum arabic. See, e.g., U.S. Pat. No. 2,800,457.

The interfacial polymerization approach relies on the presence of an oil-soluble monomer in the electrophoretic composition, which once again is present as an emulsion in an aqueous phase. The monomers in the minute hydrophobic droplets react with a monomer introduced into the aqueous phase, polymerizing at the interface between the droplets and the surrounding aqueous medium and forming shells around the droplets. Although the resulting walls are relatively thin and may be permeable, this process does not require the elevated temperatures characteristic of some other processes, and therefore affords greater flexibility in terms of choosing the dielectric liquid.

Coating aids can be used to improve the uniformity and quality of the coated or printed electrophoretic ink material. Wetting agents are typically added to adjust the interfacial tension at the coating/substrate interface and to adjust the liquid/air surface tension. Wetting agents include, but are not limited to, anionic and cationic surfactants, and nonionic species, such as silicone or fluoropolymer-based materials. Dispersing agents may be used to modify the interfacial tension between the capsules and binder, providing control over flocculation and particle settling.

Surface tension modifiers can be added to adjust the air/ink interfacial tension. Polysiloxanes are typically used in such an application to improve surface leveling while minimizing other defects within the coating. Surface tension modifiers include, but are not limited to, fluorinated surfactants, such as, for example, the Zonyl (Registered Trade Mark) series from du Pont, the Fluorad (Registered Trade Mark) series from 3M (St. Paul, Minn.), and the fluoroalkyl series from Autochem (Glen Rock, N.J.); siloxanes, such as, for example, Silwet (Registered Trade Mark) from Union Carbide (Danbury, Conn.); and polyethoxy and polypropoxy alcohols. Antifoams, such as silicone and silicone-free polymeric materials, may be added to enhance the movement of air from within the ink to the surface and to facilitate the rupture of bubbles at the coating surface. Other useful antifoams include, but are not limited to, glyceryl esters, polyhydric alcohols, compounded antifoams, such as oil solutions of alkylbenzenes, natural fats, fatty acids, and metallic soaps, and silicone antifoaming agents made from the combination of dimethyl siloxane polymers and silica. Stabilizers such as UV-absorbers and antioxidants may also be added to improve the lifetime of the ink.

D. Binder Material

The binder typically is used as an adhesive medium that supports and protects the capsules, as well as binds the electrode materials to the capsule dispersion. A binder can be non-conducting, semiconductive, or conductive. Binders are available in many forms and chemical types. Among these are water-soluble polymers, water-borne polymers, oil-soluble polymers, thermoset and thermoplastic polymers, and radiation-cured polymers.

Among the water-soluble polymers are the various polysaccharides, the polyvinyl alcohols, N-methylpyrrolidone, N-vinylpyrrolidone, the various Carbowax (Registered Trade Mark) species (Union Carbide, Danbury, Conn.), and poly(2-hydroxyethyl acrylate).

The water-dispersed or water-borne systems are generally latex compositions, typified by the Neorez (Registered Trade Mark) and Neocryl (Registered Trade Mark) resins (Zeneca Resins, Wilmington, Mass.), Acrysol (Registered Trade Mark) (Rohm and Haas, Philadelphia, Pa.), Bayhydrol (Registered Trade Mark) (Bayer, Pittsburgh, Pa.), and the Cytec Industries (West Paterson, N.J.) HP line. These are generally latices of polyurethanes, occasionally compounded with one or more of the acrylics, polyesters, polycarbonates or silicones, each lending the final cured resin in a specific set of properties defined by glass transition temperature, degree of "tack," softness, clarity, flexibility, water permeability and solvent resistance, elongation modulus and tensile strength, thermoplastic flow, and solids level. Some water-borne systems can be mixed with reactive monomers and catalyzed to form more complex resins. Some can be further cross-linked by the use of a cross-linking reagent, such as an aziridine, for example, which reacts with carboxyl groups.

A typical application of a water-borne resin and aqueous capsules follows. A volume of particles is centrifuged at low speed to separate excess water. After a given centrifugation process, for example 10 minutes at 60× gravity ("g"), the capsules are found at the bottom of the centrifuge tube, while the water is at the top. The water is carefully removed (by decanting or pipetting). The mass of the remaining capsules is measured, and a mass of resin is added such that the mass of resin is, for example, between one eighth and one tenth of the weight of the capsules. This mixture is gently mixed on an oscillating mixer for approximately one half hour. After about one half hour, the mixture is ready to be coated onto the appropriate substrate.

The thermoset systems are exemplified by the family of epoxies. These binary systems can vary greatly in viscosity, and the reactivity of the pair determines the "pot life" of the mixture. If the pot life is long enough to allow a coating operation, capsules may be coated in an ordered arrangement in a coating process prior to the resin curing and hardening.

Thermoplastic polymers, which are often polyesters, are molten at high temperatures. A typical application of this type of product is hot-melt glue. A dispersion of heat-resistant capsules could be coated in such a medium. The solidification process begins during cooling, and the final hardness, clarity and flexibility are affected by the branching and molecular weight of the polymer.

Oil or solvent-soluble polymers are often similar in composition to the water-borne system, with the obvious exception of the water itself. The latitude in formulation for solvent systems is enormous, limited only by solvent choices and polymer solubility. Of considerable concern in solvent-based systems is the viability of the capsule itself, the integrity of the capsule wall cannot be compromised in any way by the solvent.

Radiation cure resins are generally found among the solvent-based systems. Capsules may be dispersed in such a medium and coated, and the resin may then be cured by a timed exposure to a threshold level of ultraviolet radiation, either long or short wavelength. As in all cases of curing polymer resins, final properties are determined by the branching and molecular weights of the monomers, oligomers and cross-linkers.

A number of "water-reducible" monomers and oligomers are, however, marketed. In the strictest sense, they are not water soluble, but water is an acceptable diluent at low concentrations and can be dispersed relatively easily in the mixture. Under these circumstances, water is used to reduce the viscosity (initially from thousands to hundreds of thousands centipoise). Water-based capsules, such as those made from a protein or polysaccharide material, for example, could be dispersed in such a medium and coated, provided the viscosity could be sufficiently lowered. Curing in such systems is generally by ultraviolet radiation.

Like other encapsulated electrophoretic displays, the encapsulated electrophoretic displays of the present invention provide flexible, reflective displays that can be manufactured easily and consume little power (or no power in the case of bistable displays in certain states). Such displays, therefore, can be incorporated into a variety of applications and can take on many forms. Once the electric field is removed, the electrophoretic particles can be generally stable. Additionally, providing a subsequent electric charge can alter a prior configuration of particles. Such displays may include, for example, a plurality of anisotropic particles and a plurality of second particles in a suspending fluid. Application of a first electric field may cause the anisotropic particles to assume a specific orientation and present an optical property. Application of a second electric field may then cause the plurality of second particles to translate, thereby disorienting the anisotropic particles and disturbing the optical property. Alternatively, the orientation of the anisotropic particles may allow easier translation of the plurality of second particles. Alternatively or in addition, the particles may have a refractive index that substantially matches the refractive index of the suspending fluid.

An encapsulated electrophoretic display may take many forms. The capsules of such a display may be of any size or shape. The capsules may, for example, be spherical and may have diameters in the millimeter range or the micron range, but are preferably from about ten to about a few hundred microns. The particles within the capsules of such a display may be colored, luminescent, light-absorbing or transparent, for example.

After the foregoing rather lengthy general introduction, the electrophoretic particles, media and displays of the present invention will now be discussed in detail.

Electrophoretic Particles, Media and Displays with Controlled Particle/suspending Fluid Compatibility Hitherto, it has apparently been considered that it is desirable to form the polymer coating or shell around an electrophoretic particle from a polymer which is highly compatible with the suspending fluid surrounding the particle in the electrophoretic medium (typically an aliphatic hydrocarbon such as Isopar G). The use of such a highly compatible polymer shell has been considered desirable to provide good steric stability. Thus, in most of the Examples of the aforementioned 2002/0185378, only a single monomer, and a single polymerization step, are required to provide a sterically stabilizing polymer shell on a colloidally stable, functional pigment. The monomer used to form such polymeric shell is typically lauryl methacrylate, although other monomers are also used in the aforementioned 2002/0185378.

It has now been realized that certain important advantages, especially improved image stability, can be achieved by modifying the polymer shell to make it somewhat less compatible with the suspending fluid, i.e., making some portion of the polymer shell incompatible with the suspending fluid.

The terms "compatible" and "incompatible" are used herein with their meaning in the polymer art. At the simplest level, polymer compatibility with the suspending fluid means that the polymer (when detached from the associated base electrophoretic particle) is soluble in the solvent. Whether a polymer is soluble can usually be determined by simple visual inspection; solutions are generally optically clear, whereas non-solutions (mixtures or dispersions) are opaque or have two obvious phases.

However, compatibility is not a binary phenomenon, that is to say, a polymer is not necessarily totally compatible or totally incompatible with a given suspending fluid. Instead, there is a range of compatibilities, depending on the relative strength of interaction between the fluid and the polymer segments (approximately, the monomers of which the polymer is constituted) and that between the polymer segments themselves. When the polymer is highly soluble in the fluid, polymer-fluid interactions are energetically more favorable than polymer-polymer interactions. In this case, with polymers which tend to form coils, the polymer coil in solution will be extended relative to that of the polymer in a polymer melt. This extension can be measured using capillary viscometry or light scattering techniques. For example, if the intrinsic viscosity, [η], of a series of samples of the polymer having different molecular weights (M) is measured, it is usually found that there is a power-law relationship between the two quantities:

[η]=KM$^\alpha$

The exponent α ranges between 0.5 and about 0.8 (for flexible polymers), depending on the solvent quality, with larger values representing better solvents. When α=0.5, the fluid is called a "theta solvent" and the conformation of the polymer is similar to that in the polymer melt (i.e., surrounded only by other polymer segments), so that in effect the polymer has neutral compatibility with the fluid. Under these conditions the conformation of the polymer chain is that of a random walk.

For both homopolymer and copolymer systems, the Huggins coefficient can be used as an indication of the solvent quality (i.e., of polymer compatibility with the solvent). The Huggins constant is the term [η]$^2$k' in the following expression for the relative viscosity of a dilute solution of a polymer:

$$\frac{\eta}{\eta_s} = 1 + [\eta]c + k'[\eta]^2 c^2 + \ldots$$

In this expression $\eta_s$ is the viscosity of the solvent, [η] is the intrinsic viscosity, and c is the concentration of the polymer in the fluid. For compatible fluids, k' is in the range 0.30 to 0.40, whereas for less compatible fluids, k' is larger (0.50 to 0.80). (see C. W. Macosko, *Rheology Principles, Methods, and Applications*, VCH Publishers, 1994, p. 481).

Similar information can be gleaned from the value of the second virial coefficient for a given fluid-polymer solution as measured by static light scattering or osmometry. Generally, large second virial coefficients mean more compatible fluids. In the case of association between dissolved polymers, corresponding to substantially incompatible polymer-solvent interactions, the second virial coefficient can even become negative (see C. Tanford, *Physical Chemistry of Macromolecules*, John Wiley and Sons, New York, 1961, pp. 293-296).

When a polymer is not soluble in a fluid, i.e., it is incompatible, the polymer sometimes can still be swollen by the fluid. The degree of swelling (the ratio of the volume of a polymer sample in the presence of fluid to that of the dry polymer) can be used as a measure of the degree of compatibility of the fluid and polymer in this regime. The greater the degree of swelling, the greater the compatibility.

Making the polymer shell less compatible with the suspending fluid can be achieved in several ways. Firstly, the polymer shell may have repeating units derived from at least one monomer the homopolymer of which is incompatible with the suspending fluid, in accordance with the incompatible monomer electrophoretic medium aspect of the present invention. Typically, such a polymer shell will also include a compatible monomer, that is to say a monomer the homopolymer of which is compatible with the suspending fluid, and the compatibility of the polymer shell with the suspending fluid can be adjusted by varying the ratio of the two monomers.

A polymer shell including both an incompatible and a compatible monomer (obviously, there may be more than one monomer of each type present) can be a random copolymer shell formed by using a mixture of polymerizable monomers in the last polymerization step (which may be the sole polymerization step). If one of the monomers is compatible with the suspending fluid, and one is not, a range of colloidal stabilities can be built into the particle depending on the ratio of the monomers in the shell. Further, since different monomer species can impart different degrees of incompatibility, by changing the incompatible monomer, the degree of incompatibility can be further modified. For example, it has been observed that, when used as the sole monomer in a polymer shell, acrylate esters with short side chains containing not more than about eight carbon atoms (e.g., butyl methacrylate) yield particles that are not colloidally stable in an Isopar G suspending fluid. On the other hand, lauryl methacrylate yields electrophoretic particles with excellent colloidal stability in Isopar G. Therefore, a copolymer of lauryl methacrylate and butyl methacrylate will give a polymer shell marginally compatible with Isopar G, and a marginally colloidally stable particle, at some mole ratio of butyl methacrylate to laurel methacrylate in the polymerization mixture.

A second method of modifying the polymer shell around the electrophoretic particles is by a second stage of polymerization. Experiments have shown that the surface functionality provided by the reagents of Formulae (I) and (II) above is not completely consumed during a single graft polymerization step. For example, if titania, surface functionalized and polymer coated, is simply re-suspended in a polymerization medium (typically comprising toluene, lauryl methacrylate and azobisisobutyronitrile (AIBN) as a polymerization initiator), thermogravimetric analysis of the pigment isolated from the reaction mixture after heating for 16 hours shows an increase in the amount of bound polymer (as determined by thermogravimetric analysis (TGA): after first polymerization: 7.3%; after second polymerization: 8.9% and 9.9% in two different runs). In such a double graft polymerization process, the monomer used in the second polymerization can be different from that used in the first, thus making it possible to incorporate polymer chains constructed from different monomers in the final polymer shell. Furthermore, by modifying the conditions of the first polymerization step, the initial grafting density of chains can be adjusted, as well as the availability (and accessibility) of the surface vinyl functionality for the second stage polymerization. Thus, this double polymerization method affords a second degree of flexibility in the construction of polymer stabilized electrophoretic particles. It may be beneficial to adjust the molecular weight of the polymer chains in either the first or second polymerization stage by the incorporation of chain transfer agents into the polymerization mixture, or by adjusting the concentrations of monomer or radical initiator in ways well known in the polymer art.

Since the presently aliphatic hydrocarbon preferred suspending fluids are generally considered to be poorly compatible with many homopolymers, a very large range of readily available monomers are available for use as incompatible monomers in polymer shells produced by either of the two methods described above. Such incompatible monomers include acrylate esters with alkyl groups that vary in chain length and branching structure but typically have eight or fewer carbon atoms (e.g. methyl methacrylate, ethyl methacrylate, butyl methacrylate, isobutyl methacrylate, t-butyl methacrylate, octyl methacrylate, 2-ethylhexyl methacrylate), as well as the corresponding esters of acrylic acid, acrylates with fluorocarbon ester side chains, acrylate esters of functional alcohols, for example, 2-hydroxyethyl methacrylate, acrylamides, such as acrylamide, methacrylamide, N-monoalkyl acrylamides and methacrylamides, N,N-dialkylacrylamides, N-vinylpyrrolidone, and functional acrylamide derivatives, styrene, substituted styrene derivatives, vinyl acetate and other vinyl esters, halogenated vinyl derivatives (vinyl chloride, vinylidene chloride, etc.) and other polymerizable monomer species.

Although the present invention is in no way limited by theoretical considerations, it is possible to provide a rational explanation for the improved properties of electrophoretic media in which the polymer shells around the particles contain incompatible monomers. A polymer shell formed entirely from compatible monomers provides steric stability to the electrophoretic particle because it is thermodynamically favorable for the polymer chains forming the shell to be surrounded by suspending fluid rather than by other polymer segments. Thus, a polymer shell formed entirely from compatible monomers, for example a pure poly(lauryl methacrylate) polymer shell dispersed in an aliphatic hydrocarbon, is highly swollen. Because interpenetration of shells on adjacent particles increases the number of polymer-polymer contacts relative to more favorable polymer-solvent contacts, there is an effective repulsive force between the particles, and they tend to stay spaced from one another and thus dispersed in the suspending fluid. Polymer shells formed from completely incompatible monomers do not provide such steric stability, because it is thermodynamically favorable for the polymer chains forming the shell to be surrounded by other polymer segments rather than by suspending fluid, so that the polymer shell collapses, excluding suspending fluid, and the electrophoretic particles tend to be attracted to one another and hence tend to aggregate. In other words, highly compatible polymer shells favor dispersion of the electrophoretic particles through the suspending fluid, while incompatible polymer shells favor aggregation of the electrophoretic particles. The image stability of electrophoretic media is favored by a tendency of the electrophoretic particles to aggregate, since in each of the types of electrophoretic media illustrated in FIGS. 1 to 3, the stability of an image once written is dependent upon the ability of the electrophoretic particles to remain aggregated with similar electric particles in the homoaggregate (layer) of particles responsible for the image. (note that FIGS. 1 to 3 are simplified; in practice, there will normally be more than one layer of particles in particle aggregates formed during imaging.) By adjusting the compatibility of the polymer shell and the suspending fluid by incorporating both compatible and incompatible monomers into the polymer shell, it is possible to adjust the overall compatibility of the polymer shell with the suspending fluid, and the stability of aggregates of such particles, and hence the image stability of the resulting display.

One further advantage of preferred embodiments of the present invention is the introduction of a threshold for the switching of the electrophoretic medium. If the attraction of the electrophoretic particles for each other, and hence their tendency to remain in stable homoaggregates, is sufficiently strong, it will require an appreciable field to pull the particles out of the homoaggregate so that they can migrate in the field. The existence of an appreciable threshold voltage for switching of the electrophoretic medium has a number of advantages. If the threshold is sufficiently large, it can enable the use of passive matrix addressing of a high resolution display. Smaller thresholds may be useful for reducing the sensitivity of an active matrix display to parasitic voltages and inter-pixel voltage leakage.

The present invention also provides an additional approach to improving image stability in a dual particle electrophoretic medium. In a dual particle electrophoretic medium, it is necessary that both types of electrophoretic particles contribute to the overall image stability. It is not sufficient that one type of particle be "image stable" (that is, remain in a homoaggregate in the location to which it has been switched) if the second type of particle is free to settle or diffuse through the suspending fluid. If such is the case, one extreme optical state of the medium might show reasonably good image stability, but the other would display poor stability. Also if the particles can diffuse, poor image stability of one particle could easily contribute to optical degradation of the second extreme optical state as well. It is therefore desirable that both types of particles have steric stabilities that are appropriately adjusted to give good image stability. If one attempts to use a "depletion flocculation" approach to achieving good image stability by including a polymer in the suspending fluid (see the aforementioned 2002/0180687), the degree to which the depletion mechanism applies to the two types of particles is different depending on the particle size and particle geometry, and is not independently adjustable, since only one polymer is added to the suspending fluid and used to impart image stability to both types of particles. However, in the incompatible monomer electrophoretic medium of the present invention, the colloidal stability of each type of particle can be adjusted independently. Furthermore, adding a polymer to the suspending fluid in accordance with the depletion flocculation approach may make the two separate types of particles colloidally unstable with respect to each other as well as to themselves, thus encouraging heteroaggregation of the two types of particles. Heteroaggregation may cause a number of undesirable effects in a dual particle electrophoretic display, including slower response time and the requirement for the use of higher applied voltages (since a higher field strength will be required to separate the heteroaggregate) as well as poor optical states (since charged heteroaggregates may not be completely separated by the applied field if there is a large majority of particles of one type therein).

In accordance with the homoaggregation medium aspect of the present invention, these problems are eliminated, or at least reduced, by providing a dual particle electrophoretic medium in which homoaggregation of the two types of particles is thermodynamically favored over heteroaggregation. This can be achieved by providing the two types of particles with polymer shells that having their compatibility with the suspending fluid adjusted to favor homoaggregation, but also adjusting the compatibility of the two types of polymer shells to disfavor heteroaggregation. This is relatively easy to achieve by using different incompatible monomers in the polymer shells of the two types of particles; typically, the same compatible monomer can be used for the polymer shells on both types of particles. If the two incompatible monomers are not mutually compatible, then the tendency of the two types of particles to heteroaggregate will be minimal, and only homoaggregation encouraged, thus providing more rapid response time and purer optical states of the electrophoretic medium.

As already mentioned above, the present invention is not restricted to the use of aliphatic hydrocarbons as suspending fluids. Fluoro- and halocarbon oils, silicone oils, aralkyl solvents (e.g., toluene, dodecylbenzene and the like) or mixtures thereof may be useful in this invention, since they allow further modification of the properties of the suspending fluid with respect to salvation of polymer shells, as described above.

The present invention can be applied to all types of electrophoretic media, but may be especially useful in encapsulated electrophoretic media, whether using pre-formed capsules or microcells. This invention can also be applied to displays with all types of switching geometries, including both forward and back, as well as side-to-side and shutter mode switching.

Figure 7:
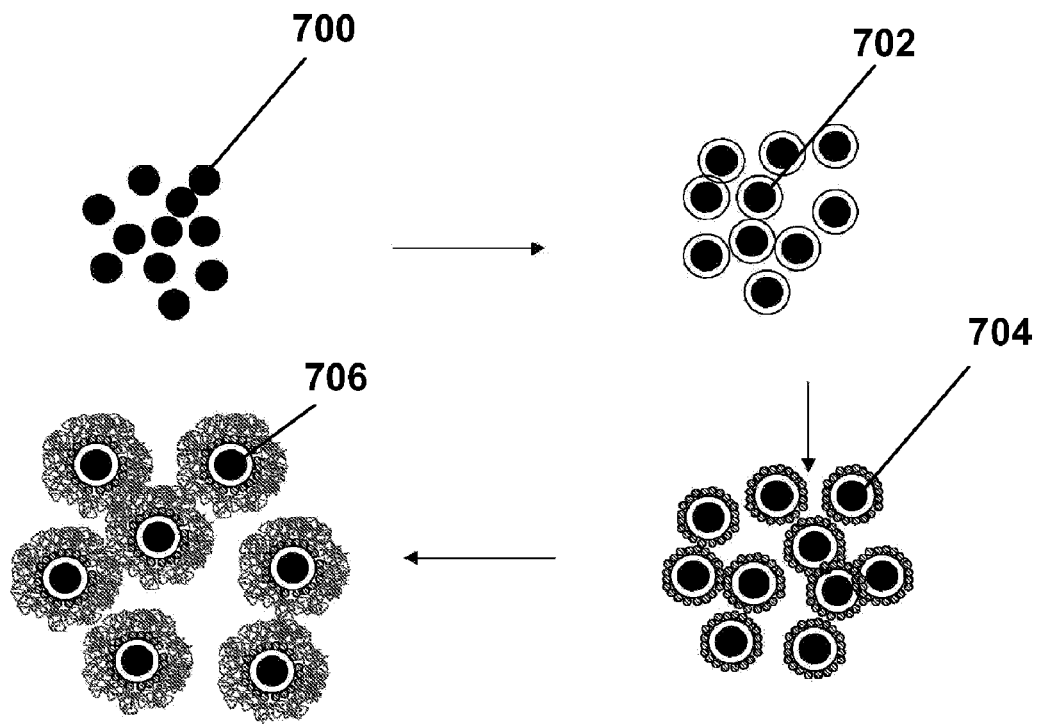
FIG. 7 is a reaction diagram showing schematically the process used to produce an incompatible monomer electrophoretic particle of the present invention.

FIG. 7 of the accompanying drawings shows schematically a preferred process, as used in the Examples below, for preparing electrophoretic particles in accordance with the present invention, this process being essentially similar to that described in the aforementioned 2002/0185378. In the first stage of the process, a base pigment particle 700 is coated with silica to produce a silicated pigment 702; this step is fully described in the aforementioned 2002/0185378. Next, the silicated pigment 702 is treated with a bifunctional reagent having one functional group which reacts with the silica surface, and a second, charge control group, thus producing a surface functionalized pigment 704 bearing charge control groups on its surface. The bifunctional reagent also provides a site for the formation of polymer on the pigment particle. Finally, as shown in FIG. 7, the surface functionalized pigment 704 is contacted with one or more monomers or oligomers under conditions effective to cause formation of polymer attached to the charge control groups, thereby producing a polymer-coated functional pigment 706, which is used in the electrophoretic medium.

The following Examples are now given, though by way of illustration only, to illustrate the synthesis of several different electrophoretic particles of the present invention having polymer shells with controlled compatibility with suspending fluid, and to illustrate the advantages achieved by such electrophoretic particles.

The experiments in these Examples will be described using an abbreviated notation, as follows. These experiments used a white titania pigment based on du Pont Ti-Pure R960 and a black copper chromite pigment based on Shepherd Black 1G. These particles were surface functionalized according to the reaction scheme of FIG. 7 using Z6030 for the white pigment and the reagent of Formula (I) above for the black, and then had polymer shells formed thereon in the manner described below. The white particles thus produced were negatively charged when incorporated into an Isopar G suspending fluid including Solsperse 17K and Span as charging agents and the black particles were positively charged. Particles were prepared with lauryl methacrylate homopolymer shells as a control experiment and are referred to by the letters J and D for white particles and black particles respectively. Modifications of the polymer shell are described as follows: for particles made using a random copolymer, one-stage polymerization, the comonomer is identified by the letter codes indicated in Table I below in parentheses after the appropriate pigment indicator together with a number indicating the mole fraction of the comonomer used in the polymerization reaction. The remainder in each case was lauryl methacrylate. Thus, the notation J(BMA15) indicates a white pigment made from a polymerization mixture comprising 15 mole % t-butyl methacrylate and 85 mole % lauryl methacrylate. A two-stage polymerization is indicated by a plus sign; in general, the mole ratio of polymers for these particles is not so well known, so that no indication is given about composition. Thus J(+St) indicates a white pigment made by a two-stage polymerization. The starting material was the control pigment in this case, with 100 mole percent lauryl methacrylate used in the first stage polymerization; the second stage polymerization was carried out using only styrene as the polymerizable monomer.

TABLE 1

| Monomer | Shorthand symbol |
|---|---|
| Styrene | St |
| t-butyl methacrylate | TBMA |
| vinyl pyrrolidone | VP |

The procedures used for formation of the polymer shells, and for incorporation of the resultant polymer-coated particles into electrophoretic media and displays, were as follows. All centrifuging mentioned was carried out on a Beckman GS-6 or Allegra 6 centrifuge (available from Beckman Coulter, Inc., Fullerton, Calif. 92834).

1. Standard Lauryl Methacrylate Polymerization

A single-neck, 250 mL round bottomed flask was equipped with a magnetic stir bar, reflux condenser and an argon/or nitrogen inlet and placed in a silicon oil bath. To the flask was added 60 g of silane-coated pigment which was pulverized into a fine powder using a mortar and pestle, followed by 60 mL of lauryl methacrylate (LMA, Aldrich) and 60 mL of toluene. The reaction mixture was then stirred rapidly and the flask purged with argon or nitrogen for one hour. During this time the silicon bath was heated to 50° C. During the purge, 0.6 g of AIBN (2,2'-azobisisobutyronitrile, Aldrich) was dissolved in 13 mL of toluene. At the end of the one hour purge the AIBN/toluene solution was added quickly with a glass pipette. The reaction vessel was sealed, heated to 65° C. and allowed to stir overnight. At the end of the polymerization, to the viscous reaction mixture was added 100 mL of ethyl acetate and the mixture allowed to stir for another 10 minutes. The mixture was poured into plastic bottles and centrifuged for 15-20 minutes at 3600 rpm and decanted. Fresh ethyl acetate was added to centrifuged pigment, which was stirred with a stainless steel spatula and sonicated for 10 minutes. The pigment was washed twice more with ethyl acetate following the above procedure. The pigment was allowed to air dry overnight followed by drying under high vacuum for 24 hours. The free polymer in bulk solution was precipitated in methanol and dried under vacuum. The molecular weight of free polymer in the solution was determined by gas phase chromatography (GPC). The polymer bound on the pigment was measured by TGA.

2. Co-polymerization on Titania

A single-neck, 250 mL round bottomed flask was equipped with a magnetic stir bar, reflux condenser and an argon/or nitrogen inlet and placed in a silicon oil bath. To the flask were added 60 ml of toluene, 60 g of titania (Z6030 coated Dupont R960), lauryl methacrylate (LMA) and a second monomer, such as styrene, t-butyl methacrylate, 1-vinyl-2-pyrrolidinone, hexafluorobutyl acrylate and methacrylate, N-isopropylacrylamide or acrylonitrile (Aldrich), the amounts of LMA and second monomer depending on the desired monomer ratio. The ratios of LMA/second monomer were usually 95/5, 85/15 and 75/25. The reaction mixture was then stirred rapidly and the flask purged with argon or nitrogen for one hour. During this time the silicon bath was heated to 50° C. During the purge, 0.6 g of AIBN was dissolved or partially dissolved in 13 mL of toluene. At the end of the one hour purge the AIBN/toluene solution was added quickly with a glass pipette. The reaction vessel was sealed, heated to 65° C. and allowed to stir overnight. To the viscous reaction mixture was added 100 mL of ethyl acetate and the resultant mixture was allowed to stir for another 10 minutes. The mixture was poured into plastic bottles and centrifuged for 15-20 minutes at 3600 rpm and decanted. Fresh ethyl acetate was added to the centrifuged pigment, and the resultant mixture stirred with a stainless steel spatula and sonicated for 10 minutes. The pigment was washed twice more with ethyl acetate, centrifuged and decanted. The pigment was allowed to air dry overnight followed by drying under high vacuum for 24 hours. The free polymer in bulk solution was precipitated in methanol and dried under vacuum. The molecular weight of free polymer in the solution was determined by GPC. The polymer bound on the pigment was measured by TGA.

2.1 LMA and 1-vinyl-2-pyrrolidinone Copolymerization on Titania

A single-neck, 250 mL round bottomed flask was equipped with a magnetic stir bar, reflux condenser and an argon/or nitrogen inlet and placed in a silicon oil bath. To the flask were added 60 mL of toluene, 60 g of titania (Z6030 coated Dupont R960), 51 mL of lauryl methacrylate (LMA) and 3.3 mL of 1-vinyl-2-pyrrolidinone. The mole ratio of LMA/1-vinyl-2-pyrrolidinone is usually 85/15. The reaction mixture was then stirred rapidly and the flask purged with argon or nitrogen for one hour. During this time the silicon bath was heated to 50° C. During the purge, 0.6 g of AIBN was dissolved or partially dissolved in 13 mL of toluene. At the end of the one hour purge the AIBN/toluene solution was added quickly with a glass pipette. The reaction vessel was sealed, heated to 65° C. and allowed to stir overnight. To the viscous reaction mixture was added 100 mL of ethyl acetate and the resultant mixture was allowed to stir for another 10 minutes. The mixture was poured into plastic bottles and centrifuged for 15-20 minutes at 3600 rpm and decanted. Fresh ethyl acetate was added to the centrifuged pigment, and the resultant mixture was stirred with a stainless steel spatula and sonicated for 10 minutes. The pigment was washed twice more with ethyl acetate, centrifuged and decanted. The pigment was allowed to air dry overnight followed by drying under high vacuum for 24 hours. The free polymer in bulk solution was precipitated in methanol and dried under vacuum. The molecular weight of free polymer in the solution was determined by GPC. The polymer bound on the pigment was measured by TGA.

3 Two Stage Polymerization using LMA-coated White Pigment

A single-neck, 250 mL round bottomed flask was equipped with a magnetic stir bar, reflux condenser and an argon/or nitrogen inlet and placed in a silicon oil bath. To the flask was added 60 g of silane coated pigment which was pulverized into a fine powder using a mortar and pestle, followed by 60 mL of lauryl methacrylate and 60 mL of toluene. The reaction mixture was then stirred rapidly and the flask purged with argon or nitrogen for one hour. During this time the silicon bath was heated to 50° C. During the purge, 0.6 g of AIBN was dissolved in 13 mL of toluene. At the end of the one hour purge the AIBN/toluene solution was added quickly with a glass pipette. The reaction vessel was sealed, heated to 65° C. and allowed to stir overnight. At the end of the polymerization, to the viscous reaction mixture was added 100 mL of ethyl acetate and the resultant mixture was allowed to stir for another 10 minutes. The mixture was poured into plastic bottles and centrifuged for 15-20 minutes at 3600 rpm and decanted. Fresh ethyl acetate was added to the centrifuged pigment, and the resultant mixture stirred with a stainless steel spatula. The pigment was washed twice more with ethyl acetate following the above procedure. The pigment was allowed to air dry overnight followed by drying under high vacuum for 24 hours. The free polymer in bulk solution was precipitated in methanol and dried under vacuum. The molecular weight of free polymer in the solution was determined by GPC. The polymer bound on the pigment was measured by TGA.

Note that in the foregoing procedure, the sonication used in the procedures described above was omitted in order to avoid any possible damage to ethylenic groups remaining on the pigment surface after the first stage polymerization already described.

To effect the second stage polymerization, another single-neck, 250 mL round bottomed flask was equipped with a magnetic stir bar, reflux condenser and an argon/or nitrogen inlet and placed in a silicon oil bath. To the flask was added 50 g of LMA-coated pigment prepared as described above, which was pulverized into a fine powder using a mortar and pestle, followed by 85 mL of toluene and 16 g of styrene. The reaction mixture was then stirred rapidly and the flask purged with argon or nitrogen for one hour. During this time the silicon bath was heated to 50° C. During the purge, 0.4 g of AIBN was dissolved in 10 mL of toluene. At the end of the one hour purge the AIBN/toluene solution was added quickly with a glass pipette. The reaction vessel was sealed, heated to 65° C. and allowed to stir overnight. At the end of polymerization, to the viscous reaction mixture were added 100 mL of ethyl acetate and the resultant mixture was allowed to stir for another 10 minutes. The mixture was poured into plastic bottles and centrifuged for 15-20 minutes at 3600 rpm and decanted. Fresh ethyl acetate was added to the centrifuged pigment, and the resultant mixture was stirred with a stainless steel spatula and sonicated for 10 minutes. The pigment was washed twice more with ethyl acetate following the above procedure. The pigment was allowed to air dry overnight followed by drying under high vacuum for 24 hours. The free polymer in bulk solution was precipitated in methanol and dried under vacuum. The molecular weight of free polymer in the solution was determined by GPC. The polymer bound on the pigment was measured by TGA.

4 Copolymerization on Coated Copper Chromite

A single-neck, 250 mL round bottomed flask was equipped with a magnetic stir bar, reflux condenser and an argon inlet and placed in a silicon oil bath. To the flask was added 60 g of copper chromite ($CuCr_2O_4$, Shepherd Black 1G) coated with the silane of Formula (I) above, which had pulverized into a fine powder using a mortar and pestle, followed by 1.2 mL of styrene, 57 mL of lauryl methacrylate and 60 mL of toluene. The reaction mixture was then stirred rapidly and the flask purged with argon or nitrogen for one hour and the silicon bath was heated to 50° C. During the purge, 0.6 g of AIBN was dissolved or partially dissolved in 13 mL of toluene. At the end of the one hour purge the AIBN/toluene solution was added quickly with a glass pipette. The reaction vessel was sealed, heated to 65° C. and allowed to stir overnight. To the viscous reaction mixture was added 100 mL of ethyl acetate and the resultant mixture was allowed to stir for another 10 minutes. The mixture was poured into plastic bottles and centrifuged for 15-20 minutes at 3600 rpm and decanted. Fresh ethyl acetate was added to the centrifuged pigment, and the resultant mixture was stirred with a stainless steel spatula and sonicated for 10 minutes. The pigment was washed twice more with ethyl acetate, centrifuged and decanted. The pigment was allowed to air dry overnight followed by drying under high vacuum for 24 hours. The free polymer in bulk solution was precipitated in methanol and dried under vacuum. The molecular weight of free polymer in the solution was determined by GPC. The polymer bound on the pigment was measured by TGA.

Preparation of Control Internal Phase (Electrophoretic Particles Plus Suspending Fluid)

A control internal phase was formulated from (a) 85 g of a stock solution of the J pigment containing 60% by weight of LMA-coated titania in Isopar G; (b) 42.5 g of a stock solution of the D pigment containing 60% by weight of LMA-coated copper chromite in Isopar G; (c) 10.71 g of a stock solution containing 10% by weight of Solsperse 17000 in Isopar G; (d) 31.03 g of Isopar G; and (e) 0.77 g Span 85 (a non-ionic surfactant).

To a 250 ml plastic bottle were added the J and D stock solutions, followed by the addition of the Solsperse 17000 solution and the Span 85 2220 and finally the remaining solvent. The resultant internal phase was shaken vigorously for approximately 5 minutes and then placed on a roll mill overnight (at least 12 hours).

Preparation of Internal Phase using White Pigment of this Invention and Prior Art Black Pigment An internal phase was formulated from (a) 40 g of a stock solution of a modified J pigment containing 60% by weight of an LMA/TBMA-coated titania (mole ratio 85/15) in Isopar G; (b) 20 g of a stock solution of the D pigment containing 60% by weight of LMA-coated copper chromite in Isopar G; (c) 5.04 g of a stock solution containing 10% by weight of Solsperse 17000 in Isopar G; (d) 14.60 g of Isopar G; and (e) 0.36 g Span 85 (a non-ionic surfactant).

This internal phase was mixed and stored in the same way as the previous internal phase described above.

Preparation of Internal Phase using Prior Art White Pigment and Black Pigment of this Invention An internal phase was formulated from (a) 40 g of a stock solution of the same J pigment as in the control internal phase, this stock solution containing 60% by weight of an LMA-coated titania in Isopar G; (b) 20 g of a stock solution of the D pigment containing 60% by weight of LMA/St-coated copper chromite (85/15 or 95/5 monomer ratio) in Isopar G; (c) 5.04 g of a stock solution containing 10% by weight of Solsperse 17000 in Isopar G; (d) 14.60 g of Isopar G; and (e) 0.36 g Span 85 (a non-ionic surfactant).

This internal phase was mixed and stored in the same way as the previous internal phase described above.

The internal phases thus produced were encapsulated (separately) in gelatin/acacia microcapsules substantially as described in Paragraphs [0069] to [0074] of the aforementioned 2002/0180687. The resultant microcapsules were separated by size and capsules having an average particle size of about 35 μm were used in the following experiments. The microcapsules were mixed into a slurry with a polyurethane binder and coated by a roll-to-roll process at a dry coating weight of 18 g m$^{-2}$ on to the surface of a 7 mil (177 μm) poly(ethylene terephthalate) (PET) film carrying an indium tin oxide (ITO) layer on one surface, the microcapsules being deposited on the ITO-covered surface, substantially as described in Paragraphs [0075] and [0076] of the aforementioned 2002/0180687. The capsule-bearing film was then formed into a front plane laminate by laminating it to a layer of a polyurethane lamination adhesive carried on a release sheet, this lamination being effected at 65 psig (0.51 mPa) at a speed of 6 inches/min (2.5 mm/sec) using a Western Magnum twin roll Laminator with both rolls held at 120° C. To provide experimental single-pixel displays suitable for use in these experiments, pieces of the resultant front plane laminate has their release sheets removed and were then laminated at 75° C. to a 5 cm by 5 cm PET film covered with a carbon black layer, which served as the rear electrode of the single pixel display.

Image Stability Measurements

The single pixel displays thus produced were switched using a 500 msec square wave pulse at 10 V of alternating sign applied to the top plane (ITO layer) relative to the grounded rear electrode. A rest period of 2 seconds between pulses was used for shakeup switches. Image stability was measured by switching the pixel to the appropriate optical state (white or black), grounding the top plane, and measuring the optical reflectivity continuously for 10 minutes. Optical kickback resulting from remnant voltages in the binder and lamination adhesive layers was assumed to decay in 5-10 seconds. The difference in optical state (measured in L* units) between 5 seconds and 10 minutes was taken to be a measure of the image stability. The results shown in Table 2 below were obtained on selected pixels.

TABLE 2

| Pigments | Example No. | White state IS (dL*) | Black state IS (dL*) |
|---|---|---|---|
| J/D (control) | 1 | −6.3 | 2.7 |
| J(TBMA5)/D | 2 | −2.2 | 2.1 |
| J(TBMA15)/D | 3 | −4.2 | 1.1 |
| J/D(St5) | 4 | −4.7 | 2.0 |
| J/D(St15) | 5 | −4.7 | 1.6 |
| J(TBMA5)/D(St15) | 6 | −3.3 | 1.7 |
| J(TMBA15)/D(St5) | 7 | −1.6 | 3.0 |
| J(+St)/D | 8 | −2.2 | 0.3 |

The control pixel shows relatively good black state stability, but rather poor white state stability (similar displays using carbon black instead of copper chromite as the black pigment and without PIB in the suspending fluid show much worse state stability, of the order of 10-15L* in both white and dark states). Any of the electrophoretic pigments of the invention results in an improvement in the image stability relative to the control, either in white state or black state or in both. Only in one case is the image stability of a pixel of the invention less good than the control (J(TBMA15)/D (St5)), and here the difference is probably within experimental pixel-to-pixel variation. The best overall image stability is afforded by the display made with white pigment synthesized using the two-stage method, with styrene as the second monomer. This display has good image stability in the white state, and excellent image stability in the black state.

Response Time

The response time of the electrophoretic displays shown in Table 2 was measured by measuring the electro-optic response as a function of pulse length at an operating voltage of 10 V. A rest length of 2000 msec was used for all measurements. The electro-optic response, as measured by the difference in L* between the white state and the dark state, was found to saturate at a certain pulse length, and then decline slightly at longer pulse lengths. The control samples were a pixel with the same formulation as the control in Table 2, and similar pixels containing 0.3 and 0.9% by weight high molecular weight PIB as a means of achieving good image stability. Table 3 shows the pulse length at which the electro-optic response achieves 90% of its value with a 1 second pulse length for the displays of Table 2.

TABLE 3

| Pigments | Example No. | Time to 90% saturation (msec) |
|---|---|---|
| J/D (control-no PIB) | 1 | 294 |
| J(TBMA5)/D | 2 | 173 |
| J(TBMA15)/D | 3 | 281 |
| J/D(St5) | 4 | 325 |
| J/D(St15) | 5 | 375 |
| J(+St)/D | 8 | 380 |
| J/D + 0.9% PIB (control) | 9 | 740 |
| J/D + 0.3% PIB (control) | 10 | 575 |

The control samples containing PIB had response times that were substantially longer than those of samples in accordance with the present invention. At least 0.3% PIB is required to obtain adequate image stability in this system, and 0.9% PIB is preferred. Thus the methods of the invention achieve good image stability with response times between 1.5 and 4 times faster than the control samples.

Voltage Thresholds

Figure 8:
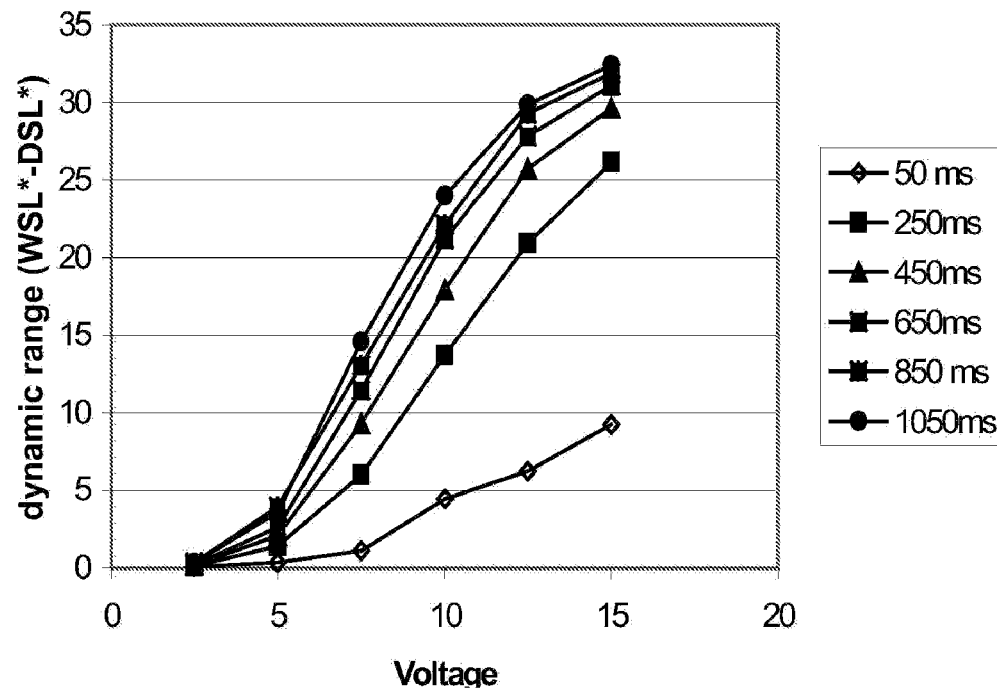
FIG. 8 is a graph showing the variation of the dynamic range of a homoaggregation electrophoretic medium of the present invention as a function of the applied voltage for various pulse lengths, as described in the Examples below.

The pixel described above using white pigment with 5 mole % TBMA and black pigment with 15 mole % styrene in their polymer shells, in addition to relatively good image stability, also displayed a large threshold for operation. The threshold voltage is shown in FIG. 8, which shows the dynamic range of the pixel as a function of the applied voltage for a number of pulse lengths. The dynamic range is very small (of the order of 1 L*) for applied voltages less than 4-5 volts, independent of the pulse length, but a good dynamic range (greater than 30 L*) is exhibited at impulses greater than 600 msec and 10 V.

From the foregoing, it will be seen that the incompatible monomer, particles, media and displays, and the homoaggregation medium, of the present invention provide good image stability and has a number of advantages over similar media containing polymer additives in the suspending fluid, especially since the present invention does not sacrifice response time to achieve good image stability. This advantage in response time can be used to operating a display at lower voltage. The displays reported in Table 2 switch almost to saturation in 300 msec at 7.5V, and achieve optimal contrast ratio at 10V and 250-300 msec. At 15 volts, switching times of around 100 msec can be achieved.

Aliphatic Polymerization Process

As already mentioned, it has been found that the graft polymerization steps described in the aforementioned 2002/0185378 and above can be carried out in aliphatic hydrocarbons, especially isoparaffin solvents; a preferred solvent for this purpose is Isopar G, sold by Exxon Mobil Corporation, Houston Tex. Since such aliphatic hydrocarbons are the same materials typically used as the suspending fluids of electrophoretic media, the coated pigment can remain in essentially the same environment from the graft polymerization step until its incorporation into the final display.

At the conclusion of the graft polymerization step, the aliphatic hydrocarbon solvent may contain any one or more of excess polymerization initiator, excess monomer or oligomer, and free polymer not attached to pigment particles. These materials need to be substantially removed from the pigment particles before the pigment particles are incorporated into the final electrophoretic medium, since the materials may adversely affect the electro-optic properties and/or operating lifetime of the medium. Accordingly, it will typically still be necessary to separate the polymer-coated pigment from the graft polymerization solvent, for example by centrifugation, and to wash the pigment particles to remove the last traces of the aforementioned materials. However, it is not necessary to dry the polymer-coated pigment to remove the last traces of hydrocarbon solvent therefrom (so that the pollution control problems associated with solvent vapors are eliminated), nor is it necessary to re-disperse dry pigment in an aliphatic halocarbon solvent; since, at the conclusion of the washing step, the pigment is already wet with the aliphatic hydrocarbon solvent, re-dispersion of the pigment in the larger quantity of solvent needed in the final electrophoretic medium will present no difficulties. Obviously, if the polymerization could be carried out a manner which left only minimal amounts of the aforementioned materials present in the graft polymerization solvent after completion of the polymerization, in principle it would be possible to eliminate the separation and washing of the polymer-coated pigment.

There do not appear to be any inherent obvious differences between polymer-coated pigments produced in an aliphatic hydrocarbon solvent according to the present invention and those produced in toluene according to the prior art process, although some experiments appear to indicate that the pigments produced in the aliphatic hydrocarbon solvent tend to have higher polymer contents.

As mentioned earlier, the suspending fluid in the electrophoretic medium is normally an aliphatic hydrocarbon, alone or in combination with a halocarbon. If the suspending fluid is to be a mixture of an aliphatic hydrocarbon and a halocarbon, it is at present preferred to carry out the graft polymerization in the aliphatic hydrocarbon alone, since after washing there is no difficulty in re-dispersing pigment wet with aliphatic hydrocarbon in a mixture of an aliphatic hydrocarbon and a halocarbon. However, we do not exclude the possibility that the graft polymerization might itself be carried out in a mixture of an aliphatic hydrocarbon and a halocarbon.

When a dual particle electrophoretic medium is being prepared (for example, a medium containing white titania particles and carbon black particles), the process of the present invention can be applied to the two types of particles separately. However, provided that the two types of particles are to provided with similar types of polymer coatings, the present invention may also be practiced by first blending the two types of pigment after providing polymerizable groups thereon, and then carrying out the graft polymerization step on this pigment mixture. Thus, the two pigments travel together through the remaining steps required to form the electrophoretic medium. Indeed, the mixed polymer-coated pigment resulting from this process can be regarded as a stock solution of pigment that may require little or no further processing after washing to remove residual impurities. This variant of the present process thus further reduces the number of discrete steps which need to be carried out to convert raw pigments to the final electrophoretic medium.

The process of the present invention decreases the safety hazards associated with the prior art processes, since the aliphatic hydrocarbon solvents used in the present process are less hazardous than toluene and THF. As already mentioned, the present process reduces solvent use, and also reduces the number of steps in the overall process for producing electrophoretic media, since it eliminates the previous drying and pigment re-dispersion steps, thus decreasing dispersion processing time and possibly increasing the overall quality of the final dispersion of pigments in aliphatic hydrocarbon solvent.

Another aspect of the present invention relates to controlling the relative sizes and masses of particles in an electrophoretic medium in order to reduce the tendency for the electrophoretic particles to agglomerate.

It is known that, in electrophoretic media, and especially in dual particle electrophoretic media, the particles show a tendency to aggregate. This tendency may be especially troublesome in dual particle electrophoretic media in which the two types of particles bear charges of opposite polarity because there is a natural tendency for any particles bearing opposing electrical charges to stick together. Such particle agglomeration reduces the contrast of the display; for example, if black and white particles agglomerate to form gray particles which do not separate when an electric field is applied to change the optical state of the display, the supposedly pure black or white optical states of the display will be contaminated with gray agglomerates, thus reducing contrast ratio. In addition, severe and persistent agglomeration may eventually prevent the display from functioning, thus reducing the operating lifetime of the display.

It has now been realized that the relative motion of two types of particles in a dual particle electrophoretic medium can be used to break up agglomerates and hence reduce the problems associated with such agglomerates. Introduction into the electrophoretic medium of a second kind of particle that moves in an opposite direction to the first kind of particle under a given electric field will cause motion of the two types of particles through each other, breaking apart particle groups and reducing particle agglomeration through physical means.

In a preferred embodiment, the electrophoretic medium contains at least one type of particle whose average diameter is between about 0.25 and about 4 times the average diameter of a second type of particle bearing an opposite charge; desirably, the ratio of average particle mass between the two types of particles is between about 0.25 and about 4.00.

Also in a preferred embodiment, the electrophoretic medium contains at least two types of particles bearing charges of opposite polarity that from a distance apart of gap (G) under an applied electric field of magnitude F are able to achieve velocities V1 and V2 respectively such that:

$$V1+V2 > f(F,G)$$

where f is a function such that when the inequality if satisfied, particle agglomeration is reduced or eliminated.

Voltage Threshold Display

As already indicated, this invention provides an active matrix electro-optic display which uses an electro-optic medium with a voltage threshold. The use of this type of electro-optic medium reduces design constraints on the backplane of the electro-optic display.

As an example, consider a electro-optic medium that exhibits a strong voltage threshold at 5V. The term "strong voltage threshold" is used to mean that the medium does not switch at all for voltages less than the threshold, no matter how long the pulse. At voltages above the threshold, the medium switches normally. The use of such a medium alleviates the problem of data spikes caused by coupling of the data lines to the pixel electrodes (see Paragraphs 42-52 above); if the amplitude of the voltage spikes to the pixel is less than 5V, such a strong voltage threshold medium will not respond. A pixel storage capacitor used in such a display need only be sized to keep the voltage spikes experienced by the electro-optic medium below the voltage threshold, which could reduce the size of the storage capacitor substantially, as compared with capacitors required in prior art electro-optic displays in which the electro-optic medium displays no voltage threshold.

The present invention is not confined to the use of electro-optic media exhibiting strong voltage thresholds, but extends to the use of electro-optic media having only "weak voltage thresholds", a term which is used herein to refer to media which responds to voltages below a threshold applied for very long periods, but do not respond to such voltages applied over a short time of interest in the operation of an electro-optic display. For example, the period of interest could be a single scan frame (typically about 20 msec), or an entire image update (typically about 1000 msec).

The present invention may make use of any of the types of electro-optic media discussed above provided that the electro-optic media display strong or weak voltage thresholds. Incompatible monomer electrophoretic media having a voltage threshold, as described above, are generally preferred.

This invention allows relaxation of the design rules for a active matrix array, typically a thin film transistor (TFT) array. More specifically, this invention allows the use of a smaller storage capacitor per unit of pixel electrode area, thus making it feasible to produce a TFT backplane using lower-resolution technologies such as printing. In addition, by reducing the size of the storage capacitor, the size of the transistor can also be reduced. Decreasing the size of these two components would result in a substantial decrease in line capacitance, and thus power consumption, for the backplane. Thus, electro-optic displays of the present invention would have improved performance over conventional designs using prior art amorphous silicon construction.

It will be apparent to those skilled in the art that numerous changes and modifications can be made in the specific embodiments of the present invention described above without departing from the scope of the invention. Accordingly, the whole of the foregoing description is to be construed in an illustrative and not in a limitative sense.

The invention claimed is:

1. An electrophoretic medium comprising an electrically charged particle disposed in a fluid, the particle having a polymeric shell having repeating units derived from at least one monomer the homopolymer of which is incompatible with the fluid.

2. An electrophoretic medium according to claim 1 wherein the polymeric shell further comprises repeating units derived from at least one monomer the homopolymer of which is compatible with the fluid.

3. An electrophoretic medium according to claim 2 wherein the at least one monomer forming the compatible homopolymer comprises from about 15 to about 99 percent by weight of the polymer shell.

4. An electrophoretic medium according to claim 3 wherein the at least one monomer forming the compatible homopolymer comprises from about 50 to about 99 percent by weight of the polymer shell.

5. An electrophoretic medium according to claim 2 wherein the monomer forming the compatible homopolymer comprises lauryl methacrylate and the monomer forming the incompatible homopolymer comprises any one or more or styrene, t-butyl methacrylate and N-vinylpyrrolidone.

6. An electrophoretic medium according to claim 1 wherein the fluid comprises a hydrocarbon.

7. An electrophoretic medium according to claim 1 wherein the monomer forming the incompatible homopolymer comprises any one or more of acrylates and methacrylates formed from alcohols containing not more than about eight carbon atoms, said alcohols optionally containing hydroxyl or fluoro substitutents; acrylamides and methacrylamides; N,N-dialkylacrylamides; N-vinylpyrrolidone; styrene and derivatives thereof; vinyl esters; vinyl halides; polyfluoroaromatic molecules containing a polymerizable functional group; and silicone-containing molecules containing a polymerizable functional group.

8. An electrophoretic medium according to claim 7 wherein the monomer forming the incompatible homopolymer comprises any one or more of methyl methacrylate, ethyl methacrylate, butyl methacrylate, isobutyl methacrylate, t-butyl methacrylate, octyl methacrylate, 2-ethylhexyl methacrylate, 2-hydroxyethyl methacrylate, trifluoroethyl methacrylate, 2,2,3,4,4,4-hexafluorobutyl acrylate, 2,2,3,4,4,4-hexafluorobutyl methacrylate, acrylamide, acrylic acid, acrylonitrile, methyl vinyl ketone, methacrylamide, N-vinylpyrrolidone, styrene, vinyl acetate, vinyl chloride, vinylidene chloride, and pentafluorostyrene.

9. An electrophoretic medium according to claim 1 wherein the fluid and the particles are retained within a plurality of capsules or cells.

10. An electrophoretic display comprising an electrophoretic medium according to claim 1 and at least one electrode disposed adjacent the electrophoretic medium and arranged to apply an electric field thereto.

11. An electrophoretic particle comprising a pigment particle having a polymeric shell having repeating units derived from at least one monomer the homopolymer of which is incompatible with n-hexane.

12. An electrophoretic particle according to claim 11 wherein the polymeric shell further comprises repeating units derived from at least one monomer the homopolymer of which is compatible with n-hexane.

13. An electrophoretic particle according to claim 12 wherein the at least one monomer forming the compatible homopolymer comprises from about 15 to about 99 percent by weight of the polymer shell.

14. An electrophoretic particle according to claim 13 wherein the at least one monomer forming the compatible homopolymer comprises from about 50 to about 99 percent by weight of the polymer shell.

15. An electrophoretic particle according to claim 12 wherein the monomer forming the compatible homopolymer comprises lauryl methacrylate and the monomer forming the incompatible homopolymer comprises any one or more or styrene, t-butyl methacrylate and N-vinylpyrrolidone.

16. An electrophoretic particle according to claim 11 wherein the monomer forming the incompatible homopolymer comprises any one or more of acrylates and methacrylates formed from alcohols containing not more than about eight carbon atoms, said alcohols optionally containing hydroxyl or fluoro substitutents; acrylamides and methacrylamides; N,N-dialkylacrylamides; N-vinylpyrrolidone; styrene and derivatives thereof; vinyl esters; vinyl halides; polyfluoroaromatic molecules containing a polymerizable functional group; and silicone-containing molecules containing a polymerizable functional group.

17. An electrophoretic particle according to claim 11 wherein the monomer forming the incompatible homopolymer comprises any one or more of methyl methacrylate, ethyl methacrylate, butyl methacrylate, isobutyl methacrylate, t-butyl methacrylate, octyl methacrylate, 2-ethylhexyl methacrylate, 2-hydroxyethyl methacrylate, trifluoroethyl methacrylate, 2,2,3,4,4,4-hexafluorobutyl acrylate, 2,2,3,4,4,4-hexafluorobutyl methacrylate, acrylamide, acrylic acid, acrylonitrile, methyl vinyl ketone, methacrylamide, N-vinylpyrrolidone, styrene, vinyl acetate, vinyl chloride, vinylidene chloride, and pentafluorostyrene.

18. An electrophoretic particle according to claim 11 wherein the pigment particle comprises any one or more of titania, carbon black and copper chromite.

19. An electrophoretic particle comprising a pigment particle having a polymeric shell having repeating units derived from at least one monomer the homopolymer of which is incompatible with perfluorodecalin.

20. An electrophoretic particle comprising a pigment particle having a polymeric shell having repeating units derived from at least one monomer the homopolymer of which is incompatible with polydimethylsiloxane 200, viscosity 0.65 centistokes.

* * * * *